US011999788B2

(12) United States Patent
Okada et al.

(10) Patent No.: US 11,999,788 B2
(45) Date of Patent: Jun. 4, 2024

(54) TREATMENT OR PREVENTION METHOD OF RADIATION DAMAGE BY ADMINISTRATION OF IL-5 RECEPTOR ALPHA CHAIN BINDING ANTIBODY

(71) Applicants: Kyowa Kirin Co., Ltd., Tokyo (JP); The University of Tokyo, Tokyo (JP)

(72) Inventors: Kazuki Okada, Tokyo (JP); Kiyotoshi Mori, Tokyo (JP); Satoshi Uematsu, Tokyo (JP); Naoki Takemura, Tokyo (JP)

(73) Assignees: Kyowa Kirin Co., Ltd., Tokyo (JP); The University of Tokyo, Tokyo (JP)

( * ) Notice: Subject to any disclaimer, the term of this patent is extended or adjusted under 35 U.S.C. 154(b) by 279 days.

(21) Appl. No.: 17/530,150

(22) Filed: Nov. 18, 2021

(65) Prior Publication Data

US 2022/0135691 A1   May 5, 2022

Related U.S. Application Data

(62) Division of application No. 16/480,296, filed as application No. PCT/JP2018/001798 on Jan. 22, 2018, now Pat. No. 11,208,491.

(30) Foreign Application Priority Data

Jan. 24, 2017  (JP) ................................. 2017-010542
Nov. 2, 2017   (JP) ................................. 2017-212459

(51) Int. Cl.
*A61K 45/06*   (2006.01)
*C07K 14/715*  (2006.01)
*C07K 16/28*   (2006.01)

(52) U.S. Cl.
CPC ...... *C07K 16/2866* (2013.01); *C07K 14/7155* (2013.01); *A61K 45/06* (2013.01); *C07K 2317/565* (2013.01); *C07K 2317/73* (2013.01); *C07K 2317/76* (2013.01)

(58) Field of Classification Search
CPC .................................................. A61K 39/3955
See application file for complete search history.

(56) References Cited

U.S. PATENT DOCUMENTS

| | | | |
|---|---|---|---|
| 2002/0081623 | A1 | 6/2002 | Williams et al. |
| 2003/0096977 | A1 | 5/2003 | Koike et al. |
| 2004/0136996 | A1 | 7/2004 | Hosaka et al. |

FOREIGN PATENT DOCUMENTS

| | | |
|---|---|---|
| EP | 1 688 437 A1 | 8/2006 |
| JP | 09-507211 A | 7/1997 |
| WO | WO 1997/010354 A1 | 3/1997 |
| WO | WO 2001/060405 A1 | 8/2001 |
| WO | WO 2005/035583 A1 | 4/2005 |
| WO | WO-2012/158954 A1 | 11/2012 |

OTHER PUBLICATIONS

Hauer-Jensen, et al., "Radiation Eneropathy—Pathogenesis, Treatment, and Prevention," Nat Rev Gastroenterol. Hepatol., vol. 11, No. 8, pp. 470-479 (Aug. 2014).
Begg, et al., "Strategies to Improve Radiotherapy with Targeted Drugs," Nat. Rev. Cancer, vol. 11, pp. 239-253 (Apr. 2011).
Takemura et al., "Resident Myofibroblasts and Eosinophils Mediate Radiation-Induced Intestinal Fibrosis," Proceedings of Japanese Society of Immunology, 1 page (2014).
Nei et al., "GATA-1 Regulates the Generation and Function of Basophils," PNAS, vol. 110, No. 46, pp. 18620-18625 (Nov. 2013).
Lee et al., "Defining a Link with Asthma in Mice Congenitally Deficient in Eosinophils," Science, vol. 305, pp. 1773-1776 (Sep. 2004).
Humbles, et al., "A Critical Role for Eosinophils in Allergic Airways Remodeling," Science, vol. 305, pp. 1776-1779 (Sep. 2004).
Hogan et al., "A Critical Role for Eotaxin in Experimental Oral Antigen-Induced Eosinophilic Gastrointestinal Allergy," PNAS, vol. 97, No. 12, pp. 6681-6686 (Jun. 2000).
Yoshida et al., "Defective B-1 Cell Development and Impaired Immunity Against Angiostrongylus Cantonensis in IL-5Rα-Deficient Mice," Immunity, vol. 4, pp. 483-494 (May 1996).
Allen et al., "Precautionary Labeling of Foods for Allergen Content: Are We Ready for Global Framework?" World Allergy Organization Journal, vol. 7, No. 10, pp. 1-14 (2014).
Molfino et al., "Molecular and Clinical Rationale for Therapeutic Targeting of Interleukin-5 and its Receptor," Clinical Et Experimental Allergy, vol. 42, pp. 712-737 (2012).
Takemura, et al., Radiation-induced Small Intestinal Fibrosis is Induced by Eosinophil Inflammation caused by Epithelial Cell Death, 25th Meeting of the Japanese Society of Cell Death Research, p. 63, (Sep. 2016).
Terada, et al., Eosinophil Presentation Inhibitory Effects when CCR-3 is Blocked, Japanese Journal of Rhinology, vol. 38, No. 1, pp. 169-170 (1999).
Lach-Trifilieff, et al., "In Vitro and In Vivo Inhibition of Interleukin (IL)-5-Mediated Eosinopoiesis by Murine IL-5Rα Antisense Oligonucleotide," American Journal of Respiratory Cell and Molecular Biology, vol. 24, pp. 116-122 (2001).

(Continued)

Primary Examiner — Prema M Mertz
(74) Attorney, Agent, or Firm — Foley & Lardner LLP

(57) ABSTRACT

A therapeutic or prophylactic agent for radiation damage associated with radiation exposure, comprising an eosinophil-removing agent as an active ingredient and the like are provided as a technique for efficiently treating or preventing radiation damage associated with radiation exposure. According to the therapeutic or prophylactic agent comprising an eosinophil-removing agent according to the present invention, by suppressing migration and/or infiltration into target tissue and/or proliferation in the tissue of eosinophils and/or inhibiting the activity or function of the eosinophils, pathological conditions such as inflammatory responses and fibrosis of tissue can be suppressed to effectively treat or prevent radiation damage. Moreover, effective radiation therapy can be performed by suppressing radiation damage.

10 Claims, 20 Drawing Sheets

Specification includes a Sequence Listing.

(56) References Cited

OTHER PUBLICATIONS

Chen et al., "Radiation-Induced Lung Fibrosis in a Tumor-Bearing Mouse Model is Associated with Enhanced Type-2 Immunity," *Journ. Of Radiation Research*, vol. 57, No. 2, pp. 133-141 (2016).
Yamamoto et al., "Radiation-Induced Lung Injury Outside the Irradiated Area After Radiation Therapy for Breast Cancer," *Annals of the Japanese Respiratory Society*, vol. 2, No. 3, pp. 169-174 (2013).
Nakagome, et al., "Anti-IL-5 Antibody Therapy," *Asthma and Allergy*, vol. 29, No. 2, pp. 201-207 (2016).
International Search Report issued in International Patent Application No. PCT/JP2018/001798, dated Feb. 27, 2018.
Curtis Casey et al., "Hyper eosinophilic Syndrome", Clinical Reviews in Allergy and Immunology, Humana Press, vol. 50, No. 2, Oct. 16, 2015, pp. 240-251.
Supplemental Search Report Issued in European Patent Application No. 18745318.8 dated Oct. 21, 2020, thirteen (13) pages.
Rudikoff, et al., "Single Amino Acid Substitution Altering Antigen-Binding Specificity," *Proc. Natl. Acad. Sci.*, vol. 79, pp. 1979-1983 (Mar. 1982).
Janeway, et al., "Immunology, The Immune System in Health and Disease", 3$^{rd}$ Ed., Garland Publications, Inc., 14 pages (1997).
Beers et al., "The Merck Manual of Diagnosis and Therapy," *Hematology and Oncology*, 17$^{th}$ Edition, pp. 986-995 (1999).
Official Action issued in Taiwan Patent Application No. 107102563, dated Jan. 28, 2022.
Official Action issued in Japanese Patent Application No. 2018-564555, dated Mar. 1, 2022.
Kolbeck, et al., "MEDI-563, a Humanized Anti-IL-5 Receptor α mAb with Enhanced Antibody-Dependent Cell-Mediated Cytotoxicity Function," *J. Allergy Clin. Immunol.*, vol. 125, No. 6, pp. 1344-1353 (Jun. 2010).

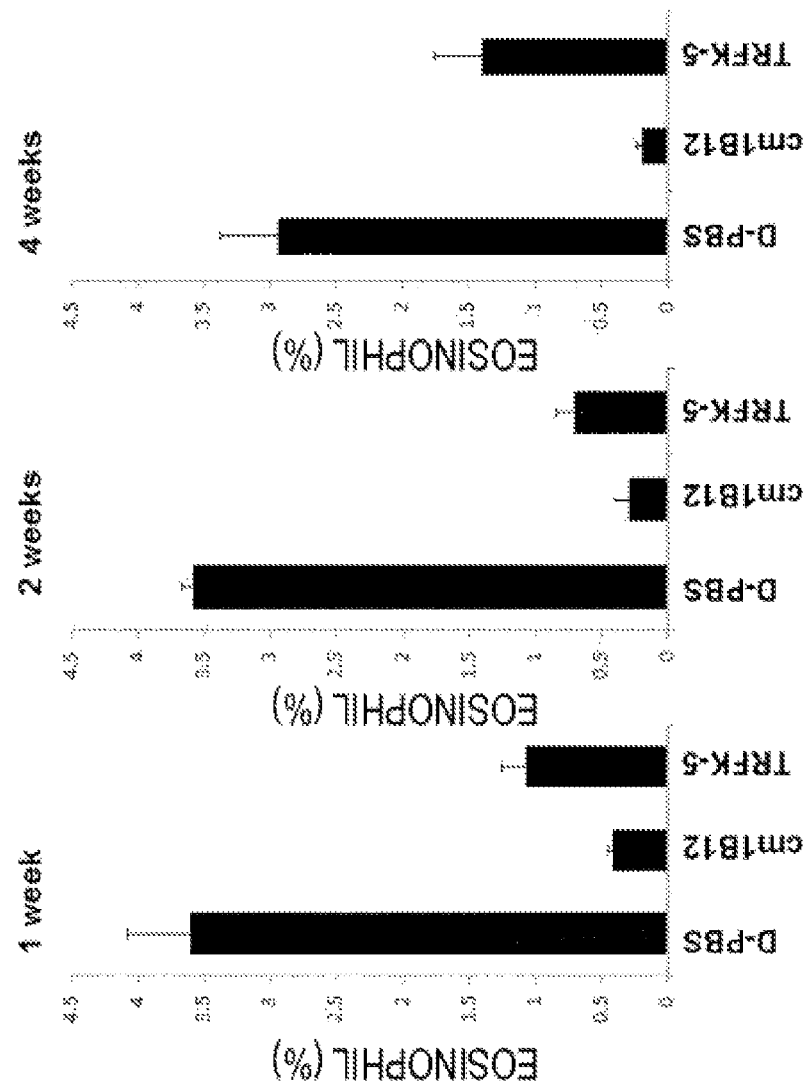

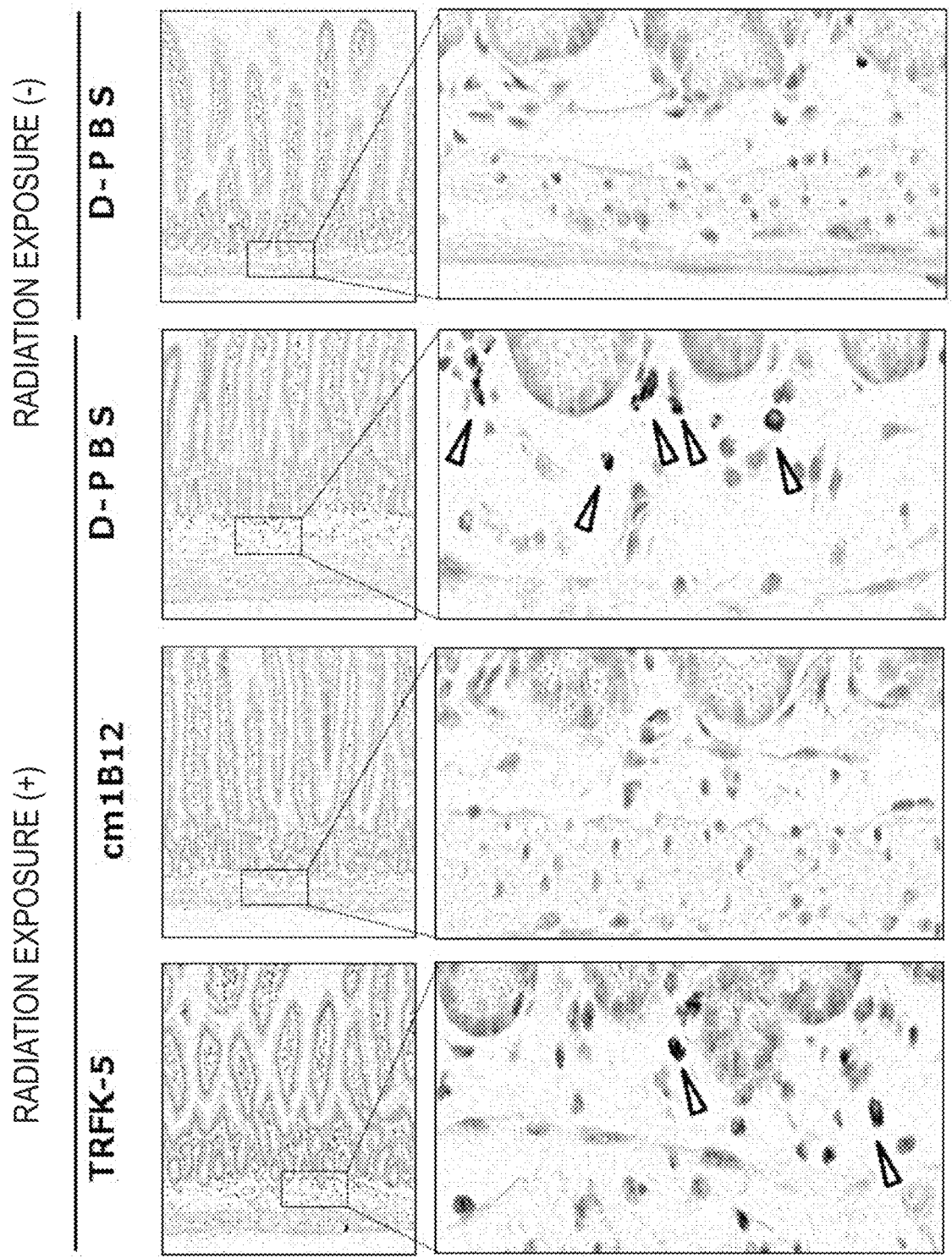

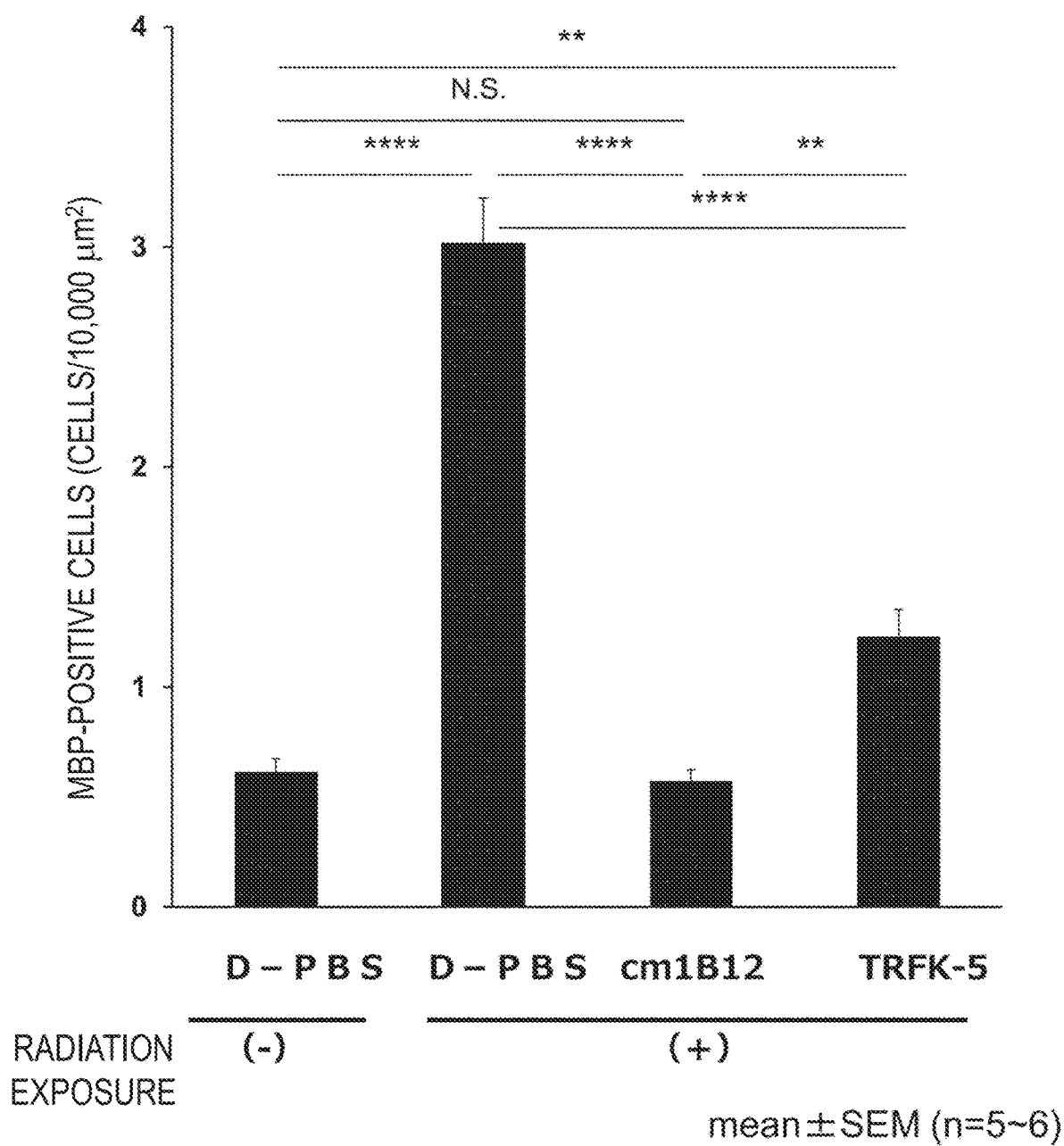

SIGNIFICANCE WAS TESTED BY BONFERRONI MULTIPLE TESTING N.S. p>0.05, * p>0.05,  p>0.01, * p>0.001, **** p>0.0001

FIG. 13

TREATMENT OR PREVENTION METHOD OF RADIATION DAMAGE BY ADMINISTRATION OF IL-5 RECEPTOR ALPHA CHAIN BINDING ANTIBODY

CROSS-REFERENCE TO RELATED APPLICATIONS

This application is a divisional of U.S. patent application Ser. No. 16/480,296, filed Jul. 23, 2019, now U.S. Pat. No. 11,208,491, which is the U.S. National Stage of International Patent Application No. PCT/JP2018/001798, filed Jan. 22, 2018, which claims priority from Japanese Patent Application No. 2017-212459, filed Nov. 2, 2017, and Japanese Patent Application No. 2017-010542, filed Jan. 24, 2017. The contents of these applications are incorporated herein by reference in their entirety.

SEQUENCE LISTING

The instant application contains a Sequence Listing which has been submitted electronically in ASCII format and is hereby incorporated by reference in its entirety.

TECHNICAL FIELD

The present invention relates to a therapeutic or prophylactic agent and a method for treatment or prevention for radiation damage. Particularly, the present invention relates to a therapeutic or prophylactic agent for radiation damage associated with radiation exposure, comprising an eosinophil-removing agent as an active ingredient and the like.

BACKGROUND ART

The radiotherapy is one of cancer therapies including surgical therapies and chemotherapies and a therapy widely applied to the treatment of cancers such as pelvic cancer and prostate cancer. It aims to radically cure cancer or alleviate symptoms by concentrating the irradiation to the tumor and reducing the irradiation to the neighboring normal tissue as much as possible.

Meanwhile, one of the issues of the radiotherapy is radiation damage to normal tissue. The radiation damage is divided into the two large groups: early radiation damage, which develops during radiation therapy or in several months after the treatment, and delayed radiation damage, which develops several months to several decades after the treatment (Non Patent Literature 1).

The radiation enteritis is radiation damage induced in normal enteral cells when cancer in the abdomen or pelvis is irradiated. Examples of early radiation damage in the radiation enteritis include emesis, eating disorder, mucosal inflammation, hemorrhage, diarrhea, constipation, hematochezia, and the like. Examples of delayed radiation damage in the radiation enteritis include intestinal fibrosis, gastroduodenal ulcer, stenosis, occlusion, fistula formation, hemorrhage, perforation, ulceration, fecal incontinence, chronic diarrhea, and the like. Therapies for early damage mainly involve bowel control combined with palliative therapies mainly involving an administration treatment with an agent such as steroid, antioxidant, an anti-inflammatory drug, a radical scavenger formulation, and an antibiotic. Examples of therapies for delayed radiation damage include the hyperbaric oxygen therapy, argon plasma coagulation, and surgical resection.

The early radiation damage in the radiation enteritis is a pathological condition mainly involving mucosal disorder and mucosal inflammation and markedly reduces the quality of life (QOL) of patients undergoing radiation therapy. Furthermore, if severe early radiation damage develops, then cessation of treatment or alteration of treatment schedule become unavoidable. Therapeutic agents including steroid, antioxidant, anti-inflammatory drugs, radical scavenger formulations, and antibiotics are used for the early radiation damage, but the therapeutic effect of them is limited and there are no therapeutic agents that can be expected to have sufficient therapeutic effect (Non Patent Literature 1, 2).

The delayed radiation damage in the radiation enteritis is a progressive pathological condition with chronic symptoms mainly including fibrosis of tissue, atrophy of the mucosa, and angiosclerosis and markedly reduces the QOL of the patient for a lifetime. There are no effective therapeutic agents for the delayed radiation damage and a surgical treatment is administered when the damage is severe, but no effective method for treatment is established (Non Patent Literature 1).

Eosinophils is suggested to be involved in the mechanisms for inducing radiation enteritis by the analysis using a model of radiation enteritis in which the abdomen of wildtype mice is irradiated (Non Patent Literature 3). For example, in the radiation enteritis model, progression of small intestinal fibrosis, which is a main delayed damage, is induced from several months after the irradiation and infiltration and activation of eosinophils have been confirmed in the small intestinal submucosa, which is the site of fibrosis.

Moreover, a study with a radiation enteritis model using Δdb1GATA mice, which genetically lacks the eosinophil has revealed that fibrosis in the small intestinal submucosa is suppressed. Meanwhile, the Δdb1GATA mice are widely used as eosinophil deficient mice in general, but effects other than eosinophil deficiency, such as occurrence of a decrease in basophils and mild anemia have been reported (Non Patent Literature 4).

Moreover, the Δdb1GATA mice have been reported to have different phenotypes in an asthma model from those of PHIL mice, which are also widely used as eosinophil deficient mice (Non Patent Literature 5, 6). Therefore, it is not certain that the mechanisms by which the development of radiation enteritis is suppressed in the Δdb1GATA mice are dependent on only the lack of eosinophils.

Examples of possible methods for removing eosinophils from the small intestine include methods for depleting interleukin-5 (IL-5), which is an eosinophil activator. However, an analysis with IL-5 deficient mice has revealed that while blood eosinophils markedly decrease, small intestinal eosinophils do not decrease (Non Patent Literature 7). Moreover, in an analysis with the IL-5Rα deficient mice, in which the IL-5 receptor is deleted, decrease of blood eosinophils does not go beyond around 50% (Non Patent Literature 8).

Known antibodies that specifically bind to IL-5 ligand or IL-5 receptor include the anti-IL-5 humanized antibodies Mepolizumab (IgG1), Reslizumab (IgG4/κ), and the anti-IL-5Rα antibody Benralizumab (MEDI-563) [Fasenra (R)] (Patent Literature 1 and 2 and Non-Patent Literature 9 and 10).

CITATION LIST

Patent Literature

Patent Literature 1:
International Publication No. WO 1997/10354
Patent Literature 2:
International Publication No. WO 2005/35583

Non Patent Literature

Non Patent Literature 1:
Nat. Rev. Gastroenterol. Hepatol., 2014, 11 (8): 470-479
Non Patent Literature 2:
Nat. Rev. Cancer, 2011, 11 (4): 239-253
Non Patent Literature 3:
Proceedings of the Japanese Society for Immunology, 2014, 43:3-H-W50-4
Non Patent Literature 4:
Proc. Natl. Acad. Sci., 2013, 110 (46): 18620-18625
Non Patent Literature 5:
Science, 2004, 305: 1773-1776
Non Patent Literature 6:
Science, 2004, 305: 1776-1779
Non Patent Literature 7:
Proc. Natl. Acad. Sci., 2000, 97 (12): 6681-6686
Non Patent Literature 8:
Immunity, 1996, 4 (5): 483-494
Non-Patent Literature 9:
World Allergy Organization J., 2014, 7:1-14
Non Patent Literature 10:
Clinical Et. Experimental Allergy, 2010 42, 712-737

SUMMARY OF INVENTION

Technical Problem

A main object of the present invention is to provide a technique for efficiently treating or preventing radiation damage associated with radiation exposure and to provide a method of radiation therapy or a method for treating cancer wherein radiation damage associated with radiation exposure is suppressed.

Solution to Problem

To achieve the aforementioned object, the present inventors have, as a result of diligent studies, revealed for the first time that intestinal eosinophils can markedly be decreased by eosinophil-removing agents such as eosinophil-removing antibodies having the neutralization activity of the ligand/receptor and eosinophil-removing antibodies to which high effector activity is conferred. The present inventors found that the administration of the eosinophil-removing agents can decrease eosinophils in tissue to suppress the development and progression of pathological conditions of radiation damage and suppress radiation damage associated with radiation exposure to increase the tolerance dose in radiation therapies.

Based on these findings, the present invention provides the following [1] to [70].

[1] A therapeutic or prophylactic agent for radiation damage associated with radiation exposure, comprising an eosinophil-removing agent as an active ingredient.
[2] The therapeutic or prophylactic agent according to [1], wherein the radiation is X-ray radiation or γ-ray radiation.
[3] The therapeutic or prophylactic agent according to [1] or [2], wherein the radiation exposure is radiation exposure associated with radiation therapy.
[4] The therapeutic or prophylactic agent according to [3], wherein the radiation therapy is radiation therapy for any cancer selected from the group consisting of small intestinal cancer, colorectal cancer, gastrointestinal stromal tumor (GIST), gastrointestinal carcinoid, gastric cancer, esophageal cancer, liver cancer, gallbladder/biliary cancer, pancreatic cancer, pancreatic/gastrointestinal neuroendocrine tumor, Langerhans cell histiocytosis, renal cell cancer, renal pelvic/ureteral cancer, adrenal tumor, osteosarcoma, soft tissue sarcoma, malignant lymphoma, bladder cancer, urethral cancer, prostate cancer, testicular tumor, penile cancer, endometrial cancer, cervical cancer, uterine tumor, ovarian tumor, female genital cancer, lung cancer, thymic tumor, mesothelioma, breast cancer, hematopoietic tumor, leukemia, myeloproliferative disease, and multiple myeloma.
[5] The therapeutic or prophylactic agent according to any of [1] to [4], wherein the radiation damage is early radiation damage or delayed radiation damage.
[6] The therapeutic or prophylactic agent according to any of [1] to [5], wherein the radiation damage is damage to any one or more organs selected from the group consisting of the small intestine, the large intestine, the stomach, the bladder, the liver, and the kidney.
[7] The therapeutic or prophylactic agent according to any of [1] to [6], wherein the eosinophil-removing agent is an antibody or a fragment thereof that binds to an antigen expressed on cell surface of eosinophils or an antibody or a fragment thereof that binds to a ligand that binds to the antigen.
[8] The therapeutic or prophylactic agent according to [7], wherein the antibody or the fragment thereof is an antibody or a fragment thereof that binds to any antigen selected from the group consisting of IL-5 receptor α chain and/or β chain, CRTH2, Siglec8, CCR3, IL-5, PGD2, Siglec8 ligand, CCL5, CCL7, CCL11, CCL13, CCL15, CCL24, CCL26, and CCL28, preferably an antibody or a fragment thereof that binds to IL-5 receptor α chain or an IL-5 ligand.
[9] The therapeutic or prophylactic agent according to [7] or [8], wherein the antibody or the fragment thereof is an antibody or a fragment thereof having antibody-dependent cellular cytotoxicity activity (ADCC activity) and/or neutralization activity.
[10] The therapeutic or prophylactic agent according to any of [7] to [9], wherein the antibody or the fragment thereof is a monoclonal antibody or a genetically modified antibody or a fragment thereof.
[11] The therapeutic or prophylactic agent according to any of [7] to [10], wherein the antibody or the fragment thereof is an antibody or a fragment thereof comprising a human Fc region or a human constant region.
[12] The therapeutic or prophylactic agent according to any of [7] to [11], wherein the antibody or the fragment thereof is any antibody selected from the group consisting of a chimeric antibody, a humanized antibody, and a human antibody, or a fragment thereof.
[13] A therapeutic or prophylactic agent for radiation damage associated with radiation exposure, comprising an eosinophil-removing agent as an active ingredient, wherein the eosinophil-removing agent in a radiation therapy increases a tolerance radiation dose of a patient to be treated, extends the duration of the radiation therapy, and/or suppresses radiation damage associated with the radiation therapy.

[14] A method for increasing a tolerance radiation dose of a patient to be treated, a method for extending the duration of a radiation therapy, and/or a method for suppressing radiation damage associated with radiation exposure, comprising use of an eosinophil-removing agent in radiation therapy.
[15] The method according to [14], wherein the radiation is X-ray radiation or γ-ray radiation.
[16] The method according to [14] or [15], wherein the radiation exposure is radiation exposure associated with radiation therapy.
[17] The method according to any of [14] to [16], wherein the radiation therapy is radiation therapy for any cancer selected from the group consisting of small intestinal cancer, colorectal cancer, gastrointestinal stromal tumor (GIST), gastrointestinal carcinoid, gastric cancer, esophageal cancer, liver cancer, gallbladder/biliary cancer, pancreatic cancer, pancreatic/gastrointestinal neuroendocrine tumor, Langerhans cell histiocytosis, renal cell cancer, renal pelvic/ureteral cancer, adrenal tumor, osteosarcoma, soft tissue sarcoma, malignant lymphoma, bladder cancer, urethral cancer, prostate cancer, testicular tumor, penile cancer, endometrial cancer, cervical cancer, uterine tumor, ovarian tumor, female genital cancer, lung cancer, thymic tumor, mesothelioma, breast cancer, hematopoietic tumor, leukemia, myeloproliferative disease, and multiple myeloma.
[18] The method according to any of [14] to [17], wherein the radiation damage is early radiation damage or delayed radiation damage.
[19] The method according to any of [14] to [18], wherein the radiation damage is damage to any one or more organs selected from the group consisting of the small intestine, the large intestine, the stomach, the bladder, the liver, and the kidney.
[20] The method according to any of [14] to [19], wherein the eosinophil-removing agent is an antibody or a fragment thereof that binds to an antigen expressed on cell surface of eosinophils or an antibody or a fragment thereof that binds to a ligand that binds to the antigen.
[21] The method according to [20], wherein the antibody or a fragment thereof is an antibody or a fragment thereof that binds to any antigen selected from the group consisting of IL-5 receptor α chain and/or β chain, CRTH2, Siglec8, CCR3, IL-5, PGD2, Siglec8 ligand, CCL5, CCL7, CCL11, CCL13, CCL15, CCL24, CCL26, and CCL28, preferably an antibody or a fragment thereof that binds to IL-5 receptor α chain or an IL-5 ligand.
[22] The method according to [20] or [21], wherein the antibody or the fragment thereof is an antibody or a fragment thereof having antibody-dependent cellular cytotoxicity activity (ADCC activity) and/or neutralization activity.
[23] The method according to any of [20] to [22], wherein the antibody or the fragment thereof is a monoclonal antibody or a genetically modified antibody or a fragment thereof.
[24] The method according to any of [20] to [23], wherein the antibody or the fragment thereof is an antibody or a fragment thereof comprising a human Fc region or a human constant region.
[25] The method according to any of [20] to [24], wherein the antibody or the fragment thereof is any antibody selected from the group consisting of a chimeric antibody, a humanized antibody, and a human antibody, or a fragment thereof.
[26] A method for treating or preventing radiation damage associated with radiation exposure, comprising a step of administering a therapeutic agent or a prophylactic agent comprising an eosinophil-removing agent as an active ingredient.
[27] The method for treatment or prevention according to [26], wherein the radiation is X-ray radiation or γ-ray radiation.
[28] The method for treatment or prevention according to [26] or [27], wherein the radiation exposure is radiation exposure associated with radiation therapy.
[29] The method for treatment or prevention according to [28], wherein the radiation therapy is radiation therapy for any cancer selected from the group consisting of small intestinal cancer, colorectal cancer, gastrointestinal stromal tumor (GIST), gastrointestinal carcinoid, gastric cancer, esophageal cancer, liver cancer, gallbladder/biliary cancer, pancreatic cancer, pancreatic/gastrointestinal neuroendocrine tumor, Langerhans cell histiocytosis, renal cell cancer, renal pelvic/ureteral cancer, adrenal tumor, osteosarcoma, soft tissue sarcoma, malignant lymphoma, bladder cancer, urethral cancer, prostate cancer, testicular tumor, penile cancer, endometrial cancer, cervical cancer, uterine tumor, ovarian tumor, female genital cancer, lung cancer, thymic tumor, mesothelioma, breast cancer, hematopoietic tumor, leukemia, myeloproliferative disease, and multiple myeloma.
[30] The method for treatment or prevention according to any of [26] to [29], wherein the radiation damage is early radiation damage or delayed radiation damage.
[31] The method for treatment or prevention according to any of [26] to [30], wherein the radiation damage is damage to any one or more organs selected from the group consisting of the small intestine, the large intestine, the stomach, the bladder, the liver, and the kidney.
[32] The method for treatment or prevention according to any of [26] to [31], wherein the eosinophil-removing agent is an antibody or a fragment thereof that binds to an antigen expressed on cell surface of eosinophils or an antibody or a fragment thereof that binds to a ligand that binds to the antigen.
[33] The method for treatment or prevention according to [32], wherein the antibody or the fragment thereof is an antibody or a fragment thereof that binds to any antigen selected from the group consisting of IL-5 receptor α chain and/or β chain, CRTH2, Siglec8, CCR3, IL-5, PGD2, Siglec8 ligand, CCL5, CCL7, CCL11, CCL13, CCL15, CCL24, CCL26, and CCL28, preferably an antibody or a fragment thereof that binds to IL-5 receptor α chain or an IL-5 ligand.
[34] The method for treatment or prevention according to [32] or [33], wherein the antibody or the fragment thereof is an antibody or a fragment thereof having antibody-dependent cellular cytotoxicity activity (ADCC activity) and/or neutralization activity.
[35] The method for treatment or prevention according to any of [32] to [34], wherein the antibody or the fragment thereof is a monoclonal antibody or a genetically modified antibody or a fragment thereof.
[36] The method for treatment or prevention according to any of [32] to [35], wherein the antibody or the fragment thereof is an antibody or a fragment thereof comprising a human Fc region or a human constant region.
[37] The method for treatment or prevention according to any of [32] to [36], wherein the antibody or the fragment thereof is any antibody selected from the group consisting of a chimeric antibody, a humanized antibody, and a human antibody, or a fragment thereof.
[38] A method of radiation therapy, comprising use of an eosinophil-removing agent.
[39] The method of radiation therapy according to [38], wherein radiation damage by radiation exposure is reduced.

[40] The method of radiation therapy according to [38] or [39], wherein the radiation is X-ray radiation or γ-ray radiation.

[41] The method of radiation therapy according to [39] or [40], wherein the radiation exposure is radiation exposure associated with radiation therapy.

[42] The method of radiation therapy according to any of [38] to [41], comprising irradiation with a single dose and/or a total dose of radiation increased by 5% or more in comparison with the dose without administration of any eosinophil-removing agent.

[43] The method of radiation therapy according to any of [38] to [42], comprising irradiation with a dose of radiation that is 5% or higher than a tolerance radiation dose.

[44] The method of radiation therapy according to any of [38] to [43], comprising a larger number of events of irradiation in comparison the number of events of irradiation without administration of any eosinophil-removing agent.

[45] The method of radiation therapy according to any of [38] to [44], the radiation therapy is radiation therapy for any cancer selected from the group consisting of small intestinal cancer, colorectal cancer, gastrointestinal stromal tumor (GIST), gastrointestinal carcinoid, gastric cancer, esophageal cancer, liver cancer, gallbladder/biliary cancer, pancreatic cancer, pancreatic/gastrointestinal neuroendocrine tumor, Langerhans cell histiocytosis, renal cell cancer, renal pelvic/ureteral cancer, adrenal tumor, osteosarcoma, soft tissue sarcoma, malignant lymphoma, bladder cancer, urethral cancer, prostate cancer, testicular tumor, penile cancer, endometrial cancer, cervical cancer, uterine tumor, ovarian tumor, female genital cancer, lung cancer, thymic tumor, mesothelioma, breast cancer, hematopoietic tumor, leukemia, myeloproliferative disease, and multiple myeloma.

[46] The method of radiation therapy according to any of [39] to [45], wherein the radiation damage is early radiation damage or delayed radiation damage.

[47] The method of radiation therapy according to any of [39] to [46], wherein the radiation damage is damage to any one or more organs selected from the group consisting of the small intestine, the large intestine, the stomach, the bladder, the liver, and the kidney.

[48] The method of radiation therapy according to any of [38] to [47], wherein the eosinophil-removing agent is an antibody or a fragment thereof that binds to an antigen expressed on cell surface of eosinophils or an antibody or a fragment thereof that binds to a ligand that binds to the antigen.

[49] The method of radiation therapy according to [48], wherein the antibody or the fragment thereof is an antibody or a fragment thereof that binds to any antigen selected from the group consisting of IL-5 receptor α chain and/or β chain, CRTH2, Siglec8, CCR3, IL-5, PGD2, Siglec8 ligand, CCL5, CCL7, CCL11, CCL13, CCL15, CCL24, CCL26, and CCL28, preferably an antibody or a fragment thereof that binds to IL-5 receptor α chain or an IL-5 ligand.

[50] The method of radiation therapy according to [48] or [49], wherein the antibody or the fragment thereof is an antibody or a fragment thereof having antibody-dependent cellular cytotoxicity activity (ADCC activity) and/or neutralization activity.

[51] The method of radiation therapy according to any of [48] to [50], wherein the antibody or the fragment thereof is a monoclonal antibody or a genetically modified antibody or a fragment thereof.

[52] The method of radiation therapy according to any of [48] to [51], wherein the antibody or the fragment thereof is an antibody or a fragment thereof comprising a human Fc region or a human constant region.

[53] The method of radiation therapy according to any of [48] to [52], wherein the antibody or the fragment thereof is any antibody selected from the group consisting of a chimeric antibody, a humanized antibody, and a human antibody, or a fragment thereof.

[54] A method for treating cancer, comprising combined use of an eosinophil-removing agent and irradiation.

[55] The method for treating cancer according to [54], wherein the radiation is X-ray radiation or γ-ray radiation.

[56] The method for treating cancer according to [54] or [55], wherein the irradiation is irradiation with a single dose and/or a total dose of radiation increased by 5% or more in comparison with the dose without administration of any eosinophil-removing agent.

[57] The method for treating cancer according to any of [54] to [56], wherein the irradiation is irradiation with a dose of radiation that is 5% or higher than a tolerance radiation dose.

[58] The method for treating cancer according to any of [54] to [57], wherein the irradiation comprises a larger number of events of irradiation in comparison with the number of events of irradiation without administration of any eosinophil-removing agent.

[59] The method for treating cancer according to any of [54] to [58], wherein the radiation therapy is radiation therapy for any cancer selected from the group consisting of small intestinal cancer, colorectal cancer, gastrointestinal stromal tumor (GIST), gastrointestinal carcinoid, gastric cancer, esophageal cancer, liver cancer, gallbladder/biliary cancer, pancreatic cancer, pancreatic/gastrointestinal neuroendocrine tumor, Langerhans cell histiocytosis, renal cell cancer, renal pelvic/ureteral cancer, adrenal tumor, osteosarcoma, soft tissue sarcoma, malignant lymphoma, bladder cancer, urethral cancer, prostate cancer, testicular tumor, penile cancer, endometrial cancer, cervical cancer, uterine tumor, ovarian tumor, female genital cancer, lung cancer, thymic tumor, mesothelioma, breast cancer, hematopoietic tumor, leukemia, myeloproliferative disease, and multiple myeloma.

[60] The method for treating cancer according to any of [54] to [59], wherein the eosinophil-removing agent is an antibody or the fragment thereof that binds to an antigen expressed on cell surface of eosinophils or an antibody or a fragment thereof that binds to a ligand that binds to the antigen.

[61] The method for treating cancer according to [60], wherein the antibody or the fragment thereof is an antibody or a fragment thereof that binds to any antigen selected from the group consisting of IL-5 receptor α chain, IL-5 receptor β chain, CRTH2, Siglec8, CCR3, IL-5, PGD2, Siglec8 ligand, CCL5, CCL7, CCL11, CCL13, CCL15, CCL24, CCL26, and CCL28.

[62] The method for treating cancer according to [60] or [61], wherein the antibody or the fragment thereof is an antibody or a fragment thereof having antibody-dependent cellular cytotoxicity activity and/or neutralization activity.

[63] The method for treating cancer according to any of [60] to [62], wherein the antibody or the fragment thereof is a monoclonal antibody or a genetically modified antibody or a fragment thereof.

[64] The method for treating cancer according to any of [60] to [63], wherein the antibody or the fragment thereof is an antibody or a fragment thereof comprising a human Fc region or a human constant region.

[65] The method for treating cancer according to any of [60] to [64], wherein the antibody or the fragment thereof is any antibody selected from the group consisting of a chimeric antibody, a humanized antibody, and a human antibody, or a fragment thereof.

[66] A therapeutic or prophylactic agent for radiation damage associated with radiation exposure, comprising an eosinophil-removing agent as an active ingredient, wherein the eosinophil-removing agent increases a tolerance radiation dose of a patient to be treated by 5% or more in a radiation therapy.

The therapeutic or prophylactic agent according to any of [1] to [13], the method according to any of [14] to [25], the method for treatment or prevention according to any of [26] to [37] or [66], the method of radiation therapy according to any of [38] to [53], or the method for treating cancer according to any of [54] to [65], wherein the eosinophil-removing agent is one or more antibodies or a fragments thereof selected from the group consisting of:

(1) an antibody that binds to an epitope present in the 1st to 313rd positions in the amino acid sequence of the extracellular region of human IL-5Rα (here, the extracellular region refers to the N-terminal region, other than the region from the transmembrane region to the C-terminal in the human IL-5Rα),
(2) an antibody that binds to an epitope present in the 41st to 61st positions in the amino acid sequence of the extracellular region of human IL-5Rα,
(3) an antibody that binds to an epitope present in the 52nd to 61st positions in the amino acid sequence of the extracellular region of human IL-5Rα,
(4) an antibody that binds to an epitope containing the 61st amino acid residue in the extracellular region of human IL-5Rα,
(5) an antibody that binds to an epitope to which the anti-human IL-5Rα antibody Benralizumab binds,
(6) an antibody that binds to the same epitope as that of the anti-human IL-5Rα antibody Benralizumab,
(7) an antibody comprising a CDR of the anti-human IL-5Ra antibody Benralizumab,
(8) an antibody comprising a heavy chain variable region (hereinafter, abbreviated as VH) and a light chain variable region (hereinafter, abbreviated as VL) of the anti-human IL-5Ra antibody Benralizumab,
(9) the anti-human IL-5Rα antibody Benralizumab,
(10) an anti-IL-5R antibody comprising H chain CDRs 1 to 3 respectively comprising the amino acid sequences of SEQ ID NOs: 1 to 3 and L chain CDRs 1 to 3 respectively comprising the amino acid sequences of SEQ ID NOs: 4 to 6,
(11) an anti-IL-5R antibody comprising VH comprising the amino acid sequence of SEQ ID NO: 7 and VL comprising the amino acid sequence of SEQ ID NO: 8,
(12) an anti-IL-5R antibody comprising an H chain comprising the amino acid sequence of SEQ ID NO: 9 and an L chain comprising the amino acid sequence of SEQ ID NO: 10,
(13) an anti-IL-5R antibody comprising H chain CDRs 1 to 3 contained in the amino acid sequence of SEQ ID NO: 14 and L chain CDRs 1 to 3 contained in the amino acid sequence of SEQ ID NO: 17,
(14) an anti-IL-5R antibody comprising VH comprising the amino acid sequence of SEQ ID NO: 14 and VL comprising the amino acid sequence of SEQ ID NO: 17,
(15) an antibody that binds to an epitope to which the humanized anti-human IL-5 antibody Mepolizumab (IgG1) binds,
(16) an antibody that binds to the same epitope as that of the humanized anti-human IL-5 antibody Mepolizumab (IgG1),
(17) an antibody comprising a CDR of the humanized anti-human IL-5 antibody Mepolizumab (IgG1),
(18) an antibody comprising VH and VL of the humanized anti-human IL-5 antibody Mepolizumab (IgG1),
(19) the humanized anti-human IL-5 antibody Mepolizumab (IgG1),
(20) an antibody that binds to an epitope to which the anti-human IL-5 antibody Reslizumab (IgG4/κ) binds,
(21) an antibody that binds to the same epitope as that of the anti-human IL-5 antibody Reslizumab (IgG4/κ),
(22) an antibody comprising a CDR of the anti-human IL-5 antibody Reslizumab (IgG4/κ),
(23) an antibody comprising VH and VL of the anti-human IL-5 antibody Reslizumab (IgG4/κ), and
(24) the anti-human IL-5 antibody Reslizumab (IgG4/κ).

[68] The therapeutic or prophylactic agent according to any of [1] to [13], the method according to any of [14] to [25], the method for treatment or prevention according to any of [26] to [37] or [66], the method of radiation therapy according to any of [38] to [53], or the method for treating cancer according to any of [54] to [65], wherein the core fucose linked to the 297th position in the Fc region in the antibody or the fragment thereof is decreased or deleted.

[69] An anti-IL-5R antibody comprising H chain CDRs 1 to 3 contained in the amino acid sequence of SEQ ID NO: 14 and L chain CDRs 1 to 3 contained in the amino acid sequence of SEQ ID NO: 17, or
an anti-IL-5R antibody comprising VH comprising the amino acid sequence of SEQ ID NO: 14 and VL comprising the amino acid sequence of SEQ ID NO: 17.

[70] The antibody or the fragment thereof according to [69], wherein the antibody is any 1 selected from the group consisting of a genetically recombined rat antibody, a rat-mouse chimeric antibody, a rat-human chimeric antibody, a humanized antibody, and a human antibody.

[71] The antibody or the fragment thereof according to [69] or [70], comprising a human Fc region.

[72] A DNA encoding an antibody or a fragment thereof according to any of [69] to [71].

[73] An antibody producing cell comprising the DNA according to [72] introduced therein.

[74] A method for producing an antibody or a fragment thereof according to [69] to [71], comprising culturing the antibody producing cell according to [73] and obtaining and purifying supernatant of the culture.

Advantageous Effects of Invention

The present invention provides a technique to efficiently treat or prevent radiation damage associated with radiation exposure. According to the therapeutic or prophylactic agent comprising an eosinophil-removing agent and the method for treatment or prevention comprising use thereof according to the present invention, by suppressing migration and/or infiltration into target tissue and/or proliferation in the tissue of eosinophils and/or inhibiting the activity or function of the eosinophils, pathological conditions such as inflammatory responses and fibrosis of tissue can be suppressed to effectively treat or prevent radiation damage.

BRIEF DESCRIPTION OF DRAWINGS

FIG. 4B illustrates the result of analysis of change in the ratio of blood eosinophils by administration of the cm1B12 antibody or the TRFK-5 antibody. The ordinate represents the ratio (%) of the blood eosinophil fraction relative to the fraction defined as the total cell number in FIG. 4A.

FIG. 7A illustrates the result of analysis of the effect of administration of the cm1B12 antibody or the TRFK-5 antibody on the number of eosinophils infiltrated in the small intestinal submucosa 13 weeks after irradiation. The arrow heads indicate eosinophils.

FIG. 7B illustrates the result of analysis of the effect of administration of the cm1B12 antibody or the TRFK-5 antibody on the number of eosinophils per unit area in the small intestinal submucosa 13 weeks after irradiation.

FIG. 13 illustrates the result of analysis of the correlation between hyperplasia in the intestinal submucosa 20 weeks after irradiation and the total dose of radiation and the effect of administration of the cm1B12 antibody. The ordinate represents the thickness (μm) of the submucosa. The abscissa represents the total dose and the administered agents. The data of survivor individuals is expressed as the mean. The data of euthanized individuals is represented by the filled circles.

DESCRIPTION OF EMBODIMENTS

Figure 1:
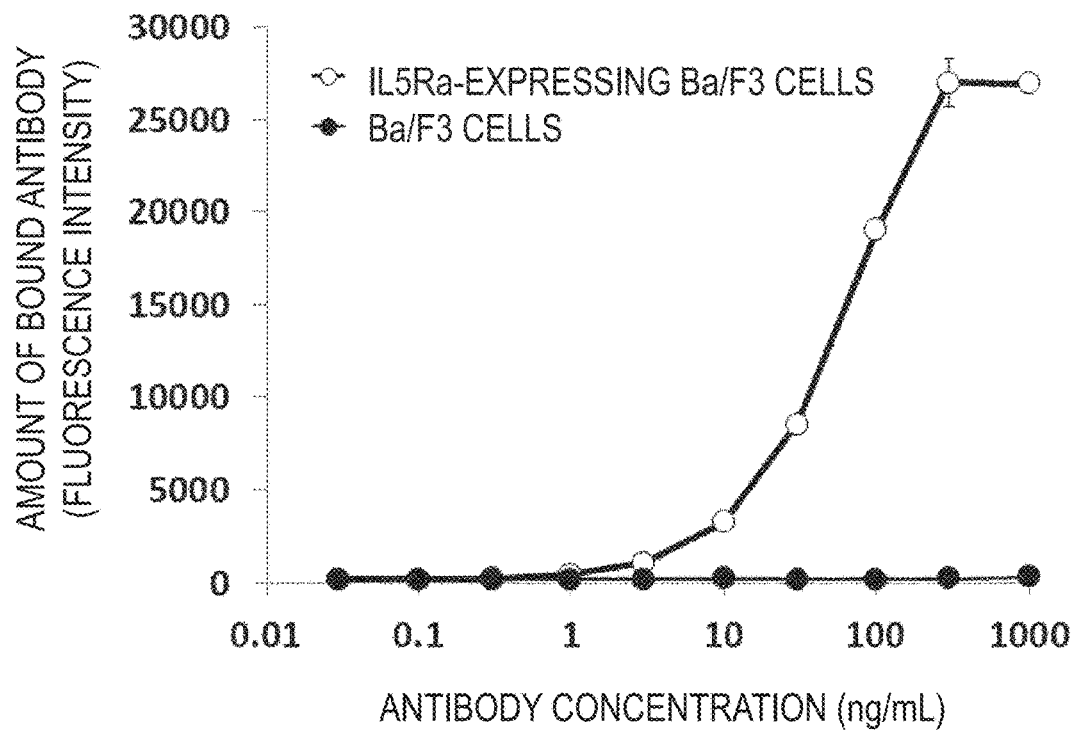
FIG. 1 illustrates the result of analysis of specific binding of the cm1B12 antibody to IL5Rα-expressing Ba/F3 cells by flow cytometry. The open circle indicates the amount bound to the IL5Rα-expressing Ba/F3 cells and the filled circle indicates the amount bound to the Ba/F3 cells. The ordinate represents the amount of bound antibody (fluorescence intensity) and the abscissa represents the antibody concentration.

Preferred embodiments for carrying out the present invention will be described below. The embodiments described below are examples of representative embodiments of the present invention, and these are not to be construed as a limitation of the scope of the present invention.

The present invention relates to a therapeutic or prophylactic agent for radiation damage associated with radiation exposure, comprising an eosinophil-removing agent and a method for treating or preventing radiation damage associated with radiation exposure comprising use of the therapeutic or prophylactic agent.

Moreover, the present invention also encompasses a method for suppressing radiation damage associated with radiation exposure, comprising use of an eosinophil-removing agent, a method for increasing a radiation tolerance dose of a patient to be treated in radiation therapy by using an eosinophil-removing agent, and a method for extending the duration of radiation therapy for a patient to be treated in radiation therapy by using an eosinophil-removing agent.

The "radiation" in the present invention refers to any electromagnetic wave and particle ray. Specific examples of the radiation include α-ray, β-ray, and γ-ray emitted from radioactive substances and X-ray, proton beam, carbon ion beam, neutron beam, and electron beam generated artificially, and the like.

The "radiation exposure" in the present invention refers to exposure of the whole body or a part of the body to radiation and includes internal exposure, which is exposure to radiation from the inside of the body by taking a radioactive material in the body, and external exposure, which is exposure to radiation from the outside of the body. Specific examples of the radiation exposure include medical exposure associated with radiation therapy and diagnostic imaging using radiation, occupational exposure associated with handling of a radioactive material and a radiation generator, natural exposure to a naturally occurring radioactive material or cosmic radiation, radiation exposure associated with accidents such as those of nuclear power plants, and the like, but the radiation exposure includes any of such radiation exposure.

The "radiation damage" in the present invention refers to damage caused by radiation exposure of the whole body or a part of the body. Usually, the radiation damage is a phenomenon that occurs as an undesirable response when normal cells or normal tissue are exposed to radiation, that is to say, an adverse event or a side effect.

The radiation damage including local radiation damage by irradiation on medical purposes such as cancer treatment includes early (acute) radiation damage and delayed (chronic) radiation damage.

The radiation damage in the present invention is not particularly limited, as long as it is a radiation-induced pathological condition caused by radiation exposure.

Specific examples of the radiation damage include radiation epithelitis, radiation esophagitis, radiation nephritis, actinoneuritis, radiation gastritis, radiation necrosis, radiation-induced ulcer, radiation burn, radiation hepatitis, radiation stomatitis, radiation myelopathy, radiation fibrosis, radiation enteritis, radiation dermatitis, radiation mucositis, radiation pneumonitis, radiation dermatitis, radiation cystitis, radiation cataract, radiation leukopenia, radiation-induced emesis, radiation anemia, radiation-induced infertility, and the like.

The "early radiation damage" in the present invention refers to radiation damage that develops in the period from immediately after radiation exposure to several months after radiation exposure. Examples of the early radiation damage in radiation enteritis include, but are not limited to, skin disorder, oral mucosal disorder, gastrointestinal mucosal disorder, hair loss, emesis, eating disorder, mucosal inflammation, hemorrhage, diarrhea, constipation, hematochezia, and the like.

The "delayed radiation damage" in the present invention refers to radiation damage that develops in the period from several months to several decades after radiation exposure. Examples of the delayed radiation damage in radiation enteritis include, but are not limited to, intestinal fibrosis, gastroduodenal ulcer, stenosis, occlusion, fistula formation, hemorrhage, perforation, ulceration, fecal incontinence, chronic diarrhea, and the like.

Organs in which the radiation damage develops in the present invention are organs including any tissue that develops the radiation damage, such as the skin, the brain, the oral cavity, the pharynx, the esophagus, the stomach, the duodenum, the small intestine (the jejunum and the ileum), the large intestine (the appendix, the colon, and the rectum), the anus, the liver, the bile duct, the gallbladder, the pancreas, the kidney, the bladder, the peritoneum, the parotid gland, the submandibular gland, the parotid gland, the lymphatic vessel, the lymph node, the nervous system, the spinal cord, the lung, the respiratory tract, the bronchus, the heart, and the blood vessel.

The "radiation therapy" or the "radiotherapy" in the present invention refers to suppressing the proliferation of cancer cells with intensively irradiating a tumor with a therapeutic dose of radiation while reducing irradiation of normal tissue around the tumor with the therapeutic dose of radiation to radically cure the cancer or mitigate symptoms.

Examples of the cancer to be treated by the "radiation therapy" or the "radiotherapy" or "the treatment of cancer" in the present invention include, but are not limited to, gastrointestinal cancers such as small intestinal cancer, colorectal cancer, gastrointestinal stromal tumor (GIST), gastrointestinal carcinoid, gastric cancer, and esophageal cancer; cancers that occur near the intestine, such as liver cancer, gallbladder/biliary cancer, pancreatic cancer, pancreatic/gastrointestinal neuroendocrine tumor and Langerhans cell histiocytosis, renal cell cancer, renal pelvic/ureteral cancer, and adrenal tumor; pelvic cancers such as bladder cancer, urethral cancer, prostate cancer, testicular tumor, penile cancer, endometrial cancer, cervical cancer, uterine tumor, ovarian tumor, and female genital cancer; cancers that occur in the chest, such as lung cancer, thymic tumor, mesothelioma, and breast cancer; myeloid cancers such as hematopoietic tumor, leukemia, a myeloproliferative disease, and multiple myeloma; osteosarcoma, soft tissue sarcoma, and malignant lymphoma that occur near the intestine; and the like.

Examples of the radiation therapy or radiotherapy in the present invention include external irradiation, in which the body is irradiated from the outside thereof, and internal irradiation, in which the body is irradiated from the inside thereof. Examples of the radiation used in the external irradiation include electromagnetic radiation with a short wavelength (X-ray, γ-ray), proton beam, and heavy ion radiation. Examples of the radiation used in the internal irradiation include X-ray, γ-ray, proton beam, heavy ion radiation, α-ray, and β-ray, and the like. Preferable radiations used in the radiation therapy or radiotherapy in the present invention are γ-ray and X-ray, which are electromagnetic radiations with a short wavelength.

The "tolerance dose" in the present invention refers to the radiation dose that, when a normal tissue is irradiated, the tissue can endure and the minimal tolerance dose (TD5/5) and the maximal tolerance dose (TD50/5) are used clinically. The minimal tolerance dose refers to a total radiation dose with which tissue functional disorder develops at 5% chance within 5 years after irradiation. The maximal tolerance dose refers to a total radiation dose with which tissue functional disorder develops at 50% chance within 5 years after irradiation. The tolerance dose varies depending on the radiation dose per irradiation event or the tissue irradiated, but the definitions of the minimal tolerance dose and the maximal tolerance dose of each tissue are defined, for example, by reference of the known guidelines "Hoshasen Chiryo Keikaku Gaidorain 2012 (Guidelines for radiotherapy treatment planning 2012) (in Japanese)" (Japanese Society for Radiation Oncology) (Table 1).

The "eosinophil-removing agent" in the present invention may be any agent, as long as it can suppress the activation of eosinophils such as cell proliferation, migration, infiltration, and/or degranulation or induce apoptosis and/or cellular injury of eosinophils and may be any of those that acting on an antigen such as receptors and adhesion molecules expressed on the cell surface of eosinophils and those that act on a ligand of the antigen.

Examples of the antigen expressed on the cell surface of eosinophils include the IL-5 receptor (hereinafter, also referred to as "IL-5R"), CRTH2 (PTGDR2, prostaglandin D2 receptor 2, GPR44), Siglec8 (SAF-2), CCR3 (chemokine, CC-motif receptor 3, eotaxin receptor, CD193), and the like. Moreover, examples of the ligand that binds to the antigen include an IL-5 ligand (also merely referred to as "IL-5"), PGD2 (prostaglandin D2), a Siglec8 ligand (sialic acid, 6'-sulfo-sialyl Lewis X, or a ligand containing the sugar chain), and CCL11 (chemokine CC-motif ligand 11, eotaxin), CCL5, CCL7, CCL13, CCL15, CCL24, CCL26, and CCL28, and the like.

TABLE 1

| | | TD5/5 (Gy) (Dose leading to side effect within 5 years at 5% chance) | | | TD50/5(Gy) (Dose leading to side effect within 5 years at 50% chance) | | | |
|---|---|---|---|---|---|---|---|---|
| | Volume | 1/3 | 2/3 | 3/3 | 1/3 | 2/3 | 3/3 | Criteria |
| Bone | Femoral head | — | | 52 | — | | 65 | Necrosis |
| | Temporomandibular joint | 65 | 60 | | 77 | 72 | | Significant trismus |
| | Rib | 50 | — | | 65 | — | | Pathologic fracture |
| Skin | | 10 cm² | 30 cm² | 100 cm² | 10 cm² | 30 cm² | 100 cm² | Telangiectasia |
| | | | — | 50 | | — | 65 | |
| | | 70 | 60 | 55 | | | 70 | Necrosis, ulcer |
| Brain/ nerve | Brain | 60 | 50 | 45 | 75 | 65 | 60 | Necrosis, ulcer |
| | Brainstem | 60 | 53 | 50 | — | | 65 | Necrosis, ulcer |
| | Optic nerve | 50 (No volume effect) | | | — | | 65 | Visual loss |
| | Optic chiasm | 50 (No volume effect) | | | 65 (No volume effect) | | | Visual loss |
| | Spinal cord | 5 cm | 10 cm | 20 cm | 5 cm | 10 cm | 20 cm | Myelitis, necrosis |
| | | | 50 | 47 | | 70 | — | |
| | Nerve of cauda equina | 60 (No volume effect) | | | 75 (No volume effect) | | | Clinically apparent nerve damage |
| | Brachial plexus | 62 | 61 | 60 | 77 | 76 | 75 | Clinically apparent nerve damage |
| | Lens | 10 (No volume effect) | | | — | | 18 | Cataract needing operation |
| | Retina | 45 (No volume effect) | | | — | | 65 | Visual loss |
| Head and neck | Middle ear/ external ear | | 30 | 30* | | 40 | 40* | Acute otitis media with effusion |
| | | | 55 | 55* | | 65 | 65* | Chronic otitis media with effusion |
| | Parotid gland | — | 32* | | — | 46* | | Dry mouth |
| | Larynx | 79* | 70* | | 90* | 80* | | Necrosis of cartilage |
| | | — | 45 | 45* | — | | 80* | Laryngeal edema |
| Chest | Lung | 45 | 30 | 17.5 | 65 | 40 | 24.5 | Pneumonia |
| | Heart | 60 | 45 | 40 | 70 | 55 | 50 | Pericarditis |
| | Esophagus | 60 | 58 | 55 | 72 | 70 | 68 | Clinical stenosis, perforation |
| Abdomen | Stomach | 60 | 55 | 50 | 70 | 67 | 65 | Ulcer, perforation |
| | Small intestine | 50 | | 40* | 60 | | 55 | Occlusion, perforation, fistula |
| | Large intestine | 55 | | 45 | 65 | | 55 | Occlusion, perforation, ulcer, fistula |
| | Rectum | No volume effect at 100 cm³ | | 60 | No volume effect at 100 cm³ | | 80 | Severe proctitis, necrosis, fistula, stenosis |
| | Liver | 50 | 35 | 30 | 55 | 45 | 40 | Liver failure |
| | Kidney | 50 | 30 | 23 | — | 40* | 28 | Clinical nephritis |
| | Bladder | — | 80 | 65 | — | 85 | 80 | Symptomatic bladder atrophy/volume decrease |

*No apparent change at 50% or less volumes

Preferable examples of the eosinophil-removing agent in the present invention include those that bind to at least any one of IL-5R, CRTH2, Siglec8, and CCR3, and the ligands thereof to reduce the activity of eosinophils. More preferable examples of the eosinophil-removing agent include those that bind to at least any one of IL-5R, CRTH2, Siglec8, and CCR3, the ligands thereof and have inhibitory activity on activation of eosinophils such as cell proliferation, migration, infiltration and/or degranulation (also referred to as neutralization activity or antagonist activity) and/or have the apoptosis-inducing activity and/or cellular injury-inducing activity towards eosinophils (also referred to as cytotoxic activity).

Most preferable examples of the eosinophil-removing agent in the present invention include those that bind to at least any one of IL-5R, CRTH2, Siglec8, and CCR3 and have activity that suppresses activation (also referred to as neutralization activity or antagonist activity) of the cell proliferation, migration, infiltration, degranulation of eosinophils, and/or the like and/or have the apoptosis-inducing activity and/or cellular injury-inducing activity (also referred to as cytotoxic activity) of eosinophils.

The eosinophil-removing agent used in the present invention may be either a low molecular weight molecule or a high molecular weight molecule, as long as it has the aforementioned characteristics. Preferable examples thereof include an antibody and a fragment of the antibody.

The "IL-5R" consists of 2 polypeptide chains, the α chain (hereinafter, also referred to as "IL-5Rα chain") and the β chain (hereinafter, also referred to as "IL-5R β chain"). The IL-5Rα chain is responsible for the binding with IL-5 and the single IL-5R β chain does not have binding capacity to IL-5. Therefore, an antibody that binds to the IL-5Rα chain is a more preferable anti-IL-5R antibody used in the present invention.

Examples of the antibody that inhibits the binding of IL-5R and IL-5 include an antibody that binds to the IL-5R and inhibits the binding of IL-5 and IL-5R (anti-IL-5R antibody), an antibody that binds to IL-5 and inhibits the binding of IL-5R and IL-5 (an anti-IL-5 antibody), and the like and more preferable examples thereof include an antibody that inhibits the signal of IL-5R as a result of inhibiting the binding of IL-5R and IL-5. Examples of the anti-IL-5R antibody include the anti-human IL-5Rα antibody Benralizumab. Examples of the anti-human IL-5 antibody include the humanized anti-human IL-5 antibody Mepolizumab (IgG1) and the anti-human IL-5 antibody Reslizumab (IgG4/κ).

The anti-IL-5R antibody that acts directly on IL-5R-expressing cells and inhibits an IL-5R-dependent signal is a more preferred anti-IL-5R antibody, since it can cause the cell proliferation inhibition, the migration inhibition, and/or the apoptotic induction of IL-5R-expressing cells, as well as it can eliminate IL-5R-expressing cells by the effector activity such as the antibody-dependent cellular cytotoxicity activity (ADCC activity).

An antibody involved in the binding of IL-5R and IL-5 whose epitope is the "extracellular region" of IL-5R is a preferable anti-IL-5R antibody used in the present invention. Examples of such an epitope include an epitope present in the 1st to 313rd positions in the amino acid sequence of the extracellular region (the N-terminal region, other than the region from the transmembrane region to the C-terminal in the human IL-5Rα) of human IL-5Rα, an epitope present in the 41st to 61st positions in the amino acid sequence of the extracellular region of human IL-5Rα, an epitope present in the 52nd to 61st positions in the amino acid sequence of the extracellular region of human IL-5Rα, an epitope containing the 61st amino acid residue in the extracellular region of human IL-5Rα, and an epitope to which the anti-human IL-5Rα antibody Benralizumab binds (Kolbeck et al, J. Allergy Clin. Immunol., 2010, 125:1344-1353).

Examples of the IL-5R antibody in the present invention include, but are not limited to, Benralizumab, an antibody that binds to the same epitope as Benralizumab, an antibody containing a CDR of Benralizumab, an antibody including a heavy chain variable region (VH) and a light chain variable region (VL) of Benralizumab, and the like.

More specifically, the anti-IL-5R antibody or anti-IL-5 antibody used in the present invention include an anti-IL-SR antibody comprising heavy chain (H chain) CDRs 1 to 3 respectively comprising the amino acid sequences of SEQ ID NOs: 1 to 3 and light chain (L chain) CDRs 1 to 3 respectively comprising the amino acid sequences of SEQ ID NOs: 4 to 6, an anti-IL-5R antibody comprising VH comprising the amino acid sequence of SEQ ID NO: 7 and VL comprising the amino acid sequence of SEQ ID NO: 8, an anti-IL-5R antibody comprising an H chain comprising the amino acid sequence of SEQ ID NO: 9 and an L chain comprising the amino acid sequence of SEQ ID NO: 10, an antibody comprising CDRs of Benralizumab, an antibody comprising VH and VL of Benralizumab, an antibody comprising a CDR of Mepolizumab (IgG1), an antibody comprising CDRs of Reslizumab (IgG4/κ), an antibody comprising VH and VL of Mepolizumab (IgG1), an antibody comprising VH and VL of Reslizumab (IgG4/κ), Benralizumab, Mepolizumab (IgG1), Reslizumab (IgG4/κ), and the like.

Moreover, more specific examples of the anti-IL-5R antibody used in the present invention also include an anti-IL-5R antibody comprising heavy chain (H chain) CDRs 1 to 3 contained in the amino acid sequence of SEQ ID NO: 14 and light chain (L chain) CDRs 1 to 3 contained in the amino acid sequence of SEQ ID NO: 17, and an anti-IL-5R α antibody comprising VH comprising the amino acid sequence of SEQ ID NO: 14 and VL comprising the amino acid sequence of SEQ ID NO: 17.

Moreover, an antibody in which the core fucose that binds to the 297th in the Fc region in the aforementioned antibody is decreased or deleted is preferable. Specific examples include the humanized anti-IL-5R antibody Benralizumab.

Moreover, the present invention includes an anti-IL-5R antibody comprising heavy chain (H chain) CDRs 1 to 3 contained in the amino acid sequence of SEQ ID NO: 14 and light chain (L chain) CDRs 1 to 3 contained in the amino acid sequence of SEQ ID NO: 17, and an anti-IL-5R antibody comprising VH comprising the amino acid sequence of SEQ ID NO: 14 and VL comprising the amino acid sequence of SEQ ID NO: 17. The antibodies according to the present invention also include any of a monoclonal antibody, a genetically recombined rat antibody, a rat-mouse chimeric antibody, a rat-human chimeric antibody, a humanized antibody, and a human antibody.

"CRTH2" is a seven transmembrane G-protein-coupled receptor for prostaglandin D2 (hereinafter, also referred to as "PGD2"), which is involved in migration of leukocytes and strongly expressed in eosinophils. CRTH2 transmits CRTH2-dependent intracellular signals by binding with PGD2 and induces changes in cell morphology accompanying the migration of CRTH2-expressing cells, increase in cytokine production from the cells, and changes in the cell diameter, the cell surface area, and the like.

A preferable anti-CRTH2 antibody used in the present invention is an antibody that binds to an extracellular region of CRTH2 as its epitope. Examples of the extracellular region of human CRTH2 include an N-terminal region comprising the 1st to 33rd amino acid residues from the N-terminal of human CRTH2, Loop 1 region comprising the 95th to 111st amino acid residues, Loop 2 region comprising the 169th to 206th amino acid residues, and Loop 3 region comprising the 264th to 285th amino acid residues (J Immunol, 1999.162 (3): 1278-86.). The anti-CRTH2 antibody directly acts on CRTH2-expressing cells and can cause the cell proliferation inhibition, the migration inhibition, and/or the apoptotic induction of CRTH2-expressing cells, as a result of inhibiting CRTH2-dependent signals, as well as CRTH2-expressing cells can be eliminated by the effector activity such as the antibody-dependent cellular cytotoxicity activity (ADCC activity). Examples of the antibody to human CRTH2 include 301108 (R & D Systems), BM16 (International Publication No. WO 97/46677), Clone 19A2, 8B1, 31A5 (International Publication No. WO 2014/144865), and Clone Lym2 (International Publication No. WO 2017/010567).

The "Siglec8" is a type I transmembrane protein and strongly expressed in eosinophils. Siglec8 transmits Siglec8-dependent intracellular signals and induces apoptosis of Siglec8-expressing cells.

A preferable anti-human Siglec8 antibody used in the present invention is an antibody that can eliminate Siglec8-expressing cells by the effector activity such as the antibody-dependent cellular cytotoxicity activity (ADCC activity), as well as causes the cell proliferation inhibition and the induction of apoptosis of Siglec8-expressing cells as a result of directly acting on Siglec8 expressing-cells to transmit Siglec8-dependent intracellular signals. Examples of the antibody that binds to human Siglec8 include 837535 (R & D Systems), 7C9 (J Immunol. 2014 Jun. 15, 192 (12): 5481-9), and the like.

The "CCR3" is a seven transmembrane G-protein-coupled receptor and strongly expressed in eosinophils. The migration of eosinophils is induced by the binding of a chemokine such as CCL5, CCL7, CCL11, CCL13, CCL15, CCL24, CCL26, and CCL28 to CCR3.

Examples of the eosinophil-removing agent that binds to CCR3 used in the present invention include an anti-CCR3 antibody and a low molecular weight molecule having CCR3 inhibitory activity. Preferable anti-CCR3 antibody is an anti-CCR3 antibody that directly acts on CCR3-expressing cells and inhibits the binding of chemokines and the migration of eosinophils induced thereby. Examples of the antibody that binds to CCR3 include the 83103 antibody (R & D systems), the 61828 antibody (R & D systems), and the like. Moreover, examples of the low molecular weight molecule having CCR3 inhibitory activity include AXP-1275 and MT-0814.

Examples of the eosinophil-removing agent that binds to a ligand of CCR3 used in the present invention include an antibody that selectively binds to a ligand of CCR3. Preferable antibody that selectively binds to a ligand of CCR3 is an antibody that binds to a ligand of CCR3 and inhibits the binding to CCR3 and the migration of eosinophils induced thereby. Examples thereof include the anti-eotaxin-1 antibodies CAT-212 and CAT213 (J. Pharmacol. Exp. Ther. 2006, 319 (3), 1395-1404), an anti-CCL24 antibody (US20160368979A1), and the like.

The antibody used in the present invention may be either of a monoclonal antibody and a polyclonal antibody, but is preferably a monoclonal antibody that binds to a single epitope. The monoclonal antibody may be a monoclonal antibody produced by hybridoma or a genetically modified antibody produced by a genetically modified technique.

Preferable antibody used in the present invention is a genetically modified antibody, such as an antibody containing a human Fc region, an antibody containing a human constant region, a human chimeric antibody (hereinafter, also referred to as merely "chimeric antibody"), a humanized antibody (also referred to as "human complementarity determining region (CDR)-graft antibody"), and a human antibody, to reduce immunogenicity in humans.

The chimeric antibody is an antibody consisting of a heavy chain variable region (hereinafter, abbreviated as "VH") and a light chain variable region (hereinafter, abbreviated as "VL") of an antibody of an animal other than humans and a heavy chain constant region (hereinafter, abbreviated as "CH") and a light chain constant region (hereinafter, abbreviated as "CL") of a human antibody. The species of the animal for the variable region is not particularly limited, as long as it is an animal from which hybridoma can be produced such as a mouse, a rat, a hamster, and a rabbit.

The human chimeric antibody can be produced by obtaining cDNAs encoding VH and VL of an antibody from an animal other than humans that specifically binds to an antigen of interest, inserting the cDNAs into an expression vector having genes encoding CH and CL of a human antibody to construct a human chimeric antibody expression vector, and introducing the vector into an animal cell and expressing the genes.

The CH of the human chimeric antibody is not particularly limited, as long as it is human immunoglobulin (hereinafter, abbreviated as hIg), but the hIgG class of antibody is preferred. The CL of the human chimeric antibody is not particularly limited, as long as it belongs to hIgG.

The humanized antibody is an antibody in which CDRs of VH and VL of an antibody of an animal other than humans are grafted at the appropriate positions in VH and VL of a human antibody. The humanized antibody can be produced by constructing cDNAs encoding variable regions (hereinafter, abbreviated as "V regions") in which CDRs of VH and VL in an antibody from an animal other than humans that specifically bind to an antigen of interest are grafted in frameworks of VH and VL of any human antibody (hereinafter, abbreviated as "FR"), inserting the cDNAs into an expression vector having DNAs encoding CH and CL of a human antibody to construct a humanized antibody expression vector, and introducing the vector into an animal cell and expressing the genes. The amino acid sequences of the FRs of VH and VL of the human antibody are not particularly limited, as long as they are amino acid sequences derived from a human antibody. The CH of the humanized antibody is not particularly limited, as long as it is hIg, but the hIgG class of CH is preferred. The CL of the humanized antibody is not particularly limited, as long as it belongs to hIg.

The antibody fragment used in the present invention refers to a fragment of each of the aforementioned antibodies and examples of the type of the antibody fragment include, but are not limited to, Fab, Fab', F(ab')$_2$, scFv, diabody, dsFv, VHH, an antibody fragment comprising a peptide comprising a CDR and Fc, and the like.

The "Fab" is an antibody fragment of a molecular weight of about 50000 having antigen binding activity among the fragments obtained by treating IgG with papain (a proteolytic enzyme). The Fab of the antibody in the present invention can be produced by treating the antibody according to the present invention with papain or inserting a DNA encoding the Fab of the aforementioned antibody into an expression vector and introducing this vector into a prokaryote or a eukaryote and expressing the DNA.

The "F(ab')₂" is an antibody fragment of a molecular weight of about 100000 having antigen binding activity among the fragments obtained by treating IgG with pepsin (a proteolytic enzyme). The F(ab')₂ of the antibody in the present invention can be produced by treating the antibody according to the present invention with pepsin or binding Fab's by a thioether bond or a disulfide bond.

The "Fab'" is an antibody fragment of a molecular weight of about 50000 having antigen binding activity, digested at the disulfide bond in the hinge region of F(ab')₂. The Fab' of the antibody in the present invention can be produced by treating the F(ab')₂ of the antibody according to the present invention with dithiothreitol, or inserting a DNA encoding a Fab' of the aforementioned antibody in an expression vector, and introducing this vector into a prokaryote or a eukaryote and expressing the DNA.

The "scFv" is an antibody fragment having antigen binding activity in which one VH and one VL are linked with an appropriate peptide linker. The scFv of the antibody in the present invention can be produced by obtaining cDNAs encoding VH and VL of the antibody according to the present invention, constructing a DNA encoding scFv, inserting this DNA into an expression vector, and introducing this expression vector into a prokaryote or a eukaryote and expressing the DNA.

The "diabody" is an antibody fragment having divalent antigen binding activity in which scFvs are dimerized. The diabody of the antibody in the present invention can be produced by obtaining cDNAs encoding VH and VL in the antibody according to the present invention, constructing a DNA encoding diabody, inserting this DNA into an expression vector, and introducing this expression vector into a prokaryote or a eukaryote and expressing the DNA.

The "dsFv" is an antibody fragment in which polypeptides having substitution of 1 amino acid residue each in VH and VL with a cysteine residue are linked via a disulfide bond between the cysteine residues. The dsFv of the antibody in the present invention can be produced by obtaining cDNAs encoding VH and VL in the antibody according to the present invention, constructing a DNA encoding dsFv, inserting this DNA into an expression vector, and introducing this expression vector into a prokaryote or a eukaryote and expressing the DNA.

The "peptide comprising a CDR" is a peptide comprising at least one or more regions of the CDRs in VH or VL. The peptide comprising one or more CDRs of the antibody in the present invention can be produced by constructing a DNA encoding one or more CDRs of the VH and VL of the antibody according to the present invention, inserting this DNA into an expression vector, and introducing this expression vector into a prokaryote or a eukaryote and expressing the DNA. Moreover, the peptide comprising one or more CDRs of the antibody in the present invention can also be produced by methods of chemical synthesis such as the fluorenylmethyl oxycarbonyl method (Fmoc method), and the (t-butyloxy carbonyl method). Preferable examples include a peptide comprising the 6 CDRs derived from the antibody according to the present invention.

Examples of the "antibody fragment comprising Fc" include those in which an Fc is fused with the aforementioned antibody fragment or an appropriate part of the partial fragment. Examples thereof include scFv-Fc, (scFv)₂-Fc, and the like.

The antibody used in the therapeutic or prophylactic agent according to the present invention is preferably one having effector activity. The "effector activity" is an activity caused through an Fc region of the antibody and known examples of the effector activity include the antibody-dependent cellular cytotoxicity activity (ADCC activity), the complement-dependent cytotoxicity activity (CDC activity), and the antibody-dependent phagocytosis (ADP activity) of phagocytes such as macrophages or dendritic cells.

Known methods for controlling the effector activity include methods for controlling the amount of fucose (also referred to as core fucose) α1-6 linked to the N-acetylglucosamine (GlcNAc) linked at the reducing terminal of the N-linked complex type sugar chain linked to the 297th asparagine (Asn) in EU index (Kabat et al, Sequence of Proteins of immunological interests, 5th edition, 1991) in the Fc region of the antibody (International Publication No. WO 2005/035586, International Publication No. WO 2002/31140, International Publication No. WO 00/61739) or methods for controlling the activity by modifying one or more amino acid residues in the Fc region in the antibody.

The effector activity of the antibody may be increased or decreased by controlling the content of the core fucose of N-linked complex type sugar chain linked to Fc of the antibody. Examples of the method for decreasing the content of the fucose linked to the N-linked complex type sugar chain linked to Fc of the antibody include a method for obtaining an antibody to which fucose is not linked by expressing an antibody using CHO cells having deletion of the α1,6-fucose transferase gene (fucosyltransferase-8, FUT8). The antibody to which fucose is not linked has high ADCC activity.

Meanwhile, as a method for increasing the content of fucose linked to the N-linked complex type sugar chain linked to Fc of the antibody, an antibody to which fucose is linked can be obtained by expressing an antibody using host cells in which an α1,6-fucose transferase gene is introduced. The antibody to which fucose is linked has ADCC activity lower than antibodies to which fucose is not linked.

Moreover, the ADCC activity or CDC activity can be increased or decreased by modifying an amino acid residue in the Fc region of the antibody. By modifying one or more amino acid residues in the Fc region to increase or decrease the binding activity to FcγR, the ADCC activity can be controlled and by modifying one or more amino acid residues in the Fc region to increases or decrease the binding activity to the complement, the CDC activity can be controlled.

For example, the CDC activity of an antibody can be increased by using the amino acid sequence of the Fc region described in US Patent application publication No. 2007/0148165. Moreover, the ADCC activity or CDC activity can be increased or decreased by the amino acid residue modification described in U.S. Pat. Nos. 6,737,056, 7,297,775, 7,317,091, and International Publication No. WO 2005/070963.

Preferably, the antibody used in the present invention have high ADCC activity or CDC activity, particularly, high ADCC activity due to the aforementioned modification.

Moreover, the antibody used in the present invention is preferably an antibody having 80% or more or 90% or more, preferably 91%, 92%, 93%, 94%, or 95% or more of N-glycoside complex type sugar chains linked to the Fc region of the aforementioned antibody having no fucose linked thereto and more preferably an antibody in which no fucose is linked to the sugar chain. In this way, high ADCC activity can be expected.

The anti-IL-5R antibody used in the present invention and the antibody fragment can be produced in reference to WO1997/10354 and WO2005/35583.

The therapeutic or prophylactic agent of the present invention may be a combination of an eosinophil-removing agent and another therapeutic agent or a method for treatment. For example, the eosinophil-removing agent may be used in combination with a drug therapy using an agent such as a steroid, an antioxidant, an anti-inflammatory drug, a radical scavenger formulation, and an antibiotic, a hyperbaric oxygen therapy, argon plasma coagulation, and surgical resection. In such a combination, the eosinophil-removing agent and another therapeutic agent or method for treatment may be administered or conducted simultaneously or may be administered or conducted sequentially.

The therapeutic or prophylactic agent according to the present invention may be any agent as long as it is a pharmaceutical composition comprising the aforementioned eosinophil-removal antibody as an active ingredient, but the agent is usually preferable to be provided in a pharmaceutical formulation obtained by mixing the agent with one or more pharmaceutically acceptable carriers and formulated by any well-known method in the technical field of pharmaceutics.

Preferably, an aseptic solution in which the therapeutic or prophylactic agent according to the present invention is dissolved in an aqueous carrier such as water or an aqueous solution of sodium chloride, glycine, glucose, human albumin, or the like is used. Moreover, such a solution may contain one or more pharmaceutically acceptable excipients such as a buffering agent and/or an isotonizing agent, for example, sodium acetate, sodium chloride, sodium lactate, potassium chloride, sodium citrate, or the like, to bring the formulated solution close to physiological conditions. Moreover, the solution may be freeze-dried to be stored and dissolved in an appropriate solvent used at the time of use.

The route of administration of the therapeutic or prophylactic agent according to the present invention is preferably the most effective route in the treatment and examples thereof include oral administration or parenteral administration such as intraoral administration, intratracheal administration, intrarectal administration, subcutaneous administration, intramuscular administration, intrathecal administration, and intravenous administration, but it is preferably intrathecal administration or intravenous administration.

Examples of formulations appropriate for oral administration include emulsion, syrup, capsules, tablets, powder, granules, and the like. For example, liquid preparations such as emulsion and syrup may be produced by using excipients such as water, saccharides such as sucrose, sorbitol, and fructose, glycols such as polyethyleneglycol and propylene glycol, oils such as sesame oil, olive oil, and soybean oil, antiseptics such as p-hydroxybenzoate esters, and flavors such as strawberry flavor and peppermint.

The capsules, tablets, powder, or granules may be produced by using a filler such as lactose, glucose, sucrose, or mannitol, a disintegrator such as starch or sodium alginate, a lubricant such as magnesium stearate or talc, a binder such as polyvinyl alcohol, hydroxypropylcellulose, or gelatin, a surfactant such as fatty acid ester, or a plasticizer such as glycerin, as an excipient.

Examples of formulations appropriate for parenteral administration include injections, suppositories, spray, and the like. For example, the injections are prepared using a carrier composed of a salt solution, a glucose solution, or a mixture of both, or the like. The suppositories are prepared using a carrier such as coconut butter, a hydrogenated fat, carboxylic acid, or the like. Moreover, the spray is prepared using a carrier that does not stimulate the antibody itself or the oral and respiratory mucosa of the recipient and allows the antibody dispersed as minute particles to facilitate the absorption.

Specific examples of the carrier include lactose, glycerin, and the like. Formulations such as aerosol, dry powder, and the like are possible depending on the properties of the antibody and the carrier used. Moreover, these non-oral formulations may also contain one or more of the ingredients illustrated as an excipient for oral formulations.

The dose or the dose frequency of the therapeutic or prophylactic agent according to the present invention varies depending on the target therapeutic effect, the mode of administration, the treatment period of time, the age, the body weight, or the like, but the dose is usually 1 µg/kg to 10 mg/kg per day for an adult.

In the method for increasing a tolerance dose according to the present invention, the minimal tolerance dose or the maximal tolerance dose can be increased since radiation therapy can be performed while suppressing radiation damage by suppressing activation of eosinophils, such as cell proliferation, migration, infiltration, and/or degranulation using the eosinophil-removing agent or inducing apoptosis and/or cell injury of eosinophils.

Similarly, the radiation therapy with a radiation dose higher than a tolerance dose according to the present invention refers to radiation therapy with a radiation dose higher than the minimal tolerance dose or the maximal tolerance dose in the case of using no eosinophil-removing agent.

By using the method for prevention or the prophylactic agent according to the present invention, the development of tissue functional disorder within 5 years after irradiation can be kept at 5% chance in radiation therapy with a dose of radiation that is higher than a usual minimal tolerance dose, preferably by 1% or more, 2% or more, 3% or more, 4% or more, 5% or more, 6% or more, 7% or more, 8% or more, 9% or more, 10% or more, 15% or more, 20% or more, 25% or more, 30% or more, 40% or more, 50% or more, 60% or more, or 70% or more. Moreover, by using the method for prevention or the prophylactic agent according to the present invention, the development of tissue functional disorder within 5 years after irradiation can be kept at 50% chance in radiation therapy using a radiation dose that is higher than a usual maximal tolerance dose.

Moreover, by increasing the tolerance dose in radiation therapy, the therapeutic effect in the treatment of the lesion can be provided continuously and efficiently, while lowering the effect on normal tissue as much as possible.

The present invention encompasses a method for extending, in a radiation therapy, the period of time of the radiation therapy or a method for increasing the number of irradiation events. The cessation of radiation therapy or postponement of radiation therapy by radiation damage can be avoided by delaying radiation damage that can occur with radiation therapy by suppressing the activation of eosinophils, such as cell proliferation, migration, infiltration, and/or degranulation or inducing apoptosis and/or cell injury of eosinophils by using an eosinophil-removing agent in the present invention. In this way, radiation therapies for patients can be performed continuously while keeping radiation damage associated with radiation exposure suppressed and reduced.

The present invention encompasses a method for treating or preventing radiation damage associated with radiation exposure using an eosinophil-removing agent. The method for treatment or prevention according to the present invention is characterized by administering an eosinophil-removing agent and radiation damage associated with radiation exposure can be treated or prevented by suppressing the inflammatory or fibrosis response in the organ or tissue in which radiation damage has occurred by suppressing the activation of eosinophils, such as cell proliferation, migration, infiltration, and/or degranulation or inducing apoptosis and/or cell injury of eosinophils by using an eosinophil-removing agent.

The present invention encompasses a method for treating cancer, comprising combined use of an eosinophil-removing agent and irradiation. By suppressing the activation of eosinophils, such as cell proliferation, migration, infiltration, and/or degranulation or inducing apoptosis and/or cell injury of eosinophils by using an eosinophil-removing agent in the present invention, radiation damage is suppressed and irradiation with a high dose of radiation becomes possible. In this way, cancer treatment that is safe and effective can be performed.

The eosinophil-removing agents described above can be used as the eosinophil-removing agent used in the method for treating or preventing radiation damage associated with radiation exposure and either of the usage and the dose may be referred.

In the therapeutic or prophylactic agent and the method for treatment or prevention according to the present invention, use of the eosinophil-removing agent and radiation therapy may be simultaneous or both treatments may be sequential, or they may be conducted alternately.

Hereinafter, the present invention will be described in detail with reference to Examples, but the present invention is not limited by these Examples.

EXAMPLES

Example 1: Production of Anti-Mouse IL-5 Receptor-Expressing Cell (1) Construction of Mouse IL-5Rα Gene Expression pEF6 Vector Mouse IL-5Rα cDNA (SEQ ID NO: 11) was totally synthesized. The mouse IL-5Rα cDNA was inserted to a vector pEF6/myc-His C (Invitrogen Corp.) to construct a mouse IL-5Rα gene expression pEF6 vector.
(2) Production of Expi293F Cell Transiently Expressing Mouse IL-5Rα

Expi293F cells were transfected with the mouse IL-5Ra expression pEF6 vector according to the attached instruction. Then, the cells were cultured for 3 days using Expi293F medium.
(3) Production of Ba/F3 Cell Stably Expressing Mouse IL-5Ra Ba/F3 cells were transfected with the mouse IL-5Ra expression pEF6 vector using Cell Line Nucleofector Kit V (Lonza Group AG) according to the attached instruction.

Drug selection was performed by repeated passage for 3 weeks using RPMI1640 medium supplemented with 10% FBS, a penicillin (100 U/mL)-streptomycin (100 μg/mL) mixed solution (Nacalai Tesque, Inc.), and 0.5 ng/mL mouse IL-5 (Sigma-Aldrich Co. LLC) (hereinafter, also referred to as "IL-5Rα/BaF3 medium"), and 30 μg/mL blasticidin (InvivoGen). The expression of mouse IL-5Rα on the cell membranes was confirmed by flow cytometry using APC anti-IL5RA antibody (Miltenyi Biotec, REA343).

Example 2: Production of Monoclonal Antibody to Anti-Mouse IL-5Rα

(1) Immunization of Rat

A 9-week-old female WKY/NCrlCrlj rat (WKY rat) (Charles River Laboratories Japan, Inc.) was immunized. 25 μg of mouse IL-5Rα-Fc was suspended in 100 μL of physiological saline (Otsuka Pharmaceutical Factory, Inc.) and combined with 100 μL of Sigma Adjuvant System(R) (Sigma-Aldrich Co. LLC) to prepare 200 μL of a suspension. For initial immunization, 100 μL of the suspension per site was intramuscularly administered to two right and left sites at the tail base of the WKY rat. Two weeks after the initial administration, 25 μg of mouse IL-5Rα-Fc was suspended in 200 μL of physiological saline, and the suspension was administered in the same way as above.
(2) Production of Hybridoma Three days after the second immunization in the paragraph (1), the iliac lymph node was surgically excised from the WKY rat and subjected to cell fusion. First, the excised iliac lymph node was ground with a glass slide to loosen tissues. The iliac lymph node tissues were suspended in Minimum Essential Media (MEM) (Invitrogen Corp.) and passed through a cell strainer to remove extra tissues. The supernatant was removed by centrifugation at 1500 rpm for 5 minutes. Then, the pellets were resuspended in MEM to prepare iliac lymph node cells.

Mouse myeloma cells P3-U1 (ATCC) to be subjected to the cell fusion were habituated and cultured in S-Clone Cloning Medium CM-B (Eidia Co., Ltd.) and then used (hereinafter, also referred to as "serum-free habituated P3-U1"). The obtained iliac lymph nodes cells were mixed with the serum-free habituated P3-U1 at a cell number of 1/2. The supernatant was removed by centrifugation. Then, the cells were fused using GenomONE-CF (Ishihara Sangyo Kaisha, Ltd.) according to the attached instruction. Then, the cells were suspended in HAT medium (500 mL of S-Clone Cloning Medium CM-B (Eidia Co., Ltd.) supplemented with 10 mL of a HAT (hypoxanthine (H), aminopterin (A), and thymidine (T)) solution (Thermo Fisher Scientific Inc.) and 0.5 mL of a 10 mg/mL gentamycin solution (Nacalai Tesque, Inc.)), inoculated to a 96-well plate, and cultured.
(3) Hybridoma Screening The hybridomas inoculated in the paragraph (2) were cultured for 7 days. Then, the culture supernatant of each well was collected and analyzed for its reactivity with mouse IL-5Ra. Mouse IL-5Rα-expressing Expi293F cells and Expi293F cells were used as positive control cells and negative control cells, respectively. First, the positive control cells or the negative control cells were inoculated at $1 \times 10^5$ cells/50 μL per well to a 96-well plate, and 50 μL of the culture supernatant was added to each well and reacted at 4° C. for 30 minutes.

The cells were washed with PBS(−). Then, DyLight 650 anti-Rat IgG (Fc) (Abcam plc) diluted 300-fold with 1% (w/v) BSA-PBS(−), pH 7.0 without KCl (Nacalai Tesque, Inc.) supplemented with 0.05% $NaN_3$ and 1 mmol/L EDTA (Nacalai Tesque, Inc.) (hereinafter, also referred to as "FACS buffer 1") was added at 50 μL/well and reacted at 4° C. for 30 minutes. The cells were washed with FACS buffer 1, followed by the analysis of fluorescence intensity using CyAn ADP-HyperCyt (Beckman Coulter, Inc.).

The hybridoma in a well found to have specific reaction with the Expi293F cells transiently expressing mouse IL-5Rα was subjected to single cell cloning once by the limiting dilution method using a cloning medium (S-Clone Cloning Medium CM-B (Eidia Co., Ltd.) supplemented with 0.5 mL of a 10 mg/mL gentamycin solution (Nacalai Tesque, Inc.) and 5 mL of HT supplement (Thermo Fisher Scientific Inc.)). Finally, a hybridoma (hereinafter, also referred to as "1B12") that exhibited strong reactivity, in flow cytometry, with the Ba/F3 cells stably expressing mouse IL-5Rα was established.

(4) Identification of Subclass of Antibody Contained in Culture Supernatant of Hybridoma 1B12

A culture supernatant obtained by the culture of the hybridoma 1B12 for several days was diluted 10-fold with D-PBS, and 150 µL of the dilution was used to analyze a subclass using Rat Monoclonal Antibody Isotyping Test Kit (Bio-Rad AbD Serotec Ltd.) according to the attached instruction.

As a result, the rat anti-mouse IL-5Rα monoclonal antibody (hereinafter, also referred to as "1B12 antibody") contained in the culture supernatant of 1B12 was found to be a rat IgG1 antibody.

(5) Cloning of Heavy Chain and Light Chain Variable Region Genes of 1B12 Antibody Total RNA was prepared from 1B12 using RNeasy Micro Kit (Qiagen N.V.) according to the attached document. cDNA was prepared from purified mRNA using SMARTer RACE 5/3 Kit (Clontech Laboratories, Inc.) according to the attached instruction.

The rat heavy chain gene and the rat light chain (κ chain) gene were each amplified by PCR with the obtained cDNA as a template and analyzed for their nucleotide sequences. The DNA sequences encoding the H chain and L chain variable regions are described in SEQ ID NOs: 12 and 15, the amino acid sequences of VH and VL including a signal sequence are described in SEQ ID NOs: 13 and 16, and the amino acid sequences of VH and VL excluding the signal sequence are described in SEQ ID NOs: 14 and 17.

Example 3: Production of Rat/Mouse Chimera Type 1B12 Antibody (1) Construction of Rat/Mouse Chimera Type 1B12 Antibody expression vector An anti-mouse IL-5Rα rat/mouse chimera type 1B12 antibody expression vector was established by the following method. The gene sequences of the 1B12 antibody heavy chain variable region and light chain variable region analyzed in Example 2-(5) were linked to mouse IgG2a heavy chain and κ chain constant region gene sequences, respectively, to produce artificially synthesized genes, which were then introduced into pCI based vector (Promega Corp.). *E. coli* DH5a competent cells (Takara Bio Inc.) were transformed with the vector, subcloned, and sequenced to produce a rat/mouse chimera type 1B12 antibody (hereinafter, also referred to as "cm1B12 antibody") expression vector.

(2) Creation of Cell Line Transiently Expressing cm1B12 Antibody

In order to produce a line transiently expressing the cm1B12 antibody, the expression vector produced in the paragraph (1) was introduced into host cells using FreeStyle™ MAX CHO Expression System (Life Technologies Corp.) according to the attached instruction. The host cells used were a line of FUT8 knockout CHO cells (International Publication Nos. WO 2005/035586 and WO 02/31140) habituated to FreeStyle™ CHO Expression Medium (Life Technologies Corp.). Antibodies produced by the FUT8 knockout CHO cells are antibodies in which a sugar chain lacking α1,6-fucose is linked to a Fc region, and have higher ADCC activity than that of antibodies having a fucosylated sugar chain.

1 mg of the cm1B12 antibody expression vector was dissolved in 16 mL of Opti-Pro SFM (Invitrogen Corp.), and 1000 µL of Freestyle MAX Reagent (Invitrogen Corp.) was dissolved in 15 mL of Opti-Pro SFM, and these solutions were left at room temperature for 5 minutes. These two solutions were mixed and left at room temperature for 15 minutes. The whole amount of the mixed solution was added to 800 mL of the host cell culture solution ($1\times10^6$ cells/mL) to obtain a cell line transiently expressing the cm1B12 antibody.

(3) Purification of cm1B12 Antibody

The cell line transiently expressing the cm1B12 antibody, obtained in the paragraph (2), was suspended in Free style CHO expression medium (Invitrogen Corp.) supplemented with 8 mM of L-glutamine (Invitrogen Corp.), and cultured for 7 days in an Erlenmeyer flask, then a culture supernatant was harvested. The harvested culture supernatant was centrifuged and filtered through a 0.22 µm filter to prepare a culture supernatant containing the cm1B12 antibody.

The cm1B12 antibody was purified from the prepared culture supernatant using Ab-Capcher ExTRα (ProteNova K.K.). First, a column was loaded with the culture supernatant and washed with D-PBS, followed by elution with an elution buffer of pH 3.0 (0.1 M citric acid monohydrate-NaOH/pH 3.0) in order. The eluted fractions were immediately neutralized with a neutralization buffer (2 M Tris-HCl/pH 8.5).

The absorbance at 280 nm (A280) of each fraction was measured, and continuous fractions having a high measurement value were recovered as antibody fractions. The solvent was replaced with D-PBS using NAP-25 columns Sephadex (GE Healthcare) according to the attached document. A purified protein was obtained through a 0.22 µm filter. Its concentration was calculated with the absorption coefficient at 280 nm defined as 1.61.

Example 4: Antigen-Binding Activity of cm1B12 Antibody (1) Binding to Mouse IL-5Rα-Fc The binding activity of the cm1B12 antibody to mouse IL-5Rα-Fc was analyzed using Biacore T200. Anti-Human IgG (Fc) was immobilized at about 9000 RU onto CM5 sensor chip (GE Healthcare) using Human Antibody Capture Kit (GE Healthcare) according to the attached instruction. Mouse IL-5Rα-Fc (R&D Systems Inc.) dissolved at 1 µg/mL in HBS-EP(+) was captured as a ligand at a flow rate of 30 µL/min for 20 seconds. Then, the cm1B12 antibody serially diluted into concentrations of 1000.00, 333.33, 111.11, 37.04, 12.35, and 4.12 ng/mL was added thereto as an analyte by the multicycle method.

The operation was performed under conditions involving a flow rate of 30 µL/min, and a contact time and a dissociation time of 120 seconds and 600 seconds, respectively. The analysis was carried out using Biacore T200 Evaluation software in the Surface bound and Bivalent Analyte mode.

As a result, as shown in Table 2, the cm1B12 antibody exhibited strong binding activity to mouse IL-5Rα-Fc.

TABLE 2

| $K_D$ (mol/L) | kon (L/mol/sec) | koff (1/sec) |
|---|---|---|
| $3.17 \times 10^{-11}$ | $4.10 \times 10^6$ | $1.26 \times 10^{-4}$ |

(2) Binding to IL-5Rα-Expressing Ba/F3 Cell

Ba/F3 cells or IL-5Rα-expressing Ba/F3 cells were suspended at a cell density of 1×10$^6$ cells/mL in FACS buffer 1. The cell suspension was inoculated at 100 µL/well (5×10$^3$ cells/well) to a 96-well U-form plate. The cm1B12 antibody was diluted into final concentrations of 0.0003, 0.001, 0.003, 0.01, 0.03, 0.1, 0.3, 1, 3, and 10 µg/mL with FACS buffer 1, added at 100 µL/well, and reacted for 1 hour on ice. After washing with FACS buffer 1, Alexa Fluor(R) 647 Goat anti-mouse IgG (H+L) (Life Technologies Corp.) diluted into 5 µg/mL with FACS buffer 1 was added at 100 µL/well and reacted for 1 hour on ice. After washing with FACS buffer 1, the fluorescence intensity (geometric mean) was measured using a flow cytometer Canto II (Becton, Dickinson and Company).

The results are shown in FIG. 1. The cm1B12 antibody specifically bound to the IL-5Rα-expressing Ba/F3 cells in a concentration-dependent manner.

Example 5: Cytotoxic Activity of cm1B12 Antibody to IL-5Rα-Expressing Cell

The cytotoxic activity of the cm1B12 antibody was evaluated by a method described below using human frozen peripheral blood mononuclear cells (PBMC) (AllCells) as effector cells and Ba/F3 cells or mIL-5Rα-expressing Ba/F3 cells as target cells.

The effector cells and the target cells were washed with RPMI 1640 Medium, no phenol red (Nacalai Tesque, Inc.) supplemented with 5% dialyzed FBS, and adjusted to cell densities of 2×10$^7$ cells/mL and 5×10$^3$ cells/mL, respectively. The cm1B12 antibody adjusted to final concentrations of 0.0001, 0.001, 0.01, 0.1, 1, 10, 100 and 1000 ng/mL, the target cells, and the effector cells were added in this order at 50 µL each/well to a 96-well U-bottom plate and reacted at 37° C. for 4 hours.

50 µL of the supernatant was recovered from each well into a 96-well flat-bottom plate (Sumitomo Bakelite Co., Ltd.), and lactate dehydrogenase (LDH) activity in the supernatant was detected using CytoTox 96 Non-Radioactive Cytotoxicity Assay (Promega Corp.) according to the attached instruction. The absorbance was measured at 490 nm using a plate reader SPECTRA MAX 340 PC384 (Molecular Devices, LLC). The cytotoxic activity was calculated according to the following expression using a measurement value corrected with a background.

Cytotoxicity (%)=[[Absorbance of the sample]−[Absorbance of the spontaneous release of LDH from the target cells]−[Absorbance of the spontaneous release of LDH from the effector cells]]/[[Absorbance of the total release of LDH from the target cells]−[Absorbance of the spontaneous release of LDH from the target cells]]

Figure 2:
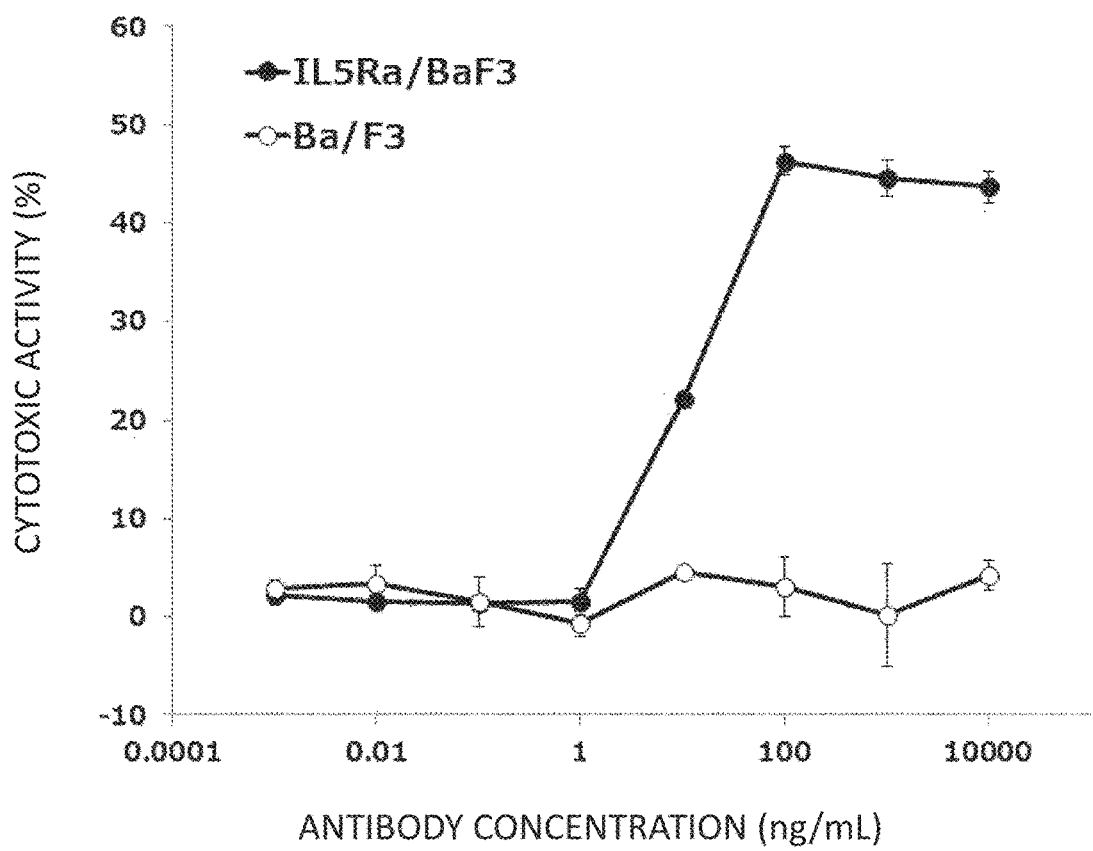
FIG. 2 illustrates the result of analysis of cytotoxic activity of the cm1B12 antibody to IL5Rα-expressing Ba/F3 cells. The filled circle indicates the cytotoxic activity of the cm1B12 antibody to the IL5Rα-expressing Ba/F3 cells and the open circle illustrates the cytotoxic activity of the antibody to the Ba/F3 cells. The ordinate represents the percent cytotoxic activity (%) relative to the maximum cytotoxic activity 100% and the abscissa represents the antibody concentration.

The results are shown in FIG. 2. The cm1B12 antibody exhibited cytotoxic activity to the IL-5Rα-expressing cells in a concentration-dependent manner.

Example 6: Antagonist Activity of cm1B12 Antibody to IL-5-IL-5R Signal (1) Evaluation of IL-5-Dependent Cell Proliferation of IL-5Rα-Expressing Ba/F3

Ba/F3 cells or IL-5Rα-expressing Ba/F3 cells were washed with RPMI1640 medium supplemented with 10% FBS and a penicillin (100 U/mL)-streptomycin (100 µg/mL) mixed solution (Nacalai Tesque, Inc.), and then adjusted to a cell density of 1×10$^5$ cells/mL. The Ba/F3 cells or the IL-5Rα-expressing Ba/F3 cells were inoculated at 50 µL/well to a 96-well flat-bottom plate. Mouse IL-5 (Sigma-Aldrich Co. LLC) adjusted to final concentrations of 0.001, 0.01, 0.1, 1 and 10 ng/mL with the medium was added at 50 µL/well and reacted at 37° C. for 72 hours.

Then, a live cell number was measured using Cell Counting Kit-8 (Dojindo Laboratories) according to the attached instruction. The absorbance was measured at 450 nm using a plate reader SPECTRA MAX 340 PC384 (Molecular Devices, LLC).

Figure 3A:
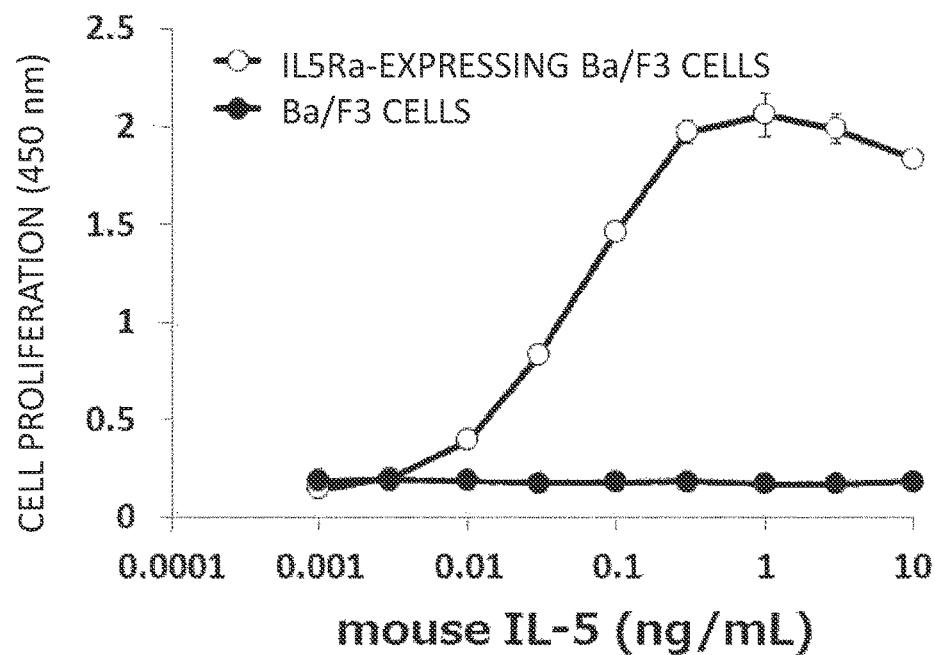
FIG. 3A illustrates the result of analysis of the cell proliferation of Ba/F3 cells and IL5Rα-expressing Ba/F3 cells stimulated with murine IL-5. The ordinate represents the cell proliferation (absorbance OD450) and the abscissa represents the concentration (ng/mL) of murine IL-5.

The results are shown in FIG. 3A. The IL-5Rα-expressing Ba/F3 cells proliferated in an IL-5 concentration-dependent manner.

(2) Antagonist Activity of cm1B12 Antibody to IL-5-IL-5R Signal

The cm1B12 antibody was added at final concentrations of 0.003, 0.01, 0.03, 0.1, 0.3, 1, 3 and 10 µg/mL in the presence of mouse IL-5 (Sigma-Aldrich Co. LLC) having a final concentration of 0.1 ng/mL under the same culture conditions as in the paragraph (1), and a live cell number of IL-5Rα-expressing Ba/F3 cells was measured. Mouse IgG2a purified (BD Pharmingen) was used as a negative control.

The cell proliferation-inhibiting activity was calculated according to the following expression using a measurement value corrected with a background.

Inhibiting activity (%)=100×[1−[[Absorbance of the sample]−[Average absorbance of the IL-5-non-added group]]/[[Average absorbance of the antibody-non-added group]−[Average absorbance of the IL-5-non-added group]]]

Figure 3B:
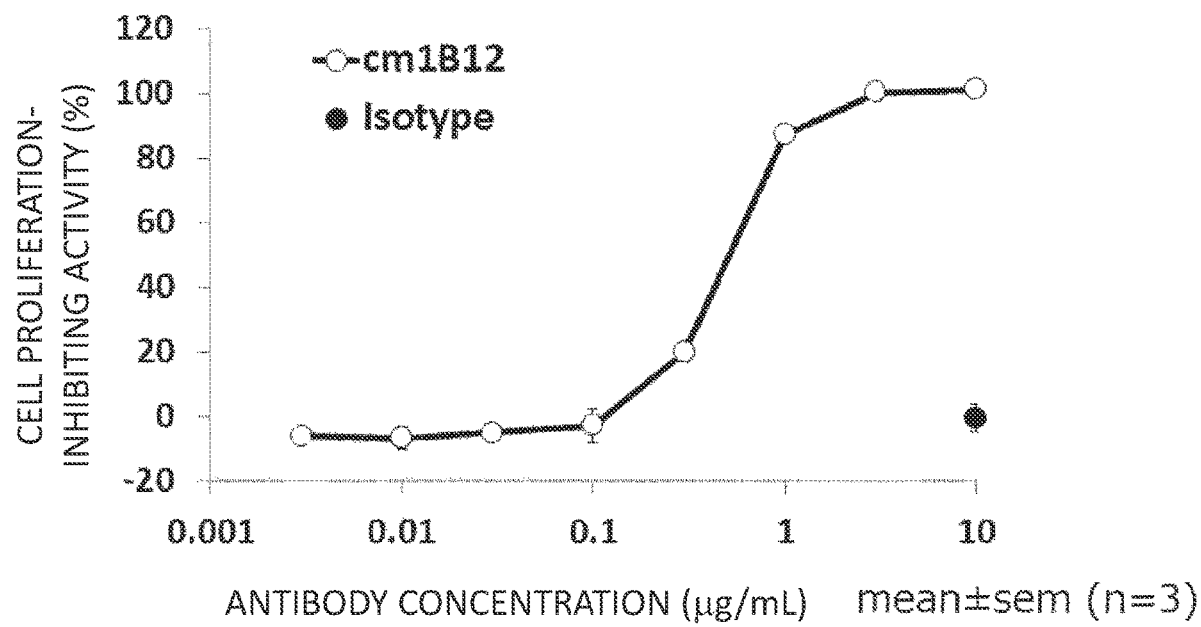
FIG. 3B illustrates the neutralization activity of the cm1B12 antibody to cell proliferation mediated by the binding of murine IL-5 with IL-5R. The ordinate represents the cell proliferation-inhibiting activity (%) and the abscissa represents the antibody concentration (μg/mL).

The results are shown in FIG. 3B. The cm1B12 antibody inhibited cell proliferation in an antibody concentration-dependent manner. The cm1B12 antibody was found to be an IL-5R antagonist antibody inhibiting IL-5-dependent cell proliferation.

Example 7: Eosinophil-Removing Activity of cm1B12 Antibody

In order to test the eosinophil-removing effect of the cm1B12 antibody in vivo, the cm1B12 antibody or an anti-IL-5 ligand rat monoclonal antibody TRFK-5 (R&D Systems Inc.) diluted into 2 mg/mL with D-PBS was intraperitoneally administered at 25 mg/kg to each 8- to 10-week-old BALB/c mouse (female). Blood was collected 1 week, 2 weeks, and 4 weeks after the administration, and the small intestine was collected 4 weeks after the administration, followed by analysis. D-PBS was administered to a control group.

(1) Removing Activity to Eosinophil in Blood (i) Preparation of Cell

Approximately 1 mL of blood was collected from the mouse and mixed with an EDTA-2Na powder. Then, hemolysis treatment was performed by the following method using BD PharmLyse (Becton, Dickinson and Company). The whole amount of the mouse blood was added to 5 mL of 1× Lysis buffer, mixed by inversion, and then reacted at ordinary temperature for 3 minutes. After centrifugation at 2000 rpm at 4° C. for 5 minutes, the supernatant was removed and the cells were resuspended in 1 mL of 1× Lysis buffer and reacted at ordinary temperature for 3 minutes.

After centrifugation at 5000 rpm at 4° C. for 3 minutes, the supernatant was removed. Then, the cells were suspended and washed in 1 mL of D-PBS supplemented with 10% FBS (GIBCO), 10 mM EDTA (Nacalai Tesque, Inc.), 20 mM HEPES (MP Biomedicals), 1 mM sodium pyruvate (GIBCO), 10 μg/mL polymyxin B sulfate (Sigma-Aldrich Co. LLC), and a penicillin (100 U/mL)-streptomycin (100 μg/mL) mixed solution (Nacalai Tesque, Inc.) (hereinafter, also referred to as "FACS buffer 2").

(ii) Measurement

The blood cells prepared in the paragraph (i) were suspended at a cell density of $1\times10^7$ cells/mL in FACS buffer 2 and added at 100 μL/tube to a 1.5 mL microtube. Fc blocker (BD Biosciences, 2.4G2) was added 1 μL/tube and reacted for 15 minutes on ice. Then, FITC anti-CD11b (BD Biosciences, M1/70), PE anti-Siglec F (BD Biosciences, E50-2440), PE-Cy7 anti-CD11c (BD Biosciences, HL3), and APC anti-GR1 (BD Biosciences, RB6-8C5) were added 1 μL each/tube and reacted for 20 minutes on ice. After washing with FACS buffer 2, measurement was performed using FACS Calibur (Becton, Dickinson and Company).

Figure 4A:
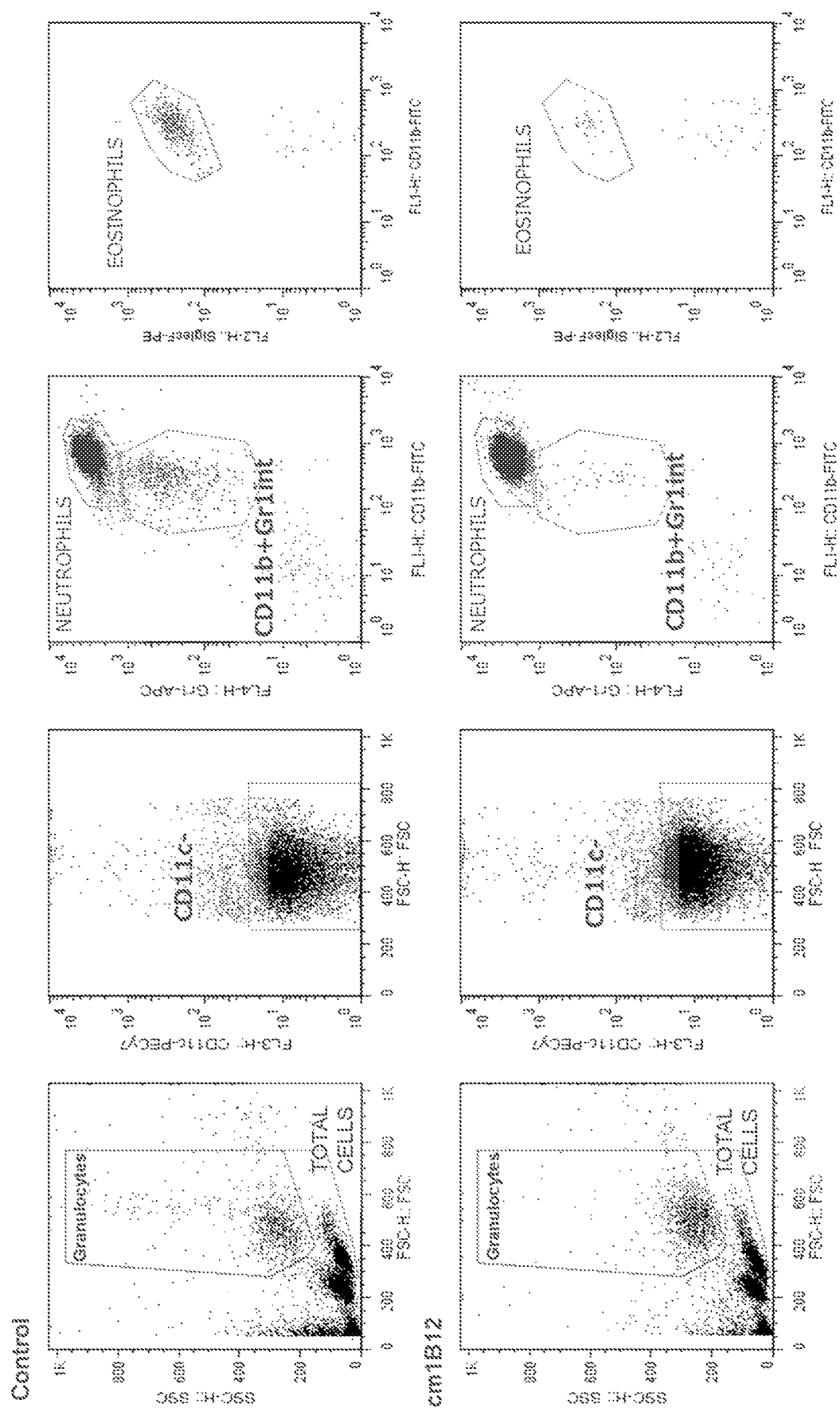
FIG. 4A illustrates the gating of blood eosinophil fraction by flow cytometry.
Figure 4A:
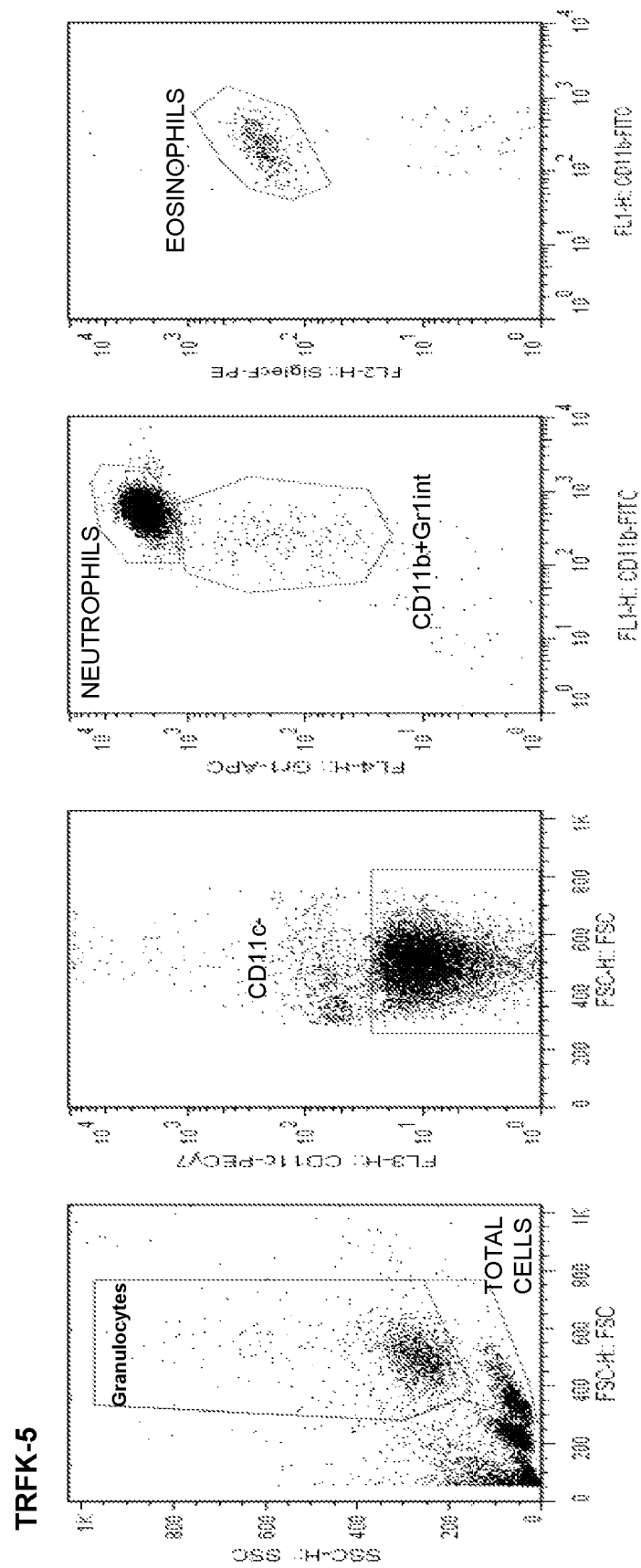

For the analysis, as shown in FIG. 4A, the cells were gated in FSC and SSC. When the total cell number was defined as monocyte and granulocyte fractions, a $CD11c^-/CD11b^+/Gr1^{int}/Siglec\ F^+$ fraction among the granulocyte fractions was regarded as an eosinophil fraction, and the ratio (%) of the eosinophil fraction was calculated. FIG. 4A shows results of analyzing the mouse blood 4 weeks after the administration of each antibody.

As a result, as shown in FIG. 4B, marked decrease in eosinophils fraction in peripheral blood was confirmed in the cm1B12 antibody- and anti-IL-5 antibody TRFK-5-administered groups compared with the control group. The cm1B12 antibody more strongly decreased the eosinophils than the TRFK-5 antibody. Accordingly, the cm1B12 antibody and the TRFK-5 antibody were found to be antibodies capable of decreasing peripheral blood eosinophils.

(2) Removing Activity to Small Intestinal Eosinophil (i) Preparation of Small Intestinal Lamina Propria Cell The mouse was euthanized and then laparotomized, and the small intestine was cut at the pylorus and the ileocecal valve and recovered. Fat tissues and the Peyer's patch attached to the intestinal wall were removed. Then, longitudinal incision was made in the intestine, and the contents were washed off by rinsing in D-PBS. Chopped small intestine pieces were incubated at 37° C. for 20 minutes with stirring in FACS buffer 2. The small intestine pieces were washed with D-PBS, then further finely chopped, and incubated at 37° C. for 60 minutes with stirring in RPMI1640 medium supplemented with 10% FBS (GIBCO), 0.425 mg/mL LibeRase T-flex (F. Hoffmann-La Roche, Ltd.), and 100 μg/mL DNase I (F. Hoffmann-La Roche, Ltd.). Tissue residues were removed through a strainer having a pore size of 100 μm (BD Biosciences). Then, the separated cells were recovered by centrifugation at 1500 rpm at 4° C. for 5 minutes. The cells were further separated by the density gradient centrifugation method using 40% and 75% Percoll solutions (20° C., 20 min, 2000 rpm). The separated cells were suspended and washed in FACS buffer 2.

(ii) Measurement

FACS analysis was conducted in the same way as in the paragraph (1) (ii) using the small intestinal lamina propria cells prepared in the paragraph (i).

Figure 5A:
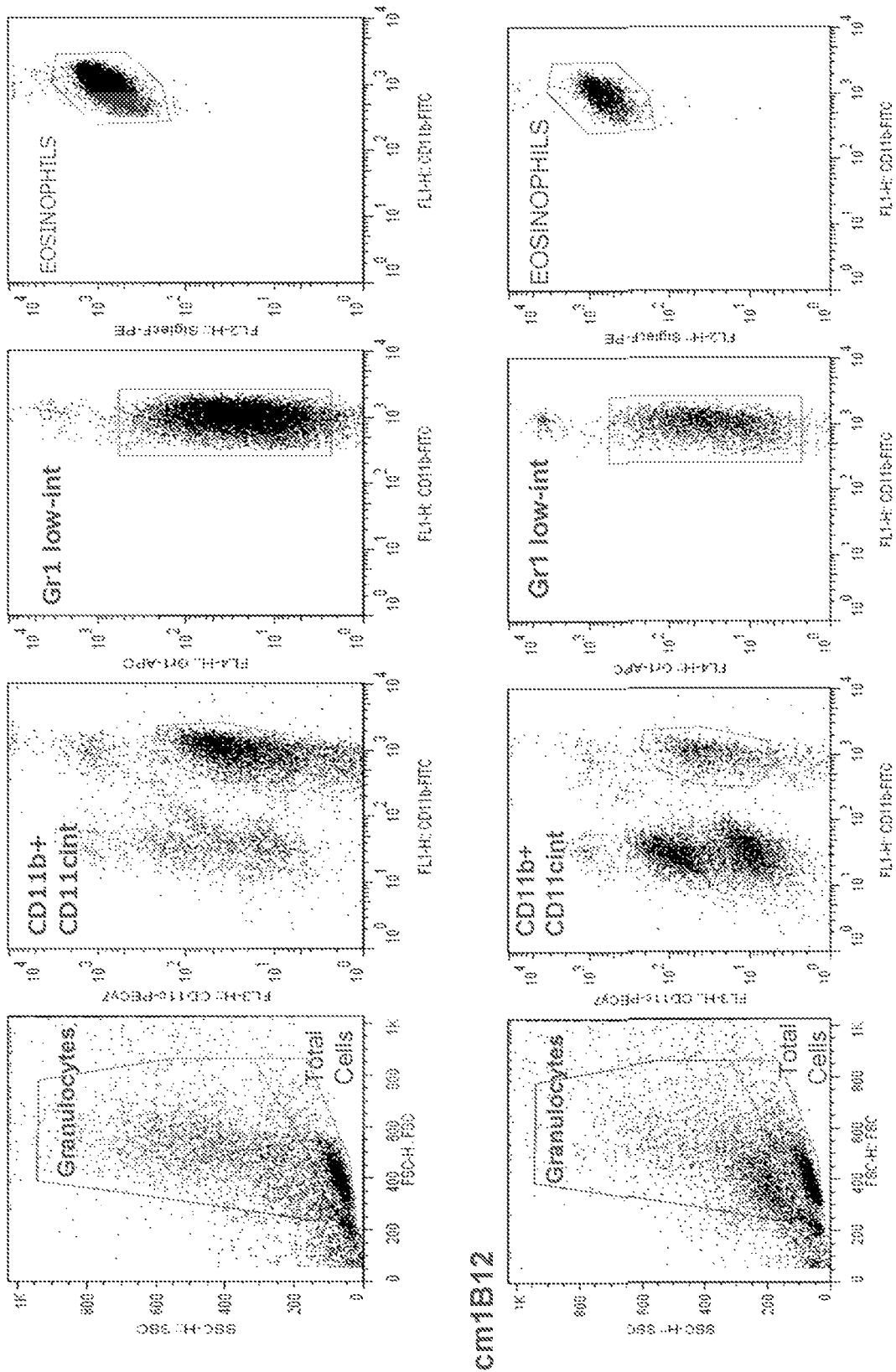
FIG. 5A illustrates the gating of the small intestinal eosinophil fraction by flow cytometry.
Figure 5A:
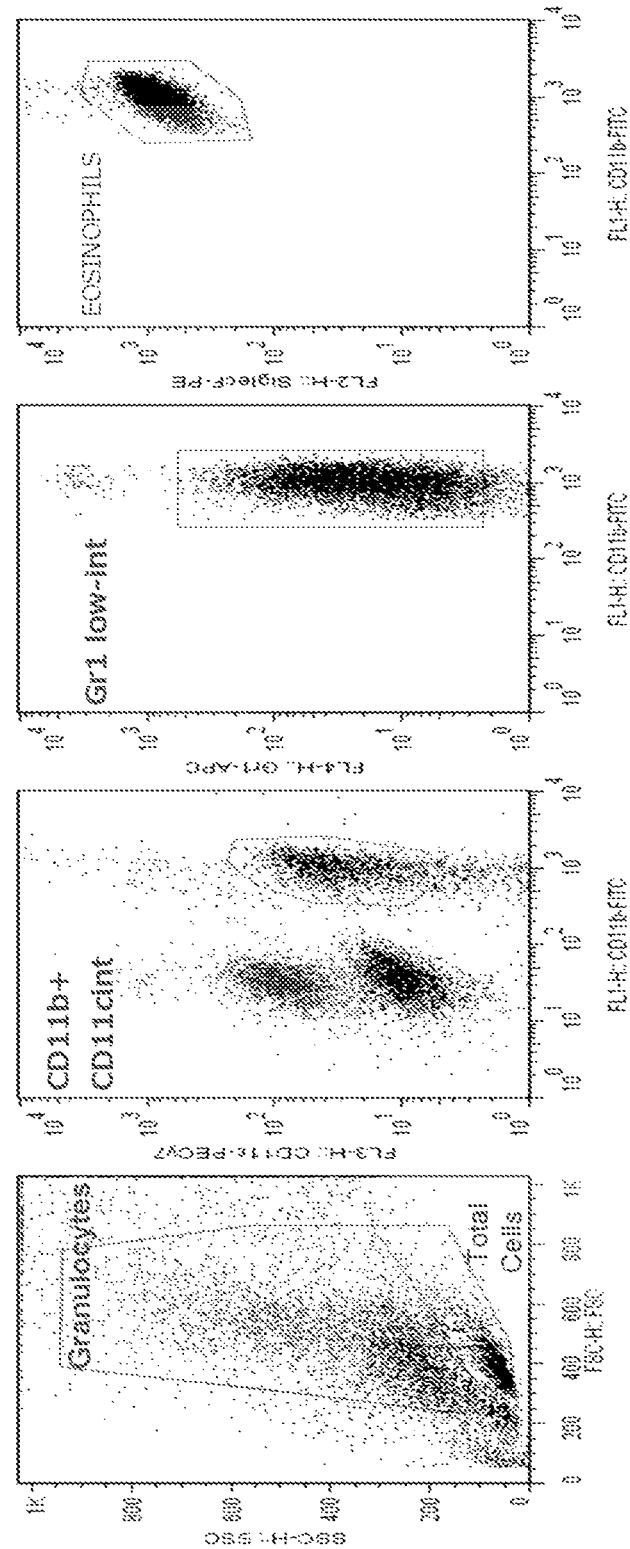

For the analysis, as shown in FIG. 5A, the cells were gated in FSC and SSC. When the total cell number was defined as monocyte and granulocyte fractions, a $CD11c^{int}/CD11b^+/Gr1^{int}/Siglec\ F^+$ fraction among the granulocyte fractions was regarded as an eosinophil fraction, and the ratio (%) of the eosinophil fraction was calculated.

Figure 5B:
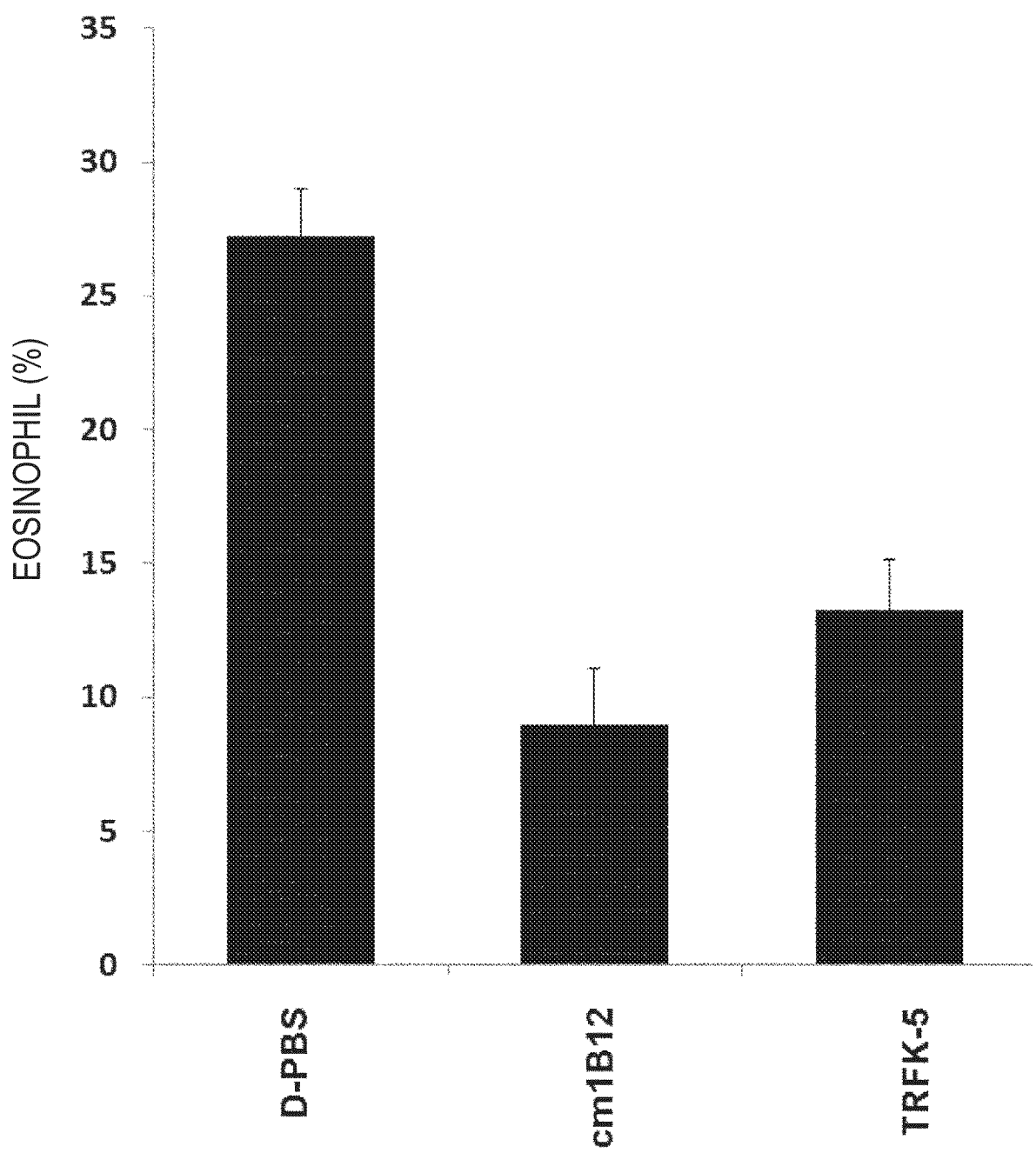
FIG. 5B illustrates the result of analysis of change in the ratio of small intestinal eosinophils by administration of the cm1B12 antibody or the TRFK-5 antibody. The ordinate represents the ratio (%) of the small intestinal eosinophil fraction relative to the fraction defined as the total cell number in FIG. 5A.

As a result, as shown in FIG. 5B, the eosinophil fraction present in the small intestinal lamina propria markedly decreased in the cm1B12 antibody- or anti-IL-5 antibody TRFK-5-administered group compared with the control group 4 weeks after the antibody administration. The cm1B12 antibody more strongly decreased the eosinophils than the TRFK-5 antibody. Thus, the cm1B12 antibody and the TRFK-5 antibody were found to decrease not only eosinophils in peripheral blood but eosinophils present tissue-specifically in the small intestinal lamina propria, etc.

Example 8: Suppressive Effect of cm1B12 Antibody on Radiation Enteritis (Delayed Damage)

(1) Induction of Radiation Enteritis (Delayed Damage)

Each mouse was generally anesthetized with Somnopentyl and then irradiated with 12 Gy of gamma ray with regions other than the abdomen shielded with a lead block (Gammacell 40 Exactor, MDS Nordion Inc.). The mouse thus irradiated was raised by the free ingestion of feed and drinking water.

(2) Pathological Condition Suppressive Effect of cm1B12 Antibody

The cm1B12 antibody or the TRFK-5 antibody diluted into 2 mg/mL with D-PBS was intraperitoneally administered at 25 mg/kg a total of five times on 4-week intervals from 4 weeks before the irradiation to 13 weeks after the irradiation. Thirteen weeks after the irradiation, blood and tissues were collected and analyzed.

(i) Decrease in Eosinophil in Blood

Figure 6A:
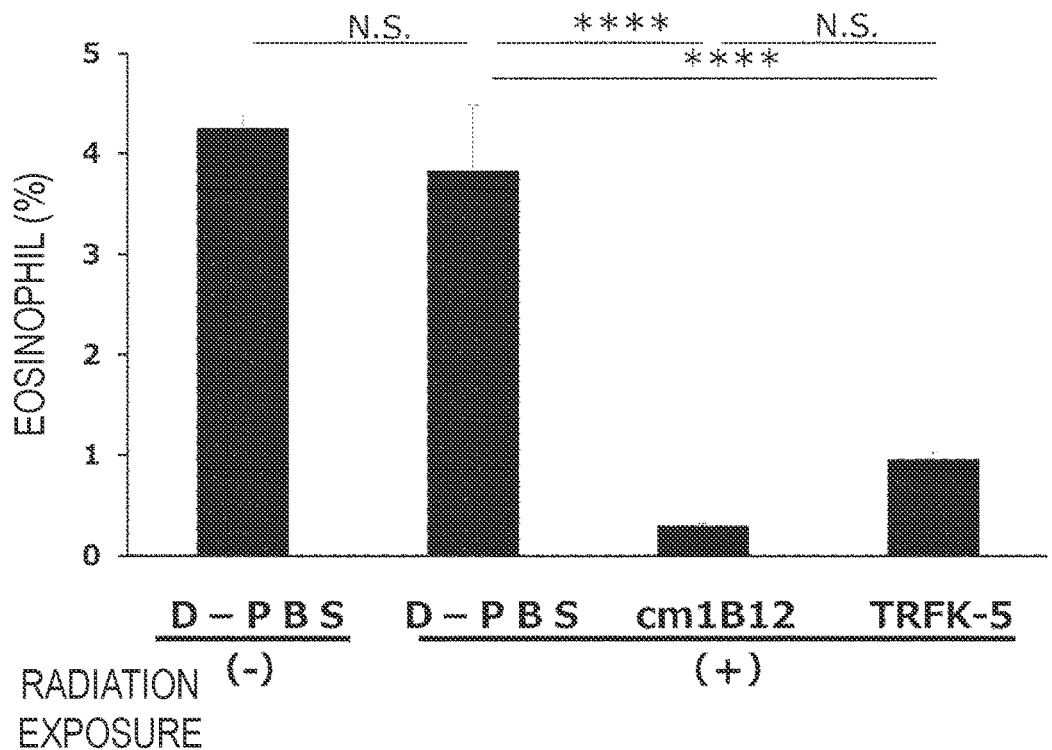
FIG. 6A illustrates the result of analysis of the effect of administration of the cm1B12 antibody or the TRFK-5 antibody on the ratio of blood eosinophils 13 weeks after irradiation. The ordinate represents the ratio (%) of the blood eosinophil fraction relative to the fraction defined as the total cell number in FIG. 4A.

The ratio of an eosinophil fraction was analyzed in the same way as the method described in Example 7(1). The results are shown in FIG. 6A. No large change in the number of eosinophils in peripheral blood was observed in the irradiated mice, compared with unirradiated mice, whereas marked decrease in eosinophils in peripheral blood was confirmed in the cm1B12 antibody- or TRFK-5 antibody-administered group of the irradiated mice, compared with the D-PBS-administered control group of the irradiated mice. The eosinophil-decreasing effect was higher in the cm1B12 antibody than in the TRFK-5 antibody. Accordingly, the cm1B12 antibody and the TRFK-5 antibody were found to also decrease eosinophils in peripheral blood in an irradiated individual.

(ii) Decrease in Small Intestinal Eosinophil

Figure 6B:
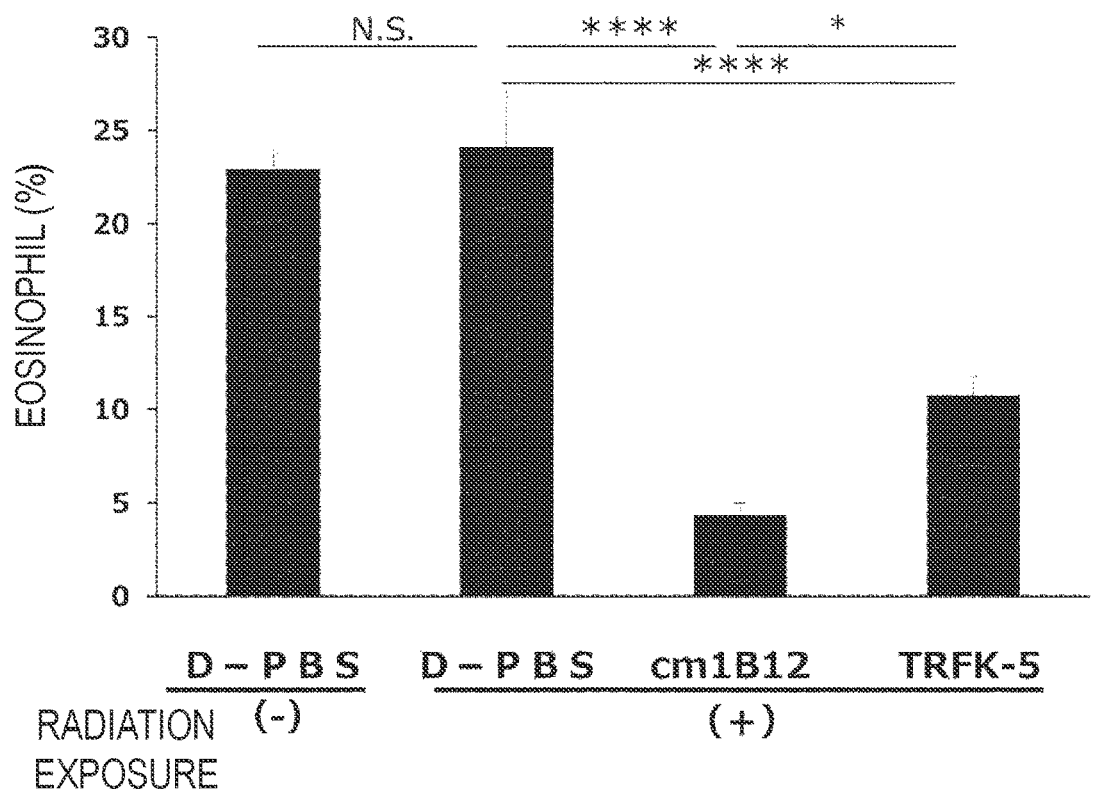
FIG. 6B illustrates the result of analysis of the effect of administration of the cm1B12 antibody or the TRFK-5 antibody on the ratio of small intestinal eosinophils 13 weeks after irradiation. The ordinate represents the ratio (%) of the small intestinal eosinophil fraction relative to the fraction defined as the total cell number in FIG. 5A.

The ratio of an eosinophil fraction was analyzed in the same way as the method described in Example 7(2). The results are shown in FIG. 6B. No change in the number of eosinophils present in the small intestinal lamina propria was observed in the irradiated mice, compared with unirradiated mice, whereas marked decrease in eosinophils present in the small intestinal lamina propria was confirmed in the cm1B12 antibody- or TRFK-5 antibody-administered group of the irradiated mice, compared with the control group, as in the eosinophils in peripheral blood. Thus, the cm1B12 antibody and the TRFK-5 antibody were found to also markedly decrease eosinophils present in the small intestinal lamina propria, as in the eosinophils in peripheral blood, in an irradiated mouse.

(iii) Infiltration of Eosinophil in Small Intestine

A 1.5 cm portion distant by 2 cm from the Treitz's ligament in the small intestine was recovered and fixed by dipping for 1 day in PBS containing 10% formalin. A paraffin block of the fixed small intestine pieces was produced, and a thin section having a thickness of 5 μm was affixed to a glass slide and dried.

The paraffin section was treated with 0.01 N HCl containing 0.1% (w/v) pepsin (MP Biomedicals) at room temperature for 20 minutes and then reacted with an anti-mouse MBP (major basic protein) rat monoclonal antibody (kindly provided by Dr. James J. Lee and Dr. Nancy A. Lee of Mayo Clinic) overnight at 4° C.

The section was washed and then reacted with a biotin-labeled anti-rat IgG goat antibody (Kirkegaard & Perry Laboratories, Inc.) at 37° C. for 1 hour. The section was washed again and then reacted with HRP-labeled streptavidin (Thermo Fisher Scientific Inc.) at room temperature for 30 minutes. Color was developed from the labeled cells using diaminobenzidine as a substrate. MBP-positive cells were regarded as eosinophils, and the number of eosinophils infiltrated per prescribed area in the small intestinal submucosa was measured using BZ-II Image Analysis Application (Keyence Corp.).

As shown in FIGS. 7A and 7B, a large number of MBP-positive eosinophils were infiltrated into the small intestinal submucosa in the irradiated mice, compared with unirradiated mice. In radiation enteritis, the eosinophils were confirmed to specifically infiltrate into the small intestinal submucosa.

On the other hand, the cm1B12 antibody and the TRFK-5 antibody inhibited the infiltration of the MBP-positive eosinophils into the small intestinal submucosa in the irradiated mice, compared with the control. The inhibiting effect on eosinophils into the small intestinal submucosa was stronger in the cm1B12 antibody than in the TRFK-5 antibody. The cm1B12 antibody almost completely inhibited the migration and infiltration of eosinophils as compared with the control.

Thus, the cm1B12 antibody and the TRFK-5 antibody were found to not only decrease eosinophils localized to the small intestinal lamina propria but inhibit the migration and infiltration of the eosinophils into the small intestinal submucosa, as a result of inhibiting the eosinophils through their IL-5-IL-5R neutralizing effects or ADCC activity targeting IL-5R. Particularly, the anti-IL-5Rα antibody was found to be able to more strongly inhibit eosinophils both in the small intestinal lamina propria and in the submucosa than the anti-IL-5 antibody.

(iv) Fibrosis of Small Intestinal Submucosa

In order to observe collagen fiber under an optical microscope, a paraffin section prepared by the method described in the paragraph (iii) was stained with Azan. The thickness of a collagen layer deposited in the submucosa was measured using BZ-II Image Analysis Application (Keyence Corp.).

Figure 8A:
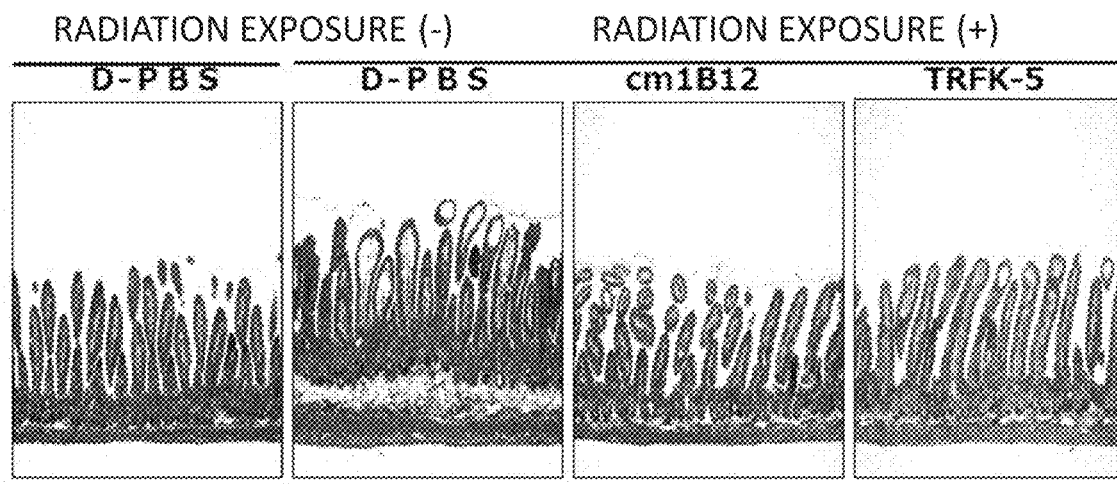
FIG. 8A illustrates the suppressive effect of administration of the cm1B12 antibody or the TRFK-5 antibody on fibrosis of the small intestinal submucosa 13 weeks after irradiation.
Figure 8B:
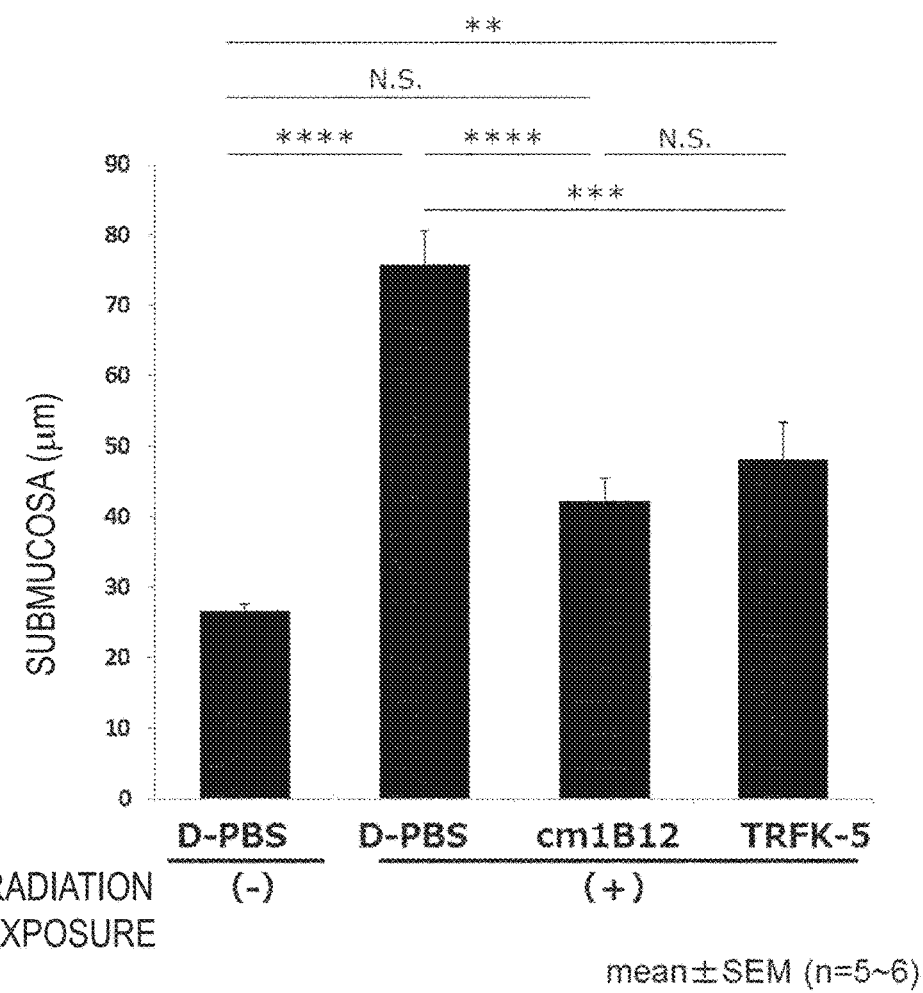
FIG. 8B illustrates the suppressive effect of administration of the cm1B12 antibody or the TRFK-5 antibody on hyperplasia of the small intestinal submucosa 13 weeks after irradiation. The ordinate represents the thickness (μm) of the submucosa.

As shown in FIGS. 8A and 8B, the hyperplasia of the small intestinal submucosa was observed in the irradiated mice, compared with unirradiated mice. By contrast, decrease in the hyperplasia of the small intestinal submucosa as well as marked decrease in the accumulation of collagen in the small intestinal submucosa was observed in the cm1B12a antibody- and TRFK-5 antibody-administered groups of the irradiated mice, confirming that the fibrosis of the submucosa was suppressed.

Thus, the cm1B12 antibody and the TRFK-5 antibody were found to be able to inhibit the eosinophil-dependent fibrosis of the small intestinal submucosa in radiation enteritis, as a result of inhibiting the eosinophils through their IL-5-IL-5R neutralizing effects or ADCC activity targeting IL-5R.

Thus, the results of this Example demonstrated that the anti-IL-5R antibody and the anti-IL-5 antibody can suppress intestinal inflammation and intestinal fibrosis by inhibiting the migration and infiltration of eosinophils into the intestinal lamina propria and the submucosa and the cell proliferation of eosinophils through their IL-5-IL-5R neutralizing effects or ADCC activity targeting IL-5R, and are therefore useful in the treatment of radiation damage.

Example 9: Suppressive Effect of Anti-CCR3 Neutralizing Antibody on Radiation Enteritis (Delayed Damage)

To each mouse irradiated by the method described in Example 8(1), a rat anti-mouse CCR3 neutralizing antibody 83103 (R&D Systems Inc.) was intraperitoneally administered at 5 mg/kg a total of 8 times at 2-week intervals from 2 weeks before the irradiation to 12 weeks after the irradiation. Thirteen weeks after the irradiation, blood and tissues were collected and evaluated for the ratio of an eosinophil fraction in the small intestinal lamina propria, the number of eosinophils infiltrated into the small intestinal submucosa, and the fibrosis of the small intestinal submucosa by the methods described in Examples 7(2), 8(2) (iii) and 8(2) (iv), respectively.

Figure 9A:
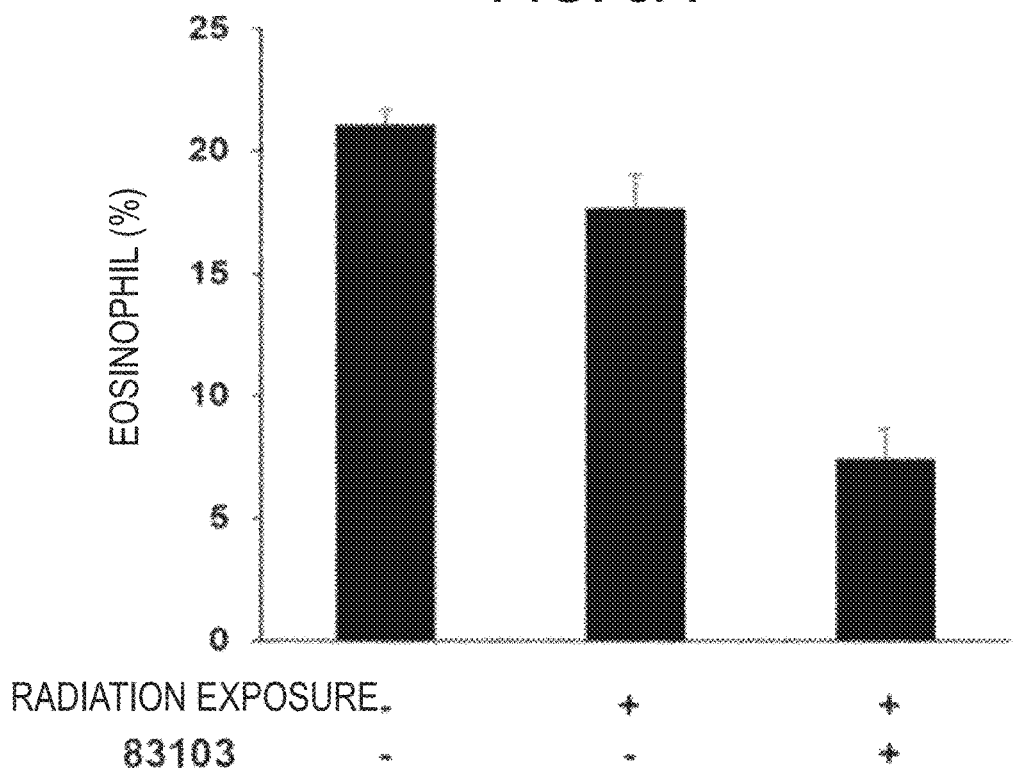
FIG. 9A illustrates the result of analysis of the effect of administration of the 83103 antibody on the ratio of small intestinal eosinophils 13 weeks after the irradiation. The ordinate represents the ratio (%) of the small intestinal eosinophil fraction relative to the monocyte and granulocyte fraction defined as the total cell number.
Figure 9B:
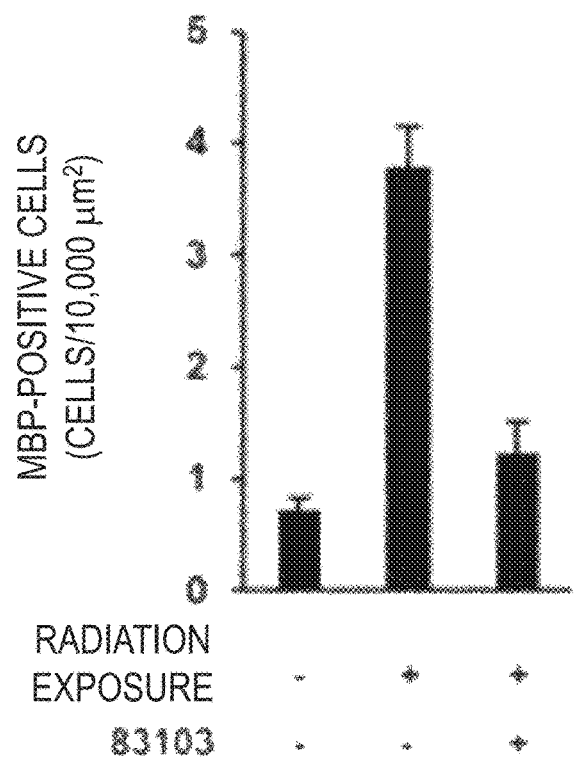
FIG. 9B illustrates the result of analysis of the effect of administration of the 83103 antibody on the number of eosinophils per unit area in the small intestinal submucosa 13 weeks after irradiation.
Figure 9C:
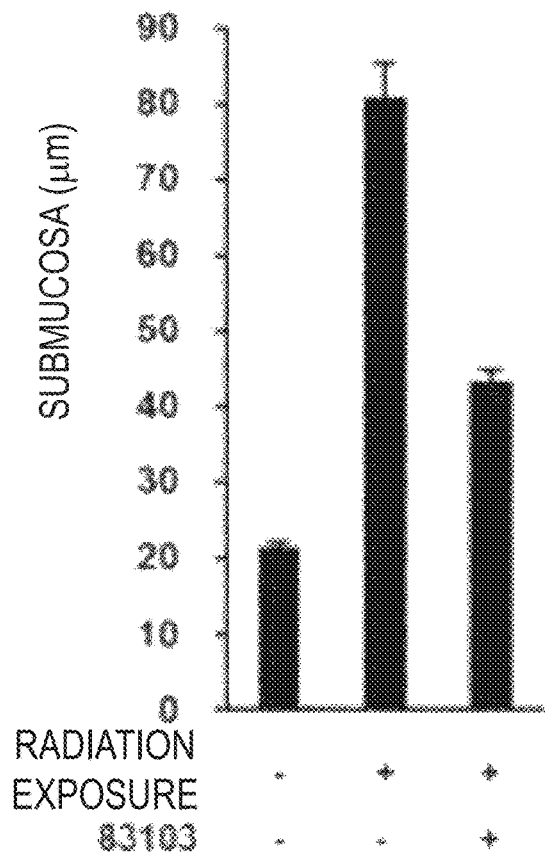
FIG. 9C illustrates the suppressive effect of administration of the 83103 antibody on hyperplasia of the small intestinal submucosa 13 weeks after irradiation. The ordinate represents the thickness (μm) of the submucosa.

As shown in FIGS. 9A to 9C, decrease in eosinophils in the small intestinal lamina propria, inhibition of the migration and infiltration of eosinophils into the small intestinal submucosa, and suppression of the fibrosis of the small intestinal submucosa were confirmed, as in the administration of the anti-IL-5 antibody or the anti-IL-5R antibody.

CCR3 has been confirmed to participate in the migration of eosinophils into the intestinal lamina propria and the submucosa (data not shown). The results of this Example demonstrated that the eosinophil-dependent fibrosis of the small intestinal submucosa in radiation enteritis can also be inhibited by the inhibition of eosinophil migration by the anti-CCR3 neutralizing antibody. These results indicate that radiation damage can be treated by the removal of eosinophils using any of an eosinophil-removing agent having ADCC activity, an eosinophil-removing agent having neutralization activity, and an eosinophil-removing agent having both the activities as the eosinophil-removing agent.

Example 10: Suppressive Effect of cm1B12 Antibody on Radiation Enteritis Associated with X-Ray Dose Fractionation Therapy (1) Induction of Radiation Enteritis (Delayed Damage)

Each mouse was generally anesthetized with three types of mixed anesthetic agents and then repetitively irradiated with 8 Gy (80 to 90 cGy/min) of X-ray once a week a total of one to five times using an X-ray irradiation apparatus MBR-1520R-4 (Hitachi Power Solutions Co., Ltd.) with regions other than the abdomen shielded with a lead plate. The mouse thus irradiated was raised by the free ingestion of feed and drinking water.

(2) Pathological Condition Suppressive Effect of cm1B12 Antibody

D-PBS, or the cm1B12 antibody diluted into 1 mg/mL with D-PBS was intraperitoneally administered at 5 mg/kg on 2-week intervals from 4 weeks before the irradiation to 20 weeks after the first irradiation. Twenty weeks after the irradiation, blood and tissues were collected and analyzed.

(i) Decrease in Eosinophil in Blood

Figure 10:
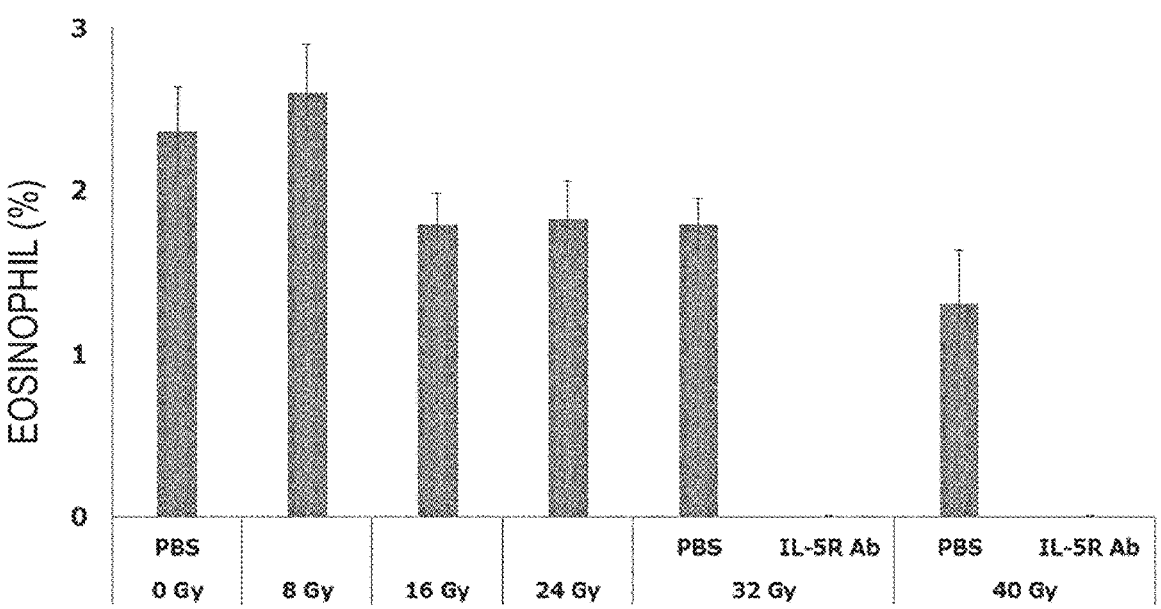
FIG. 10 illustrates the change in the number of eosinophils in the blood and the change in the ratio of blood eosinophils by administration of the cm1B12 antibody 20 weeks after irradiation. The ordinate represents the ratio (%) of eosinophils. The abscissa represents the total dose and the administered agents.

The ratio of an eosinophil fraction was analyzed in the same way as the method described in Example 7(1). The results are shown in FIG. 10. The eosinophils in peripheral blood were completely removed in the cm1B12 antibody-administered group of the mice irradiated. Accordingly, the cm1B12 antibody was found to also decrease eosinophils in peripheral blood in an individual irradiated.

(ii) Intestinal Infiltration of Eosinophil

A 2 cm portion distant by 2 cm from the Treitz's ligament in the intestinal tract was recovered and fixed by dipping for 1 day in PBS containing 10% formalin. A paraffin block of the fixed small intestine pieces was produced, and a thin section having a thickness of 5 µm was affixed to a glass slide and dried. The paraffin section was stained with hematoxylin-eosin (HE).

Figure 11:
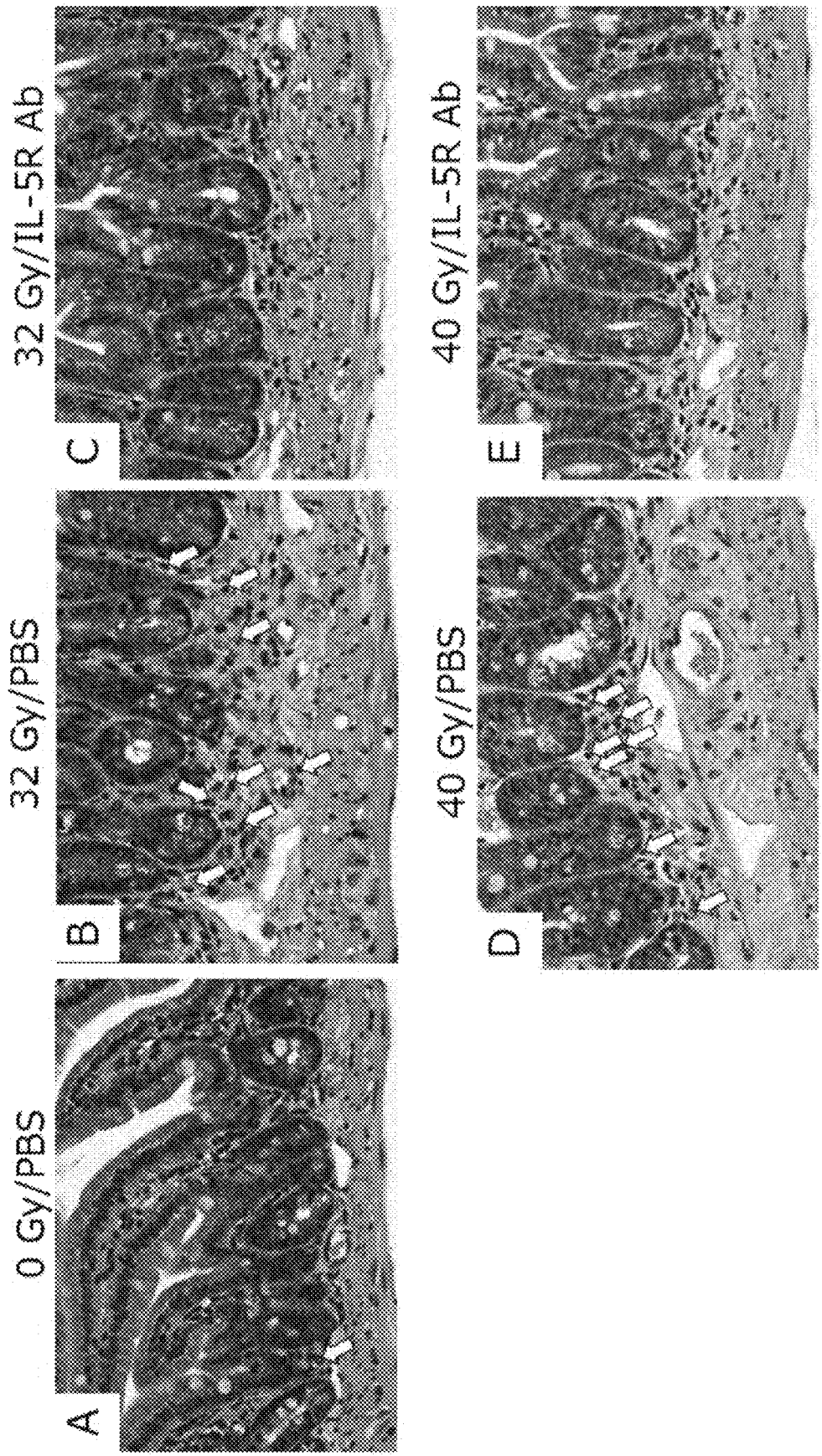
FIG. 11 illustrates the result of analysis of the effect of administration of the cm1B12 antibody on eosinophil infiltration into the intestinal submucosa 20 weeks after irradiation. The arrows indicate eosinophils.

As shown in FIG. 11, a large number of eosinophils were infiltrated into the submucosa in the irradiated mice (B and D), compared with unirradiated mice (A). On the other hand, the cm1B12 antibody completely inhibited the infiltration of the eosinophils into the intestinal submucosa in the irradiated mice, compared with the control (C and E).

Thus, the cm1B12 antibody was found to not only decrease eosinophils localized to the intestinal lamina propria but inhibit the migration and infiltration of the eosinophils into the submucosa, as a result of inhibiting the eosinophils through its IL-5-IL-5R neutralizing effect or ADCC activity targeting IL-5R.

(iii) Intestinal Fibrosis

In order to observe collagen fiber under an optical microscope, the paraffin section was stained with Azan. The thickness of the submucosa and the thickness of a collagen layer deposited therein were measured using ImageScope Ver. 12 (Leica Camera AG).

Figure 12:
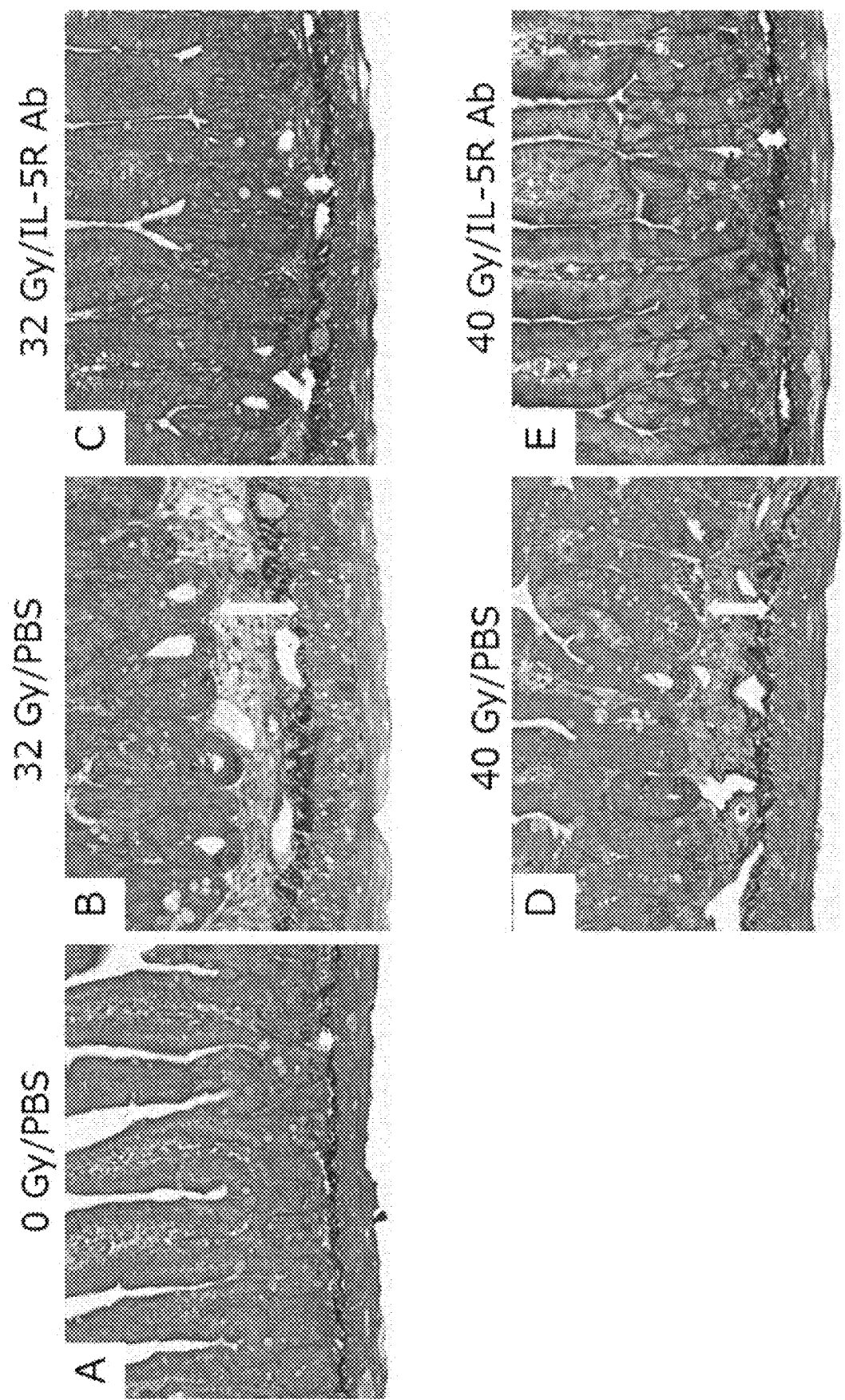
FIG. 12 illustrates the result of analysis of the effect of administration of the cm1B12 antibody on hyperplasia of the intestinal submucosa 20 weeks after irradiation. The arrows indicate fibrous layers.
Figure 13:
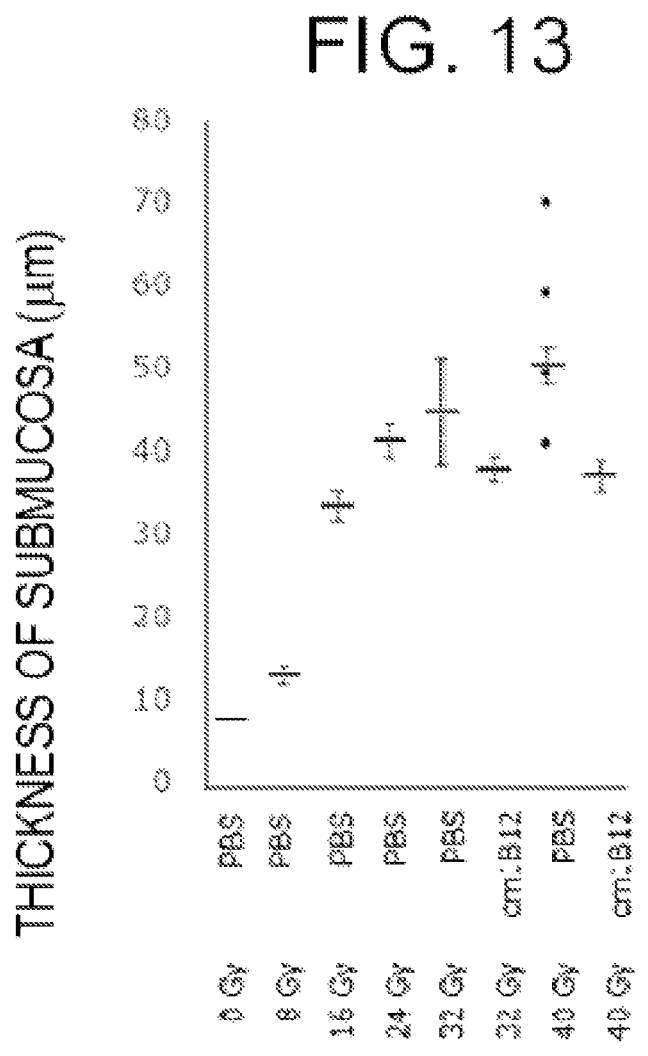

As shown in FIGS. 12 and 13, the hyperplasia of the intestinal submucosa was confirmed in correlation to the total dose of radiation in the PBS group (B and D). On the other hand, the hyperplasia of the submucosa and the accumulation of collagen were decreased in the cm1B12 antibody-administered group compared with the PBS group irradiated at the same level thereas, confirming that the fibrosis of the submucosa was suppressed (C and E). Also, the degree of hyperplasia of the submucosa in the cm1B12 antibody-administered group irradiated at a total dose of 32 Gy or 40 Gy was confirmed to be suppressed to be equivalent to or lower than the degree of hyperplasia of the submucosa in the PBS group irradiated at a total dose of 24 Gy. This suggested that radiation therapy at a total dose higher by at least 30% to 70% and radiation therapy with the number of times of irradiation larger by at least 1 or 2 are accepted by the administration of the cm1B12 antibody.

Thus, the cm1B12 antibody was found to be able to inhibit eosinophil-dependent intestinal inflammation and fibrosis in radiation enteritis and to increase the tolerance dose of radiation for the intestinal tract, as a result of inhibiting the eosinophils through its IL-5-IL-5R neutralizing effect or ADCC activity targeting IL-5R. These results demonstrated that combined use with an eosinophil-removing agent suppresses radiation damage and permits high-dose radiation therapy.

(iv) Intestinal Damage

In order to evaluate comprehensive influence, including intestinal inflammation and fibrosis, etc., associated with abdominal radiation damage, the length from the pylorus of the stomach to the upper part of the cecum was measured.

Figure 14:
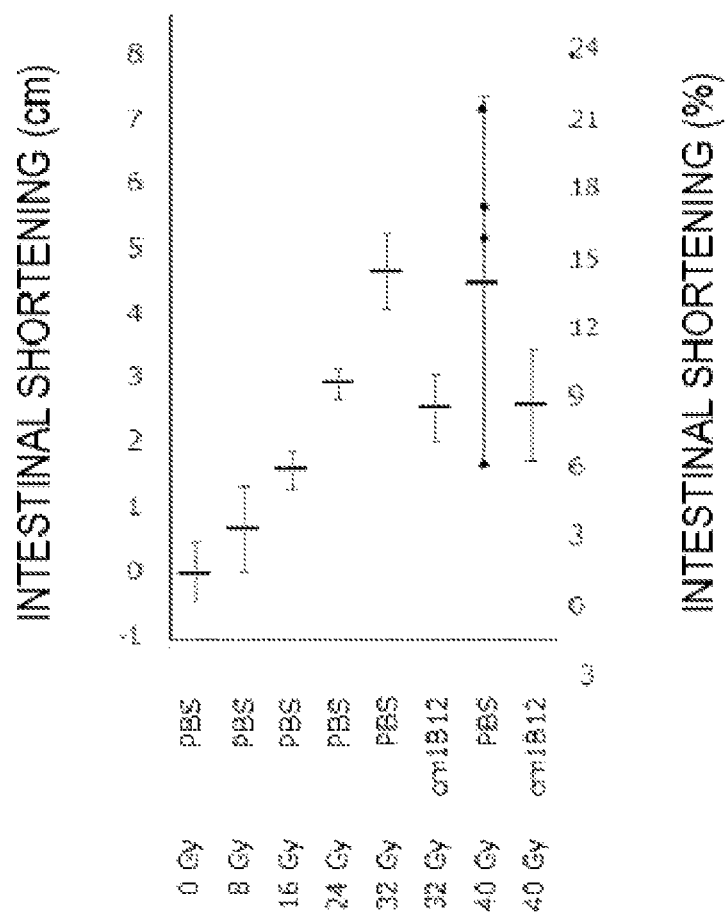
FIG. 14 illustrates the result of analysis of the correlation between intestinal shortening 20 weeks after irradiation and the total dose of radiation and the effect of administration of the cm1B12 antibody. The ordinate (left) represents the length (cm) of the intestinal shortening on the basis of the 0 Gy group. The ordinate (right) represents the ratio (%) of intestinal shortening on the basis of the 0 Gy group. The abscissa represents the total dose and the administered agents. The data of survivor individuals is expressed as the mean. The data of euthanized individuals is represented by the filled circles.

As shown in FIG. 14, the length of the intestinal tract was confirmed to be shortened in correlation to the total dose of radiation in the PBS group. On the other hand, the intestinal shortening was confirmed to be suppressed in the cm1B12 antibody-administered group compared with the PBS group irradiated at the same level thereas. Also, the degree of intestinal shortening in the cm1B12 antibody-administered group irradiated at a total dose of 32 Gy or 40 Gy was confirmed to be suppressed to be equivalent to or lower than the degree of intestinal shortening in the PBS group irradiated at a total dose of 24 Gy. This suggested that radiation therapy at a total dose higher by at least 30% to 70% and radiation therapy with the number of times of irradiation larger by at least 1 or 2 are accepted by the administration of the cm1B12 antibody.

Thus, the cm1B12 antibody was found to be able to reduce intestinal damage in radiation enteritis and to increase the tolerance dose of radiation for the intestinal tract, as a result of inhibiting the eosinophils through its IL-5-IL-5R neutralizing effect or ADCC activity targeting IL-5R.

(v) Weight Loss Associated with Development of Pathological Condition

In order to evaluate systemic influence, mainly eating disorder and nutrient malabsorption, associated with abdominal radiation damage, time-dependent change in body weight was evaluated.

Figure 15:
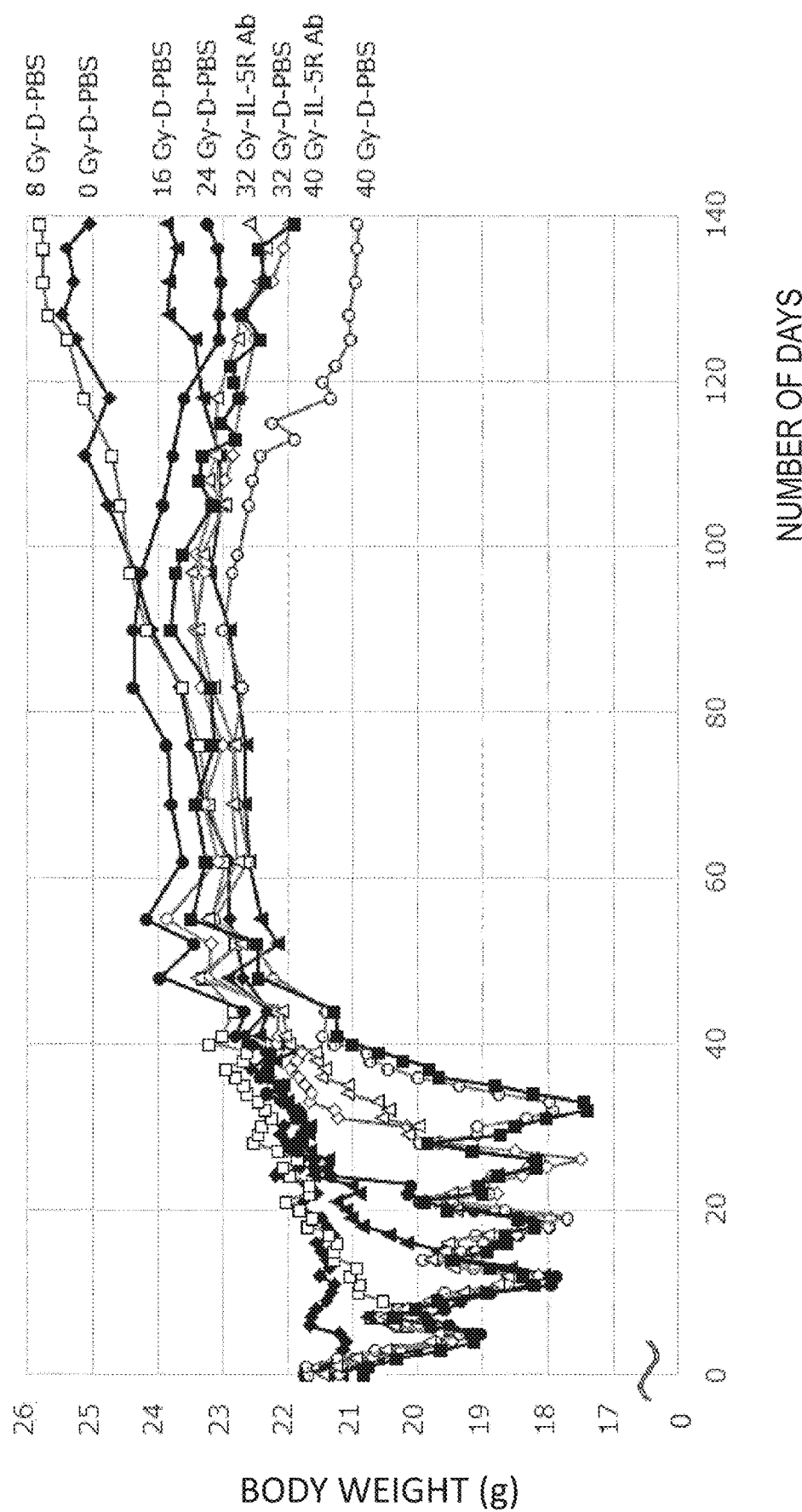
FIG. 15 illustrates the result of analysis of the effect of irradiation on the change in body weight and the effect of administration of the cm1B12 antibody. The ordinate represents the body weight (g). The abscissa represents the number of days (days) from the date of the first irradiation. Each line represents the mean of the PBS-administered group irradiated of a total dose of 0, 8, 16, 24, 32, or 40 Gy or the cm1B12 antibody-administered group irradiated of a total dose of 32 or 40 Gy. The value for the PBS-administered group or the cm1B12 antibody-administered group irradiated with 40 Gy is the mean of those without fatal individuals.

As shown in FIG. 15, the body weight decreased in a manner dependent on the number of times of irradiation at the time of induction of the pathological condition, but rapidly recovered to the body weight equivalent to that before the irradiation in all the individuals after the completion of induction of the pathological condition, and continued to increase for a certain period, as in a nonirradiated group. On the other hand, when the mice were raised for a long period, increase in body weight was evidently hindered in the group irradiated at a total dose of 16 Gy or more, compared with the nonirradiated group, and weight loss was confirmed over time in the group irradiated at a total dose of 24 Gy or more. No evident difference was confirmable among 4 groups, the PBS groups irradiated at total doses of 24 Gy and 32 Gy and the cm1B12 antibody-administered groups irradiated at total doses of 32 Gy and 40 Gy. On the other hand, the PBS group irradiated with 40 Gy of radiation exhibited significant weight loss as compared with the other groups.

Thus, the cm1B12 antibody was found to be able to reduce damage, mainly eating disorder and nutrient malabsorption, associated with radiation damage, and to increase the tolerance dose of radiation, as a result of inhibiting the eosinophils through its IL-5-IL-5R neutralizing effect or ADCC activity targeting IL-5R.

(vi) Survival Curve

In order to evaluate systemic influence associated with abdominal radiation damage, a survival rate was evaluated. The survival curve was calculated by measuring, over time, the numbers of individuals that died naturally in association with the aggravation of the pathological condition, and euthanized individuals. The euthanasia was carried out on individuals in mortal danger, specifically, individuals that lost their body weights by 15% or more from the initial body weight, from the viewpoint of animal protection, excluding the time of induction of the pathological condition.

Figure 16:
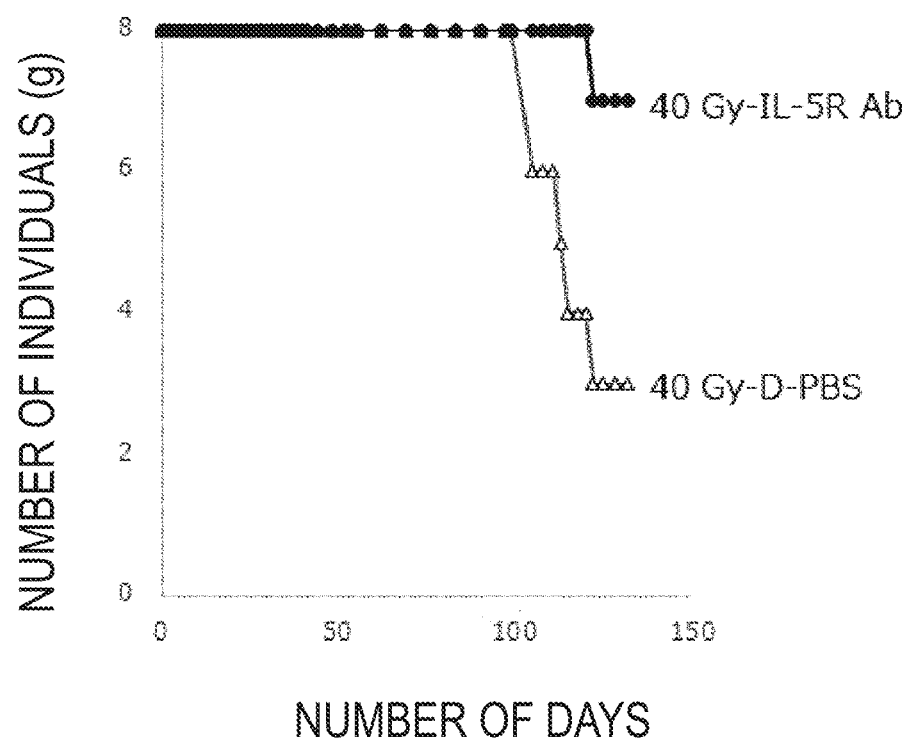
FIG. 16 illustrates the result of analysis of the survival curve of the group irradiated with radiation of a total dose of 40 Gy and the effect of administration of the cm1B12 antibody. Each line represents the survival curve of the PBS-administered group or the cm1B12 antibody-administered group. The ordinate represents the number of survivor individuals. The abscissa represents the number of days (days) from the date of the first irradiation with radiation.

As shown in FIG. 16, the survival rate markedly decreased over time in the PBS-administered group irradiated at a total dose of 40 Gy, whereas the survival rate was markedly improved in the cm1B12 antibody-administered group irradiated at a total dose of 40 Gy.

Thus, the cm1B12 antibody was found to be able to reduce severe radiation damage influencing vital prognosis, associated with abdominal radiation damage, as a result of inhibiting the eosinophils through its IL-5-IL-5R neutralizing effect or ADCC activity targeting IL-5R.

Thus, the results of this Example demonstrated that the anti-IL-5R antibody and the anti-IL-5 antibody can improve a long-term survival rate, mitigate a progressive pathological condition involving weight loss, and suppress intestinal damage such as intestinal shortening, intestinal inflammation and intestinal fibrosis, by inhibiting the migration and infiltration of eosinophils into the intestinal lamina propria and the submucosa and the cell proliferation of eosinophils through their IL-5-IL-5R neutralizing effects or ADCC activity targeting IL-5R, and are therefore useful in the treatment of radiation damage.

FREE TEXT OF SEQUENCE LISTING

SEQ ID NO: 1: Amino acid sequence of benralizumab HCDR1
SEQ ID NO: 2: Amino acid sequence of benralizumab HCDR2
SEQ ID NO: 3: Amino acid sequence of benralizumab HCDR3
SEQ ID NO: 4: Amino acid sequence of benralizumab LCDR1
SEQ ID NO: 5: Amino acid sequence of benralizumab LCDR2
SEQ ID NO: 6: Amino acid sequence of benralizumab LCDR3
SEQ ID NO: 7: Amino acid sequence of benralizumab VH
SEQ ID NO: 8: Amino acid sequence of benralizumab VL
SEQ ID NO: 9: Amino acid sequence of benralizumab H chain
SEQ ID NO: 10: Amino acid sequence of benralizumab L chain
SEQ ID NO: 11: Nucleotide sequence of mouse IL-5Rα cDNA
SEQ ID NO: 12: Nucleotide sequence of 1B12 antibody H chain variable region
SEQ ID NO: 13: Amino acid sequence of 1B12 antibody H chain variable region (including signal sequence)
SEQ ID NO: 14: Amino acid sequence of 1B12 antibody H chain variable region (excluding signal sequence)
SEQ ID NO: 15: Nucleotide sequence of 1B12 antibody L chain variable region
SEQ ID NO: 16: Amino acid sequence of 1B12 antibody L chain variable region (including signal sequence)
SEQ ID NO: 17: Amino acid sequence of 1B12 antibody L chain variable region (excluding signal sequence)

The invention claimed is:

1. A method for treating radiation damage associated with radiation exposure during radiation therapy of cancer in a patient, wherein the radiation therapy is radiation therapy for any cancer selected from the group consisting of small intestinal cancer, colorectal cancer, gastrointestinal stromal tumor (GIST), gastrointestinal carcinoid, gastric cancer, esophageal cancer, liver cancer, gallbladder/biliary cancer, pancreatic cancer, pancreatic/gastrointestinal neuroendocrine tumor, Langerhans cell histiocytosis, renal cell cancer, renal pelvic/ureteral cancer, adrenal tumor, osteosarcoma, soft tissue sarcoma, malignant lymphoma, bladder cancer, urethral cancer, prostate cancer, testicular tumor, penile cancer, endometrial cancer, cervical cancer, uterine tumor, ovarian tumor, female genital cancer, lung cancer, thymic tumor, mesothelioma, and breast cancer, wherein the method comprises administering an effective amount of an IL-5 receptor α chain binding antibody, wherein the IL-5 receptor α chain binding antibody or antibody-binding fragment thereof comprises:

a heavy chain variable region comprising a complementary determining region 1 (HCDR1), a complementary determining region 2 (HCDR2) and a complementary determining region 1 (HCDR3) comprising the amino acid sequences SEQ ID NO: 1, SEQ ID NO: 2, and SEQ ID NO: 3, respectively; and a light chain variable region comprising a complementary determining region 1 (LCDR1), a complementary determining region 2 (LCDR2), and a complementary determining region 3 (LCDR3) comprising the amino acid sequences of SEQ ID NO: 4, SEQ ID NO: 5, and SEQ ID NO: 6, respectively.

2. The method according to claim 1, wherein the radiation is X-ray radiation or γ-ray radiation.

3. The method according to claim 1, wherein the radiation damage is early radiation damage or delayed radiation damage.

4. The method according to claim 1, wherein the radiation damage is damage to any one or more organs selected from the group consisting of the small intestine, the large intestine, the stomach, the bladder, the liver, and the kidney.

5. The method according to claim 1, wherein the antibody or the fragment thereof is an antibody or a fragment thereof having antibody-dependent cellular cytotoxicity activity.

6. The method according to claim 1, wherein the IL-5 receptor α chain binding antibody comprises a human Fc region or a human constant region.

7. The method according to claim 1, wherein the IL-5 receptor α chain binding antibody is any antibody selected from the group consisting of a chimeric antibody, a humanized antibody, and a human antibody.

8. The method according to claim 1, wherein the radiation damage associated with the radiation therapy is suppressed by at least 5% in a patient treated with the IL-5 receptor α chain binding antibody compared to a patient receiving radiation therapy without IL-5 receptor α chain binding antibody treatment.

9. The method according to claim 1, wherein a tolerance radiation dose for the radiation therapy of the patient treated with the IL-5 receptor α chain binding antibody is increased by 5% or more compared to that for a patient receiving radiation therapy without IL-5 receptor α chain binding antibody treatment.

10. The method according to claim 1, wherein the radiation damage is damage to the small intestine or the large intestine.

* * * * *

```
                         SEQUENCE LISTING

<160> NUMBER OF SEQ ID NOS: 17

<210> SEQ ID NO 1
<211> LENGTH: 5
<212> TYPE: PRT
<213> ORGANISM: Artificial Sequence
<220> FEATURE:
<223> OTHER INFORMATION: Amino acid sequence of  HCDR1 of Benralizumab

<400> SEQUENCE: 1

Ser Tyr Val Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Amino acid sequence of  HCDR2 of Benralizumab

<400> SEQUENCE: 2

Tyr Ile Asn Pro Tyr Asn Asp Gly Thr Lys Tyr Asn Glu Arg Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Amino acid sequence of  HCDR3 of Benralizumab

<400> SEQUENCE: 3

Glu Gly Ile Arg Tyr Tyr Gly Leu Leu Gly Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Amino acid sequence of  LCDR1 of Benralizumab

<400> SEQUENCE: 4
```

```
Gly Thr Ser Glu Asp Ile Ile Asn Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Amino acid sequence of LCDR2 of Benralizumab

<400> SEQUENCE: 5

His Thr Ser Arg Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Amino acid sequence of LCDR3 of Benralizumab

<400> SEQUENCE: 6

Gln Gln Gly Tyr Thr Leu Pro Tyr Thr
1               5

<210> SEQ ID NO 7
<211> LENGTH: 121
<212> TYPE: PRT
<213> ORGANISM: Artificial Sequence
<220> FEATURE:
<223> OTHER INFORMATION: Amino acid sequence of VH of Benralizumab

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile His Trp Val Arg Gln Arg Pro Gly Gln Gly Leu Ala Trp Met
        35                  40                  45

Gly Tyr Ile Asn Pro Tyr Asn Asp Gly Thr Lys Tyr Asn Glu Arg Phe
    50                  55                  60

Lys Gly Lys Val Thr Ile Thr Ser Asp Arg Ser Thr Ser Thr Val Tyr
65                  70                  75                  80

Met Glu Leu Ser Ser Leu Arg Ser Glu Asp Thr Ala Val Tyr Leu Cys
                85                  90                  95

Gly Arg Glu Gly Ile Arg Tyr Tyr Gly Leu Leu Gly Asp Tyr Trp Gly
            100                 105                 110

Gln Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Amino acid sequence of VL of Benralizumab

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gly Thr Ser Glu Asp Ile Ile Asn Tyr
            20                  25                  30
```

```
Leu Asn Trp Tyr Gln Gln Lys Pro Gly Lys Ala Pro Lys Leu Leu Ile
        35                  40                  45

Tyr His Thr Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Leu Pro Tyr
                85                  90                  95

Thr Phe Gly Gln Gly Thr Lys Val Glu Ile Lys
                100                 105

<210> SEQ ID NO 9
<211> LENGTH: 451
<212> TYPE: PRT
<213> ORGANISM: Artificial Sequence
<220> FEATURE:
<223> OTHER INFORMATION: Amino acid sequence of heavy chain of
      Benralizumab

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile His Trp Val Arg Gln Arg Pro Gly Gln Gly Leu Ala Trp Met
        35                  40                  45

Gly Tyr Ile Asn Pro Tyr Asn Asp Gly Thr Lys Tyr Asn Glu Arg Phe
    50                  55                  60

Lys Gly Lys Val Thr Ile Thr Ser Asp Arg Ser Thr Ser Thr Val Tyr
65                  70                  75                  80

Met Glu Leu Ser Ser Leu Arg Ser Glu Asp Thr Ala Val Tyr Leu Cys
                85                  90                  95

Gly Arg Glu Gly Ile Arg Tyr Tyr Gly Leu Leu Gly Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
```

```
                275                 280                 285
His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 10
<211> LENGTH: 155
<212> TYPE: PRT
<213> ORGANISM: Artificial Sequence
<220> FEATURE:
<223> OTHER INFORMATION: Amino acid sequence of light chain of
      Benralizumab

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gly Thr Ser Glu Asp Ile Ile Asn Tyr
                20                  25                  30

Leu Asn Trp Tyr Gln Gln Lys Pro Gly Lys Ala Pro Lys Leu Leu Ile
            35                  40                  45

Tyr His Thr Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Leu Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln
145                 150                 155

<210> SEQ ID NO 11
<211> LENGTH: 1248
```

<212> TYPE: DNA
<213> ORGANISM: Rattus norvegicus

<400> SEQUENCE: 11

```
atggtgcctg tgttactaat tcttgtggga gctttggcaa cactgcaagc tgacttactt    60
aatcacaaaa agtttttact tctaccacct gtcaattta ccattaaagc cactggatta   120
gctcaagttc ttttacactg ggacccaaat cctgaccaag agcaaaggca tgttgatcta   180
gagtatcacg tgaaaataaa tgccccacaa gaagacgaat atgataccag aaagactgaa   240
agcaaatgtg tgacccccct tcatgaaggc tttgcagcta gcgtgaggac cattctgaag   300
agcagccata caactctggc cagcagttgg gtttctgctg aactcaaagc tccaccagga   360
tctcctggaa cctcggttac gaatttaact tgtaccacac acactgttgt aagtagccac   420
acccacttaa ggccatacca agtgtccctt cgttgcacct ggcttgttgg gaaggatgcc   480
cctgaggaca cacagtattt cctatactac aggtttggtg ttttgactga aaaatgccaa   540
gaatacagca gagatgcact gaacagaaat actgcatgct ggtttcccag acatttatc    600
aacagcaaag ggtttgagca gcttgctgtg cacattaatg gctcaagcaa gcgtgctgca   660
atcaagccct ttgatcagct gttcagtcca cttgccattg accaagtgaa tcctccaagg   720
aatgtcacag tggaaattga agcaattct ctctatatac agtgggagaa accactttct    780
gcctttccag atcattgctt taactatgag ctgaaaattt acaacacaaa aaatggtcac   840
attcagaagg aaaaactgat cgccaataag ttcatctcaa aaattgatga tgtttctaca   900
tattccattc aagtgagagc agctgtgagc tcaccttgca gaatgccagg aaggtggggc   960
gagtggagtc aacctattta tgtgggaaag gaaaggaagt ccttggtaga atggcatctc  1020
attgtgctcc caacagccgc ctgcttcgtc ttgttaatct tctcactcat ctgcagagtg  1080
tgtcatctat ggaccaggtt gtttccaccg gttccggccc caaagagtaa catcaaagat  1140
ctccctgtgg ttactgaata tgagaaacct tcgaatgaaa ccaaaattga agttgtacat  1200
tgtgtggaag aggttggatt tgaagtcatg ggaaattcca cgttttga                1248
```

<210> SEQ ID NO 12
<211> LENGTH: 411
<212> TYPE: DNA
<213> ORGANISM: Rattus norvegicus
<220> FEATURE:
<221> NAME/KEY: CDS
<222> LOCATION: (1)..(411)

<400> SEQUENCE: 12

```
atg gac atc agg ctc agc ttg gtt ttc ctt gtc ctt ttc ata aaa ggt     48
Met Asp Ile Arg Leu Ser Leu Val Phe Leu Val Leu Phe Ile Lys Gly
1               5                   10                  15 gtc cag tgt gag gtg cag ctg gtg gag tct gat gga ggc tta gta caa     96
Val Gln Cys Glu Val Gln Leu Val Glu Ser Asp Gly Gly Leu Val Gln
            20                  25                  30 cct gga agg tcc cta aaa ctc tcc tgt gca gcc tca gga ttc act ttc    144
Pro Gly Arg Ser Leu Lys Leu Ser Cys Ala Ala Ser Gly Phe Thr Phe
        35                  40                  45 agt gac ttt tac atg gcc tgg gtc cgc cag gct cca acg aag ggg ctg    192
Ser Asp Phe Tyr Met Ala Trp Val Arg Gln Ala Pro Thr Lys Gly Leu
    50                  55                  60 gaa tgg gtc gca acc att agt tat gat ggt agt agc gct tac tat cga    240
Glu Trp Val Ala Thr Ile Ser Tyr Asp Gly Ser Ser Ala Tyr Tyr Arg
65                  70                  75                  80 gac tcc gtg aag ggc cga ttc act atc tcc aga gat aat gca aaa agc    288
```

```
Asp Ser Val Lys Gly Arg Phe Thr Ile Ser Arg Asp Asn Ala Lys Ser
                85                  90                  95 acc cta tac ctg caa atg gac agt ctg agc tct gag gac acg gcc act    336
Thr Leu Tyr Leu Gln Met Asp Ser Leu Ser Ser Glu Asp Thr Ala Thr
            100                 105                 110 tat tac tgt gca aga cat gac ggt tat tac ccc ttt gat tac tgg ggc    384
Tyr Tyr Cys Ala Arg His Asp Gly Tyr Tyr Pro Phe Asp Tyr Trp Gly
        115                 120                 125 caa gga gtc atg gtc aca gtc tcc tca                                411
Gln Gly Val Met Val Thr Val Ser Ser
    130                 135

<210> SEQ ID NO 13
<211> LENGTH: 137
<212> TYPE: PRT
<213> ORGANISM: Rattus norvegicus

<400> SEQUENCE: 13

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
            20                  25                  30

Pro Gly Arg Ser Leu Lys Leu Ser Cys Ala Ala Ser Gly Phe Thr Phe
        35                  40                  45

Ser Asp Phe Tyr Met Ala Trp Val Arg Gln Ala Pro Thr Lys Gly Leu
    50                  55                  60

Glu Trp Val Ala Thr Ile Ser Tyr Asp Gly Ser Ser Ala Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Ser Ser Glu Asp Thr Ala Thr
            100                 105                 110

Tyr Tyr Cys Ala Arg His Asp Gly Tyr Tyr Pro Phe Asp Tyr Trp Gly
        115                 120                 125

Gln Gly Val Met Val Thr Val Ser Ser
    130                 135

<210> SEQ ID NO 14
<211> LENGTH: 117
<212> TYPE: PRT
<213> ORGANISM: Rattus norvegicus

<400> SEQUENCE: 14

Val Gln Leu Val Glu Ser Asp Gly Gly Leu Val Gln Pro Gly Arg Ser
1               5                   10                  15

Leu Lys Leu Ser Cys Ala Ala Ser Gly Phe Thr Phe Ser Asp Phe Tyr
            20                  25                  30

Met Ala Trp Val Arg Gln Ala Pro Thr Lys Gly Leu Glu Trp Val Ala
        35                  40                  45

Thr Ile Ser Tyr Asp Gly Ser Ser Ala Tyr Tyr Arg Asp Ser Val Lys
    50                  55                  60

Gly Arg Phe Thr Ile Ser Arg Asp Asn Ala Lys Ser Thr Leu Tyr Leu
65                  70                  75                  80

Gln Met Asp Ser Leu Ser Ser Glu Asp Thr Ala Thr Tyr Tyr Cys Ala
                85                  90                  95

Arg His Asp Gly Tyr Tyr Pro Phe Asp Tyr Trp Gly Gln Gly Val Met
            100                 105                 110
```

-continued

Val Thr Val Ser Ser
        115

<210> SEQ ID NO 15
<211> LENGTH: 378
<212> TYPE: DNA
<213> ORGANISM: Rattus norvegicus
<220> FEATURE:
<221> NAME/KEY: CDS
<222> LOCATION: (1)..(378)

<400> SEQUENCE: 15

```
atg ggt gtg cct act cat ctc ctg ggt ttg ttg ctg ctc tgg att aca      48
Met Gly Val Pro Thr His Leu Leu Gly Leu Leu Leu Leu Trp Ile Thr
1               5                   10                  15 cat gcc ata tgt gat atc cgg atg aca cag tct cca gct tcc ctg tct      96
His Ala Ile Cys Asp Ile Arg Met Thr Gln Ser Pro Ala Ser Leu Ser
                20                  25                  30 gca tct ctg gga gaa act gtc aac atc gaa tgt cta gca agt gag gac     144
Ala Ser Leu Gly Glu Thr Val Asn Ile Glu Cys Leu Ala Ser Glu Asp
            35                  40                  45 att tac agt gat tta gca tgg tat caa cag aag cca ggg aaa tct cct     192
Ile Tyr Ser Asp Leu Ala Trp Tyr Gln Gln Lys Pro Gly Lys Ser Pro
        50                  55                  60 cag ctc ctg atc tat gat gca aat agc ttg caa aat ggg gtc cct tca     240
Gln Leu Leu Ile Tyr Asp Ala Asn Ser Leu Gln Asn Gly Val Pro Ser
65                  70                  75                  80 cgg ttt agt ggc agt gga tct ggc aca cag tat tct cta aaa ata aac     288
Arg Phe Ser Gly Ser Gly Ser Gly Thr Gln Tyr Ser Leu Lys Ile Asn
                85                  90                  95 agc ctg caa tct gaa gat gtc gcg act tat ttc tgt caa caa tat aac     336
Ser Leu Gln Ser Glu Asp Val Ala Thr Tyr Phe Cys Gln Gln Tyr Asn
                100                 105                 110 aat tat tgg acg ttc ggt gga ggc acc aag ctg gaa ttg aaa             378
Asn Tyr Trp Thr Phe Gly Gly Gly Thr Lys Leu Glu Leu Lys
            115                 120                 125
```

<210> SEQ ID NO 16
<211> LENGTH: 126
<212> TYPE: PRT
<213> ORGANISM: Rattus norvegicus

<400> SEQUENCE: 16

Met Gly Val Pro Thr His Leu Leu Gly Leu Leu Leu Leu Trp Ile Thr
1               5                   10                  15

His Ala Ile Cys Asp Ile Arg Met Thr Gln Ser Pro Ala Ser Leu Ser
                20                  25                  30

Ala Ser Leu Gly Glu Thr Val Asn Ile Glu Cys Leu Ala Ser Glu Asp
            35                  40                  45

Ile Tyr Ser Asp Leu Ala Trp Tyr Gln Gln Lys Pro Gly Lys Ser Pro
        50                  55                  60

Gln Leu Leu Ile Tyr Asp Ala Asn Ser Leu Gln Asn Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Val Ala Thr Tyr Phe Cys Gln Gln Tyr Asn
                100                 105                 110

Asn Tyr Trp Thr Phe Gly Gly Gly Thr Lys Leu Glu Leu Lys
            115                 120                 125

```
<210> SEQ ID NO 17
<211> LENGTH: 106
<212> TYPE: PRT
<213> ORGANISM: Rattus norvegicus

<400> SEQUENCE: 17

Asp Ile Arg Met Thr Gln Ser Pro Ala Ser Leu Ser Ala Ser Leu Gly
1               5                   10                  15

Glu Thr Val Asn Ile Glu Cys Leu Ala Ser Glu Asp Ile Tyr Ser Asp
            20                  25                  30

Leu Ala Trp Tyr Gln Gln Lys Pro Gly Lys Ser Pro Gln Leu Leu Ile
        35                  40                  45

Tyr Asp Ala Asn Ser Leu Gln Asn Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Thr Tyr Phe Cys Gln Gln Tyr Asn Asn Tyr Trp Thr
                85                  90                  95

Phe Gly Gly Gly Thr Lys Leu Glu Leu Lys
            100                 105
```